(12) United States Patent
Tran

(10) Patent No.: US 11,045,271 B1
(45) Date of Patent: Jun. 29, 2021

(54) ROBOTIC MEDICAL SYSTEM

(71) Applicant: Bao Q Tran, Saratoga, CA (US)

(72) Inventor: Bao Q Tran, Saratoga, CA (US)

(*) Notice: Subject to any disclaimer, the term of this patent is extended or adjusted under 35 U.S.C. 154(b) by 0 days.

(21) Appl. No.: 17/172,048

(22) Filed: Feb. 9, 2021

(51) Int. Cl.
  *A61B 34/30* (2016.01)
  *A61B 34/00* (2016.01)
  *G16H 40/67* (2018.01)
  *G16H 50/80* (2018.01)
  *G06N 20/00* (2019.01)

(52) U.S. Cl.
  CPC .............. *A61B 34/70* (2016.02); *A61B 34/30* (2016.02); *G06N 20/00* (2019.01); *G16H 40/67* (2018.01); *G16H 50/80* (2018.01); *A61B 2034/302* (2016.02)

(58) Field of Classification Search
  CPC ... A61B 5/0022; A61B 5/0077; A61B 5/1113; A61B 5/1114; A61B 5/7275; A61B 5/747; G16H 30/40; G16H 40/67; G16H 50/20; G16H 80/00
  See application file for complete search history.

(56) References Cited

U.S. PATENT DOCUMENTS

| | | | |
|---|---|---|---|
| 5,827,271 A | 10/1998 | Buysse | |
| 6,033,399 A | 3/2000 | Gines | |
| 7,530,979 B2 | 1/2009 | Ganz | |
| 8,235,985 B2 | 8/2012 | Saadat | |
| 8,398,541 B2 | 3/2013 | DiMaio | |
| 8,939,970 B2 | 1/2015 | Stone | |
| 10,098,692 B2 | 10/2018 | Allison | |
| 10,517,681 B2 | 12/2019 | Roh | |
| 10,869,718 B2 | 12/2020 | Rajagopolan | |
| 2005/0115565 A1* | 6/2005 | Geary | B64D 13/06 128/205.11 |
| 2011/0082369 A1 | 4/2011 | Mohr | |
| 2014/0155891 A1 | 6/2014 | Johnson | |
| 2016/0096598 A1* | 4/2016 | Harkrider | B63B 7/08 441/130 |
| 2017/0105621 A1* | 4/2017 | Pratt | G16H 30/40 |
| 2019/0183591 A1* | 6/2019 | Johnson | B25J 9/161 |
| 2021/0059607 A1* | 3/2021 | Gormley | G06N 3/08 |

FOREIGN PATENT DOCUMENTS

CA  2388861 C  9/2013

OTHER PUBLICATIONS

Verma et al., Application of markerless image-based arm tracking to robot-manipulator teleoperation, 2004, IEEE, p. 1-8 (Year: 2004).*
Michel et al., Motion-based robotic self-recognition, 2004, IEEE, pgl 2004, (Year: 2004).*
Kumar et al., Computer-Vision-Based Decision Support in Surgical Robotics, 2015, IEEE, p. 1-9 (Year: 2015).*
Bihlmaier et al., Learning surgical know-how: Dexterity for a cognitive endoscope robot, 2015, IEEE, p. 137-142 (Year: 2015).*

* cited by examiner

*Primary Examiner* — McDieunel Marc
(74) *Attorney, Agent, or Firm* — Tran & Associates

(57) ABSTRACT

A system includes a camera; an AI visual processor to classify and recognize human anatomical features, and a processor to control robot movement to reach a selected anatomical target.

20 Claims, 17 Drawing Sheets

FIG. 1C

Training

Receive HD color and multi-spectral or hyperspectral images along with major landmark images and position data for training Preprocess/desaturate images and color enhance Segment images and identify features Receive position of unit in 3D body space based on position relative to the 3D body space map Align with positioning system and HD map of body landmarks (optional)

Align with body markers to improve accuracy of determined position of unit in 3D body space (optional)

Train DNNs to recognize anatomical structures until error rate are below threshold Operation Illuminate surgical site with visible light and capture color HD image of site Preprocess/desaturate color HD image and color enhance Illuminate surgical site with non-visible light and capture multi-spectra/HS image Segment images and identify features From stereo cameras, generate 3D map of body space Determine position of unit in 3D body space based on position relative to the 3D body space map Align with positioning system and HD map of body landmarks (optional)

Align with body markers to improve accuracy of determined position of unit in 3D body space (optional)

Apply the DNN to infer or recognize the anatomical structure

FIG. 1D

Training

Capture multi-spectral or hyperspectral images along with major landmark images and position data for training Train DNNs to recognize images until error rate are below threshold Operation Capture multi-spectra/HS image Segment images and identify features From stereo cameras, generate 3D map of body space Determine position of unit in 3D body space based on position relative to the 3D body space map Align with ultrawideband (UWB) mapping of body landmarks Align with body markers to improve accuracy of determined position of unit in 3D body space Move unit to a target position Capture samples and annotate the sample with the determined position on command Actuate treatment device at the determined position on command Apply neural network visual inspection to see if rework is needed If needed repeat treatment, else exit FIG. 2C
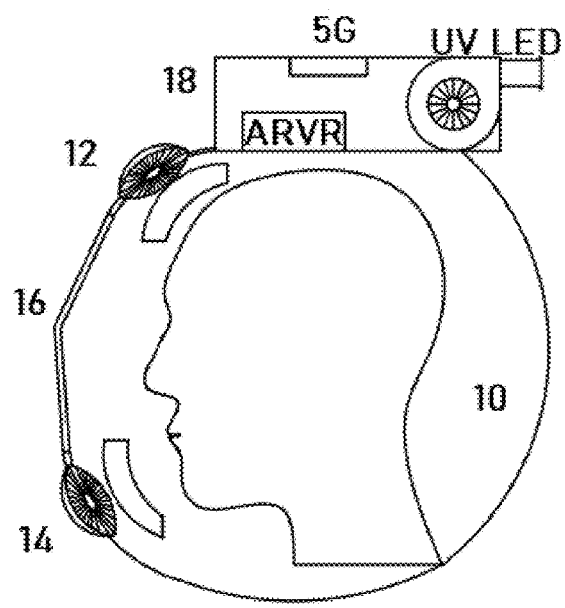
FIG. 3A
FIG. 3B
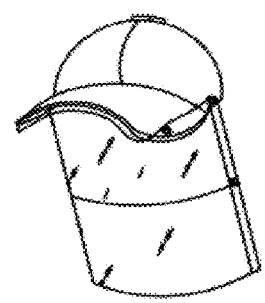
FIG. 3C
FIG. 3D
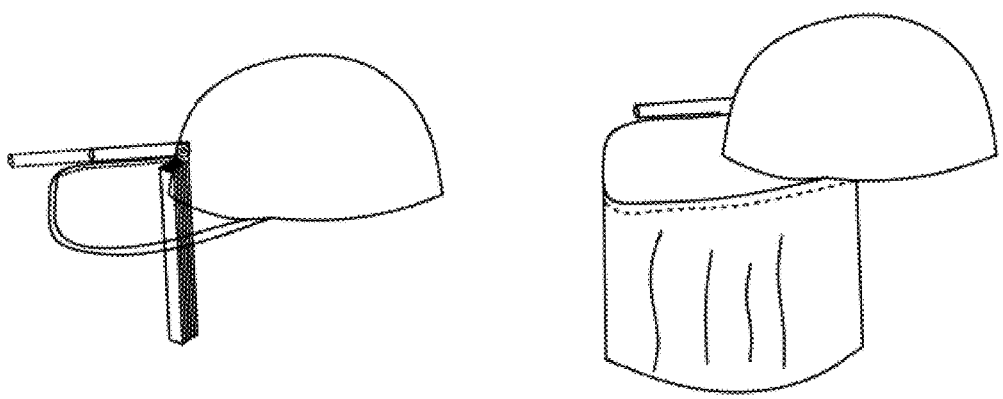

ROBOTIC MEDICAL SYSTEM

BACKGROUND

The present invention relates to medical robots.

Since Intuitive Surgical's da Vinci surgical robot arrival, there have been many other surgical robots introduced. Healthcare providers are now "digitizing" surgery by collecting and analyzing data passing through these robotic systems, such as in-motion tracking, capturing images, etc. This then allows for enhancements to the surgical processes. For example, U.S. Ser. No. 10/517,681B2 discloses a system and method for utilizing artificial intelligence to operate a surgical robot (e.g., to perform a laminectomy), including a surgical robot, an artificial intelligence guidance system, an image recognition system, an image recognition database, and a database of past procedures with sensor data, electronic medical records, and imaging data. The image recognition system may identify the tissue type present in the patient and if it is the desired tissue type, the AI guidance system may remove a layer of that tissue with the end effector on the surgical robot, and have the surgeon define the tissue type if the image recognition system identified the tissue as anything other than the desired tissue type.

In another trend, the COVID pandemic has significantly impacted our ability to travel on planes, ships, trains, public space such as parks and restaurants, and semi-private space such as offices and hotels. With over 3 billion airline passengers annually, the inflight transmission of infectious diseases is an important global health concern. Over a dozen cases of inflight transmission of serious infections have been documented, and air travel can serve as a conduit for the rapid spread of newly emerging infections and pandemics.

BRIEF SUMMARY

The embodiments of the invention are summarized by the claims that follow below.

BRIEF DESCRIPTION OF THE DRAWINGS

FIG. 1C shows exemplary processes to train a learning machine.

FIG. 1D shows exemplary neural network architectures to learn images for classification.

FIG. 2C shows an exemplary block diagram a device to protect and provide information to a traveler or a wearer.

FIGS. 3A-3D show exemplary embodiments of a cap-based traveler protection.

DETAILED DESCRIPTION

Figure 1A:
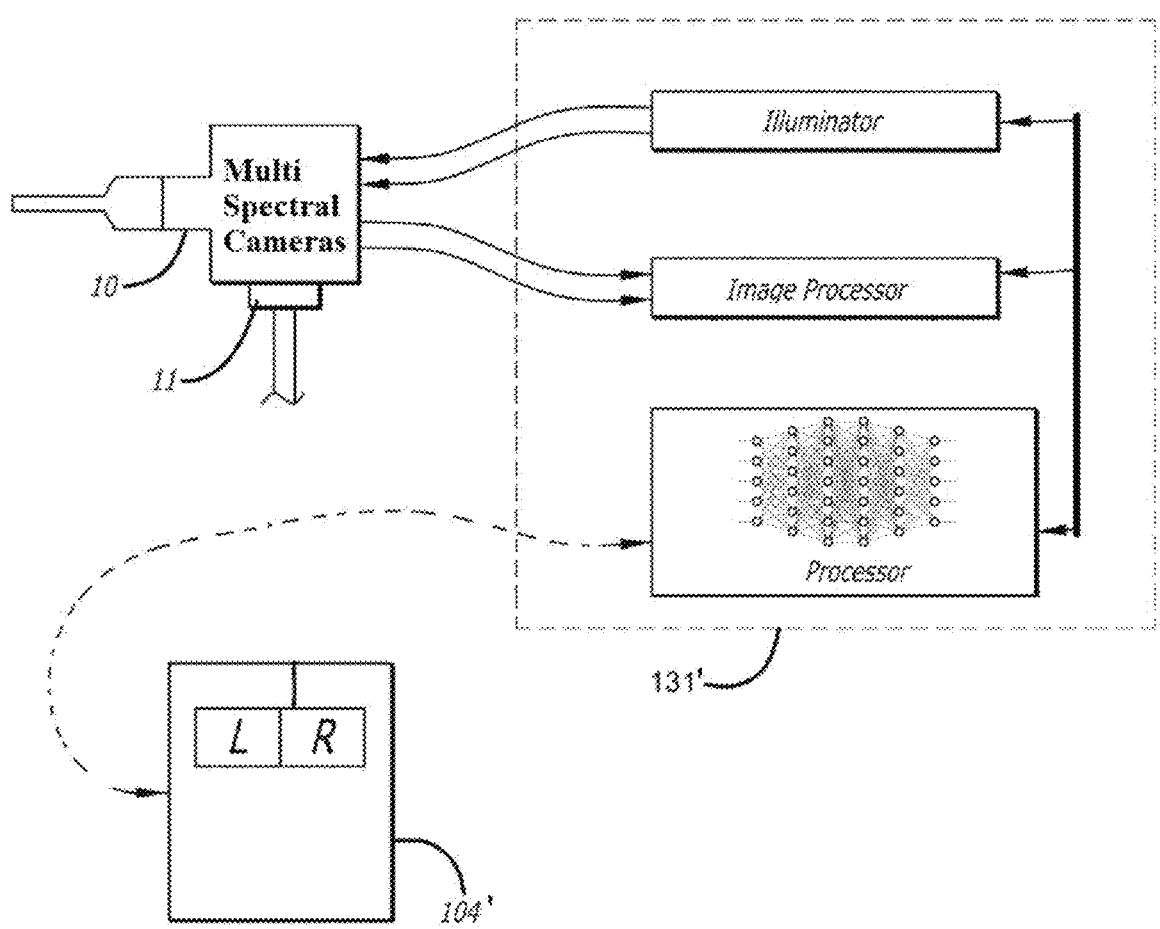
FIG. 1A is a block diagram of a mobile AI-based imaging system for minimally invasive surgery.

This detailed description describes exemplary implementations that are illustrative of the invention, and so is explanatory and not limiting. In the following detailed description of the embodiments of the invention, numerous specific details are set forth to provide a thorough understanding of the invention. However, the embodiments of the invention may be practiced without these specific details. In other instances well known methods, procedures, components, and circuits have not been described in detail so as not to unnecessarily obscure aspects of the embodiments of the invention. The invention is limited only by patented claims. In the drawings, some elements have been omitted to more clearly show the embodiments of the invention.

In one aspect, a system includes a camera, an AI visual processor to classify and recognize human anatomical features, and a processor to control robot movement to reach a selected anatomical target.

In another aspect, a mobile surgery system includes a camera, an AI visual processor to classify and recognize human anatomical features, and a processor to control robot movement to reach a selected anatomical target. The AI visual processor can detect symptoms of pandemic infections on a patient, such as lung lesions captured by body scanners. Implementations include scanners such as X-ray, UWB scanners, or ultrasound scanners. Implementations include active air masks for people in a confined space such as airplanes and ships and rail cars. Non-invasive vital sign sensors such as temperature, heart rate, oxygen level sensors, from smart wearable/smart watch devices can be used to predict a person's symptoms for infectious diseases. Phone based contact tracing apps can be used to further confirm a diagnosis of exposure to infectious diseases.

In yet another aspect, a system includes a camera, an AI visual processor to classify and recognize human anatomical features, and an interface receiving surgeon commands to control robot movement to reach a selected anatomical target, wherein the AI visual processor recommends actions to aid the surgeon.

In another aspect, a system includes a camera, an UWB transceiver providing anatomical scans to an AI processor to classify and recognize human anatomical features, and a processor to control robot movement to reach a selected anatomical target. In implementations, MIMO antennas are used with the UWB transceiver.

In another aspect, a system includes a camera, an MRI and UWB combination providing anatomical scans to an AI processor to classify and recognize human anatomical features, and a processor to control robot movement to reach a selected anatomical target. In implementations, the UWB devices can be used with MRI systems through MRI compatible antennas to avoid interference. Such MRI UWB combination enables the system to capture MRI with focused images of moving objects.

In yet another aspect, a system includes a camera, an AI visual processor to classify and recognize human anatomical features, an ablation device to provide a treatment, and a processor to control robot movement to reach a selected anatomical target and to deploy the ablation device to burn tissues on or proximal to the recognized anatomical features. The ablation device can be nuclear, temperature controlled (hot/cold) liquid, steam, resistive heater, or RF heater, among others.

In yet another aspect, a system includes a camera, an AI visual processor to classify and recognize cancer features, an ablation device to provide a treatment, and a processor to control robot movement to reach a selected anatomical target and to deploy the ablation device to destroy cancerous tissues on or proximal to the recognized anatomical features. The ablation device can be nuclear, temperature controlled (hot/cold) liquid, steam, resistive heater, or RF heater, among others.

In a further aspect, a system includes a camera, an AI visual processor to classify and recognize human anatomical features, an actuator to provide a treatment, and a processor to control robot movement to reach a selected anatomical target and to operate the actuator based on the recognized anatomical features. In embodiments where visualization of the surrounding tissue is made difficult, if not impossible, by medium contained within the lumen such as blood, an imaging hood may be advanced for placement against or adjacent to the tissue to be imaged. When deployed, the imaging hood may be expanded into any number of shapes, or may also define an atraumatic contact lip or edge for placement or abutment against the tissue region of interest. In one embodiment, a hood assembly can be positioned against a tissue region to be visualized and treated. Any number of energy modalities may be utilized for ablating the underlying tissue (such as RF, cryo, laser, HIFU or other forms of energy) through the lumen of the camera while under computer visualization. Alternatively, an energy delivery probe may be passed through the working channels of the camera or robot arm and brought in contact with the saline inside the hood to deliver RF ablation energy through the fluid.

In yet another aspect, a system includes a hyperspectral camera, an UWB transceiver providing anatomical scans to an AI processor to classify and recognize human anatomical features, and a processor to control robot movement to reach a selected anatomical target. Embodiments can use fiber Bragg grating (FBG) sensors coupled to the UWB transceiver to detect temperature, pressure, position, tilt, among others. Other sensors such as LIDAR camera, or imaging device can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to the robot tip, lumen, or other parts of the robot arm.

In yet another aspect, a system includes a LIDAR camera, an UWB transceiver providing anatomical scans to an AI processor to classify and recognize human anatomical features, and a processor to control robot movement to reach a selected anatomical target.

In another aspect, a system includes a high definition map of a human anatomy, a positioning system providing anatomical position to a processor to control robot movement to reach a selected anatomical target from the HD map and positioning system.

In yet another aspect, a system includes a high definition map of a standard human anatomy, an AI processor to classify and recognize patient anatomical features to update the HD map with personally identifiable changes to the standard human anatomy to arrive at a patient HD map, a positioning system providing anatomical position to a processor to control robot movement to reach a selected anatomical target from the patient HD map and positioning system.

In yet another aspect, a system includes a high definition map of a standard human anatomy downloaded from a remote database, an AI processor to classify and recognize patient anatomical features to update the HD map with personally identifiable changes stored in a separate data layer to arrive at a patient HD map from the standard human anatomy, and a positioning system providing anatomical position to a processor to control robot movement to reach a selected anatomical target from the patient HD map and positioning system.

In a further aspect, a system includes a high definition map of a human anatomy, a positioning system providing anatomical position, an AI processor to classify and recognize human anatomical features, and a processor to control robot movement to reach a selected anatomical target from the HD map and positioning system based on AI processing. Embodiments can make an incision based on the HD map, or alternatively to avoid cutting/making an incision, can route a wire through a patient body orifice to the target based on the HD map. Other embodiments can deploy a treatment device to apply nuclear, temperature controlled (hot/cold) liquid, steam, resistive heater, or RF heater, among others. Yet other embodiments can collect specimens for subsequent analysis at the determined patient position.

In a further aspect, a system includes a high definition map of a human anatomy, a positioning system providing anatomical position, a camera with an AI processor to classify camera images and recognize human anatomical features, and a processor to control robot movement to reach a selected anatomical target from the HD map and positioning system based on AI processing. Embodiments can make an incision based on the HD map, or alternatively to avoid cutting/making an incision, can route a wire through a patient body orifice to the target based on the HD map. Other embodiments can deploy a treatment device to apply nuclear, temperature controlled (hot/cold) liquid, steam, resistive heater, or RF heater, among others. Yet other embodiments can collect specimens for subsequent analysis at the determined patient position.

In a further aspect, a system includes an injectible or ingestible pill or module that autonomously navigates to an anatomical target with data from high definition map of a human anatomy and deliver a treatment. The pill or module receives positioning data from a positioning system providing anatomical position. To aid navigation and treatment delivery, the pill/module includes a camera with an AI processor to classify camera images and recognize human anatomical features, and a processor to control pill/module movement to reach a selected anatomical target from the HD map and positioning system based on AI processing. Embodiments can deploy a treatment device to apply nuclear, temperature controlled (hot/cold) liquid, steam, resistive heater, or RF heater, among others. Other embodiments can scan the target with visual, multi-spectral, or HS scans of the target for subsequent treatment. Yet other embodiments can collect specimens for subsequent analysis at the determined patient position.

In another aspect, a pill or a treatment device can release beneficial microbes into selected regions such as the gut or intestine, for example. The treatment device can release a therapeutically-effective amount of a pharmaceutical composition comprising a population of isolated and purified microbe and a pharmaceutically-acceptable carrier. Such microbe alters glucagon-like peptide-1 (GLP-1) production. The microbes can be a microbe that encodes for an enzyme selected from the group consisting of: butyrate kinase, butyrate coenzyme A, butyrate coenzyme a transferase, and any combination thereof, and a pharmaceutically-acceptable carrier.

In a further aspect, a system includes a guided optical fiber that autonomously navigates to an anatomical target with data from high definition map of a human anatomy and deliver a treatment. The fiber receives positioning data from a positioning system providing anatomical position. To aid navigation and treatment delivery, the fiber includes a camera with an AI processor to classify camera images and recognize human anatomical features, and a processor to control robot movement to reach a selected anatomical target from the HD map and positioning system based on AI processing. Embodiments can deploy a treatment device to apply nuclear, temperature controlled (hot/cold) liquid, steam, resistive heater, or RF heater, among others. Other embodiments can scan the target with visual, multi-spectral, or HS scans of the target for subsequent treatment. Yet other embodiments can collect specimens for subsequent analysis at the determined patient position. Other embodiment uses as sensors a fiber Bragg grating (FBG) to determine pressure, temperature, tilt, position, among others.

Implementations of any of the above aspects may include one or more of the following: the system includes robotic arms with replaceable end effectors for specific surgery work, the robotic arms can autonomously navigate to anatomical targets for surgery using a combination of HD anatomical maps, positioning feedback, and fixed markers for references, the system can render AR/VR/XR displays for a doctor to view; the system can align its position relative to known markers on the patient to improve its position determination; the camera can be a multispectral or hyperspectral camera; the camera can have optical filters mounted on rotatable wheels whose movements are controlled by the processor; sensors such as fiber Bragg grating (FBG) sensors can be coupled to the UWB transceiver to detect temperature, pressure, position, tilt, among others.

Yet other implementations of any of the above aspects may include one or more of the following.

Robotic Surgery Systems with AI Autonomy and Partial Autonomy

Referring now to FIG. 1A-1D, block diagrams of a surgical system 100 for minimally invasive surgery, among others, are illustrated. The system includes an AI based vision system with a body cavity camera 10 with suitable illuminator(s), image processors, and AI control in a vision module 131' which operates autonomously and/or collaboratively with a surgeon via a surgeon console 104.

Figure 1B:
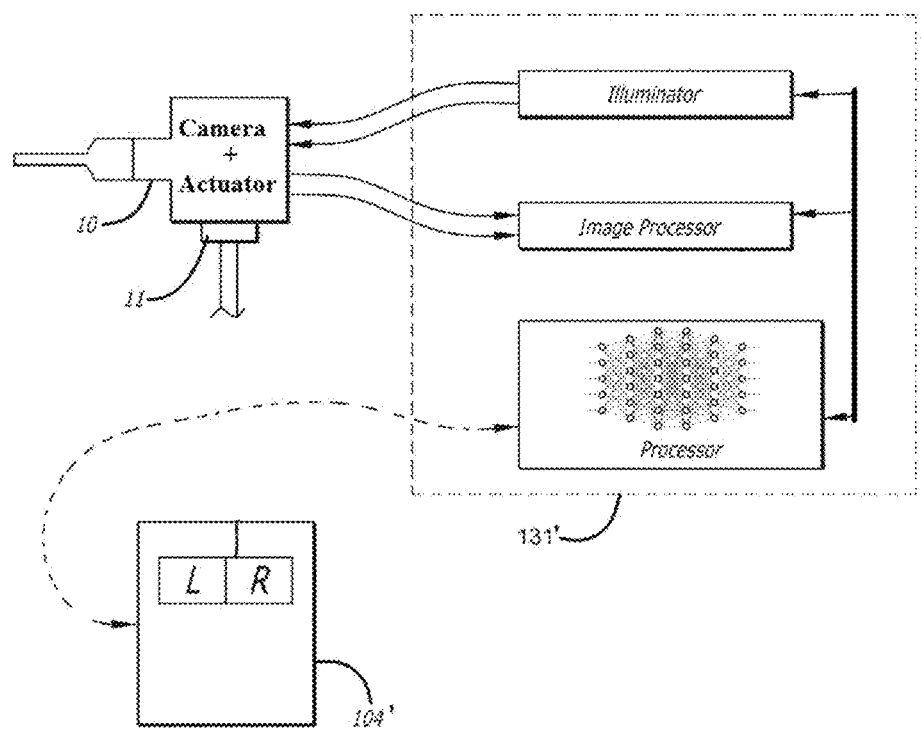
FIG. 1B shows alternative embodiments with different actuators with the AI-based imaging system for minimally invasive surgery.
Figure 1B:
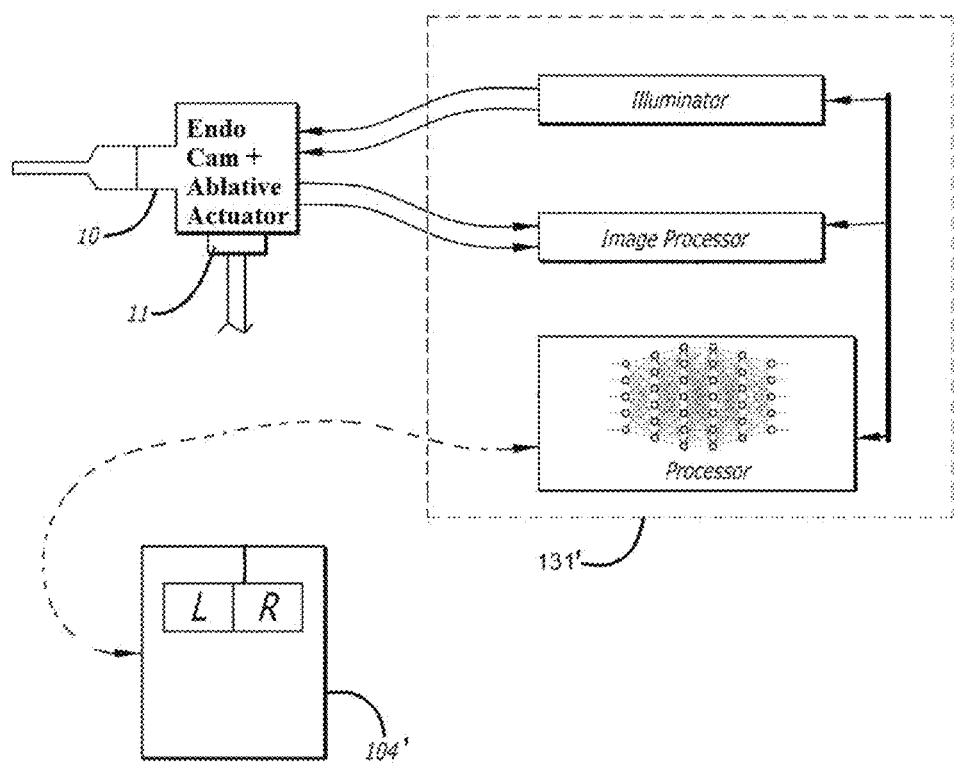

FIG. 1A shows an effector embodiment with cameras only, while FIG. 1B shows a camera and actuator effector combination and FIG. 1C shows an endoscopic camera and ablative unit that can cauterize/burn tissue for various operations including endometrial treatment, gastric surgery, obesity treatment, and cancer treatment by burning cancerous regions, for example. The systems can also capture specimens for subsequent analysis, such as cancer tissues, for example. The camera(s) can be used to generate a 3D model of the body internals as the camera(s) traverse the body. The 3D model is then used to compare with prior 3D mapping of the patient using X-ray or ultrasound, among others. Additionally, the units in FIGS. 1A-1C can include RF transceivers such as ultra-wide-band (UWB) transceivers that transmit at gigahertz or terahertz range to create body mapping data. The 3D positioning data from the camera(s) or UWB transceivers can be aligned with body markers X or Y on the patient to increase the accuracy of the position determination of the robotic arm. The system can accommodate data in various formats, including medical reality markup language (MRML), DICOM and clinical PACS. The image recognition database is populated by images taken by the surgical robot cameras that are defined by the surgeons and updated with each use of the system for greater accuracy. The surgeon controls are used for manual manipulation of the surgical robot, either to take over when the AI cannot proceed or to navigate the end effector to the point of interest. The procedure database can include medical records data, images (e.g., pre- and post-surgical images), physician input, sensor data, or the like. The images can include MRI or CAT scans, fluoroscopic images, or other types of images. The sensor data can be collected during procedures, etc. related to all procedures of this type. This database is queried by the surgical control for all medical imaging from the current patient and by the progression module for data for all similar patients who had the same procedure.

In embodiments where visualization of the surrounding tissue is made difficult, if not impossible, by medium contained within the lumen such as blood or excrement, an imaging hood may be advanced for placement against or adjacent to the tissue to be imaged. When deployed, the imaging hood may be expanded into any number of shapes, e.g., cylindrical, conical, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control. In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

Various embodiments are aimed at improving the clinical utility of AI vision processing to assist surgery of a surgical with, the simultaneous display of a reflected white light image of tissue, and a separately or simultaneously acquired enhanced image of tissue in the same surgical site. The AI vision machine operates on enhanced image of tissue may be captured with technologies such as, but not limited to, near-infrared (NIR) fluorescence, visible light fluorescence, multispectral imaging, fluorescence lifetime imaging, or a raster scan of non-visible light characteristics that contains clinical information with spatial variation. In addition, the enhanced image may be of an image constructed by overlaying point measurements of different types of measurable tissue parameters such as tissue impedance, point detection of cancer, or certain cell types on the clinical white light image.

One embodiment uses as sensors a fiber Bragg grating (FBG) which is a microstructure within the core of an optical fiber comprising a periodic modulation of the refractive index of the underlying glass material. If broadband light guided within the core hits on this periodic micro-structure one specific wavelength gets reflected and all other wavelengths of the guided broadband light can pass unhindered. The periodicity of the FBG defines which specific wavelength gets reflected and is perpetually inscribed into the glass like a spectral fingerprint. Only if an external force or change in temperature is induced to the microstructure, the periodicity of the FBG will change slightly leading to a specific wavelength shift of the light reflected at the FBG. The FBG is a type of distributed Bragg reflector constructed in a short segment of optical fiber that reflects particular wavelengths of light and transmits all others. This is achieved by creating a periodic variation in the refractive index of the fiber core, which generates a wavelength-specific dielectric mirror. Hence a fiber Bragg grating can be used as an inline optical fiber to block certain wavelengths or it can be used as wavelength-specific reflector. Fiber Bragg gratings are created by "inscribing" or "writing" systematic (periodic or aperiodic) variation of refractive index into the core of a special type of optical fiber using an intense ultraviolet (UV) source such as a UV laser. Two main processes are used: interference and masking. The method that is preferable depends on the type of grating to be manufactured. Normally a germanium-doped silica fiber is used in the manufacture of fiber Bragg gratings. The germanium-doped fiber is photosensitive, which means that the refractive index of the core changes with exposure to UV light. The amount of the change depends on the intensity and duration of the exposure as well as the photosensitivity of the fiber. To write a high reflectivity fiber Bragg grating directly in the fiber the level of doping with germanium needs to be high. However, standard fibers can be used if the photosensitivity is enhanced by pre-soaking the fiber in hydrogen. Fiber Bragg gratings can also be written in polymer fibers. A number of FBG sensors can be formed on the fiber, including temperature compensated linear position measurement, strain measurement, temperature, pressure, acceleration, and tilt as part of a measurement chain, among others. FBG can provide hundreds of sensors on the gratings.

Other sensors such as bioimpedance, inductive, and capacitance sensors can be used to analyze objects, while the camera can visually determine the body parts that the robot arm is passing through as well as the target body part to navigate to.

The camera 10 can be a high-resolution (such as 8k) video camera, a multi-spectral camera, an HSI camera, or any combination thereof. For multi-spectral operation, optical filters on rotatable wheels can selected predetermined spectral wavelength to capture images. For calibration, the system can capture images of a reference color (such as white) and the image value of certain pixels are compared to the reference color value and the color value can be adjusted to calibrate the color. The adjustment can include the exposure period to increase the color value, for example. This process is repeated for each wavelength in the multi-spectral camera until each wavelength is calibrated.

In one embodiment, hyperspectral imaging (HSI) can collect required spectral information from each spatial pixel in a region of interest (ROI). As a hyperspectral (HS) imager, the system can capture at least 100-200 images at different wavelengths versus the multispectral imaging which captures at most few tens of wavelength bands. The HIS system can do spatial-scanning, spectral-scanning or snapshot methods. Reflectance intensity mappings of appropriate wavelengths can be selected to spectrally distinguish one region from another for diagnostic applications. Autofluorescence occurs when endogenous fluorophores are excited by a laser having an appropriate excitation wavelength and the magnitude of autofluorescence variations is dependent on the tumor stage since the differences become greater as the tumor progresses. Therefore, detection and staging of tumor can be done using fluorescence imaging to capture the autofluorescence in tissues by looking out for changes in the fluorescence intensity.

In FIG. 1A, the vision module 131' (part of a suite of tools 131 available to a robot) is detailed. The system includes a body cavity camera subsystem 10 that includes a mechanical interface to detachably couple to a robotic arm 11 of a patient side manipulator so that it may be moved around within a surgical site of a patient. The body cavity camera 10 is supported by the robotic arm 11 over a surgical site within a body cavity of a patient to capture digital images therein. The vision module can be one item in a range of effectors. The effectors can be installed in the robotic system and can include, without limitation, robotic grippers, cutting instruments (e.g., cutters, scalpels, or the like), drills, cannulas, reamers, rongeurs, scissors, clamps, or the like. The number and configuration of end effectors can be selected based on the configuration of the robotic system and the procedure to be performed. The AI system can select end effectors to perform one or more the steps in a surgical procedure.

As an effector or built-in part of the robot arm, the vision module 131' includes an illuminator, an image processor, an AI vision processor 16, and optionally an AR/VR/XR (augmented/virtual/extended reality) monitor 104' or alternatively can be a conventional monitor 104. The body cavity camera 10 is coupled to the illuminator to receive visible/invisible light and direct it out of its tip into a surgical site to illuminate tissue for capture with a multi-spectral or HS camera in addition to a high-resolution visual camera. The body cavity camera 10 may also be coupled to the illuminator to receive multi-spectral (visible/invisible) EM radiation and direct it out of its tip into the surgical site to excite a material to fluoresce tissue for capture with a sensor or multispectral camera. The body cavity camera 10 captures one or more frames of a color visible image of tissue within the surgical site in response to the visible light and couples them into the image processor. The body cavity camera 10 may further capture one or more frames of non-visible spatially encoded data from the tissue within the surgical site in response to the multi-spectral (visible/invisible) EM radiation and couple the data into the image processor. The body cavity camera can be is a stereo camera for concurrently capturing left and right images of the surgical site, and such stereo image can be used to reconstruct a 3D model of the internals of the patient while the camera 10 moves inside the patient. While the body cavity camera 10 and its sensors may be used to capture optical non-visible images (e.g., near infrared, ultraviolet), other imaging devices and techniques may be used to capture other non-visible spectrum data, such as but not limited to, spectroscopic data, Raman scattering values, impedance data, two-photon fluorescence, ultrasound, gamma radiation and/or X-ray images whose data may be represented as an image in the visible spectrum and combined with the desaturated image. Additionally, light may be captured which covers all or a portion of the entire image and analyzed to create clinically relevant two dimensional (2D) images. These 2D images may capture features extracted from light properties such as polarization, scattering, and other similar characteristics related to the interaction of light and tissue where the tissue may be augmented by various clinically relevant markers. The enhanced image may be an image which has been computed for a series of visible images. For example, a series of images may be used to compute blood flow which can then be represented as a 2D image.

The camera 10 can include a plurality of bandpass filters mounted on rotatable crystals in front of the optics that let radiation through at predetermined wavelength and reject the rest. One embodiment uses rotating wheels that allow a variety of bandpass filters. The wheel is rotated by a motor to a desired filter location, and the camera can take images as illuminated by the illuminator which provides illumination for the selected wavelength.

The illuminator may generate the visible light, a light generated in the visible electromagnetic radiation spectrum, and the multi-spectral (visible/invisible) electromagnetic or EM radiation in response to control signals that may be received from the AI processor. The illuminator may generate the visible light and the multi-spectral (visible/invisible) EM radiation concurrently to capture frames of the color visible images in synch with capturing the non-visible spectrum data and forming frames of enhanced images in response to the control signals. Alternatively, the illuminator may alternate the generation of the visible light and the multi-spectral (visible/invisible) EM radiation to capture frames of the color visible images out of synch with capturing the non-visible spectrum data and forming frames of enhanced images in response to the control signals.

Characteristic tissue features not visible with reflected white light, may also be tagged and illuminated by electromagnetic radiation outside the visible EM spectrum in the lower or upper non-visible portions of the electromagnetic radiation spectrum that unaided human eyes can't perceive. The lower and upper non-visible portions of the electromagnetic radiation spectrum reside outside the visible portion of the electromagnetic radiation spectrum. The upper non-visible portion of the electromagnetic radiation spectrum ranges from approximately 400 nano-meters (nm) to one tenth of an angstrom (A) in wavelength including gamma-rays, x-rays, and ultraviolet electromagnetic radiation. The lower non-visible portion of the electromagnetic radiation spectrum ranges from approximately 600 nano-meters (nm) to ten meters (m) in wavelength including infrared (near infrared, thermal infrared, far infrared), microwaves, and radio waves. Near infrared EM radiation, with a wavelength range approximately between 600 nm to 1200 nm, may be preferable in some cases as many biological tissues are more transparent at these wavelengths than in the visible spectrum so that tissue features or structures below the surface that are tagged with a biomarker may be more readily imaged. The visible light and the multi-spectral (visible/invisible) EM radiation may be coupled into the body cavity camera 10 by one or more optical fibers or bundles of optical fibers. Similarly, the full color visible images of visible tissue captured within the surgical site and coupled into the image processor via an optical fiber or captured by a sensor and coupled into the image processor by a wire cable. The non-visible spectrum data of the tissue within the surgical site may also be coupled into the image processor via an optical fiber or captured by a sensor and coupled into the image processor by a wire cable. Electromagnetic radiation captured by one or more sensors may be binned out into the visible red, green, blue EM spectrum and the non-visible EM spectrum (e.g., near-infra-red).

The image processor stores image data in memory and processes video data. The image processor can include specialized edge detectors and parallel pipelines to process stereo images in parallel if needed. The image processor can run digital signal processing or image processing routines as needed to perform the pixel manipulation of each frame of digital image data to perform the image processing and display methods disclosed herein.

The number of surgical tools used at one time and consequently, the number of slave arms being used in the system 100 will generally depend on the diagnostic or surgical procedure and the space constraints within the operating room, among other factors. If it is necessary to change one or more of the tools being used during a procedure, the tool no longer being used can be moved from its slave arm, and replace it with another tool, such as a minimally invasive surgical tool 131, from a tray ("T") in the operating room.

The surgeon console 104 may be coupled to the AI processor over a 5G or 6G cellular connection 110 a fiber optic cable for high-speed communication of digital control and image information. The surgeon console 104 may include a stereo display device 140 to display left and right stereo images to the surgeon. The stereo display device 140 may display left and right blended images in accordance with the display method disclosed herein.

The robot can have actuators near the cameras as in FIG. 1B. The actuators can be motorized, pneumatic, or guided wires moved by a remote robot arm or human hand. The actuators can squeeze, cut, burn, roll, expand, or perform a number of mechanical operations on the patient. The robot can create guide wires that have different, adjustable 2D shapes. This will allow the surgeon to pick the most applicable shape to use for different procedures or at a specific point in a procedure. The shapes can also be produced through the combining of different guide wires. Guidewire shape would be determined by AI using correlations between patient attributes, procedure type, wire shape, and postoperative outcomes. The guide wire can comprise one or more needles, each of the needles may have a distal portion, as illustrated in ablation tip detail, which comprises a plurality of exposed electrodes at or proximal to the needle tips. As the needle assembly is introduced into the tissue while under visualization with camera 140, energy may be conducted between the exposed electrodes to ablate the tissue surrounding the needles. The flow of current between the electrodes can result in isolated resistive heating at the specific subsurface tissue region.

As shown in FIG. 1C, in treating tissue regions which are visually recognized by AI processors, treatments utilizing hot/cold liquid/gas/water, nuclear isotope pods, electrical heater, radio-frequency (RF), or electrical energy may be employed to ablate the underlying visualized tissue. Bipolar configuration can be used, or monopolar configuration can be used where a single electrode is positioned proximate to or directly against the tissue to be treated within the patient body and a return electrode is located external to the patient body. Utilization of bipolar electrode ablation removes the need for a return or grounding electrode to be adhered to the skin of the patient and may further allow for a more precise delivery of ablation energy over a small target area for creation of precise lesions. A pump can introduce cooling fluids or remove fluids post-surgery on electrical command. In one configuration, saline solution in separate chambers can be used as conductive electrodes for the RF ablation for either mono or bipolar configurations.

In particular, such assemblies, apparatus, and methods may be utilized for treatment of various conditions, e.g., cancer, gastric reduction, arrhythmias, through surgical operations under computer visualization. The operation can involve removal of tissues, joining of tissues, opening of holes, closure of holes through ablation, among others. Variations of the tissue imaging and manipulation apparatus may be configured to facilitate the application of bipolar energy delivery, such as resistive wires or RF ablation, to an underlying target tissue for treatment in a controlled manner while visualizing via AI vision the tissue during the ablation process as well as confirming (visually, sensor detections, and otherwise) appropriate treatment thereafter.

Figure 1E:
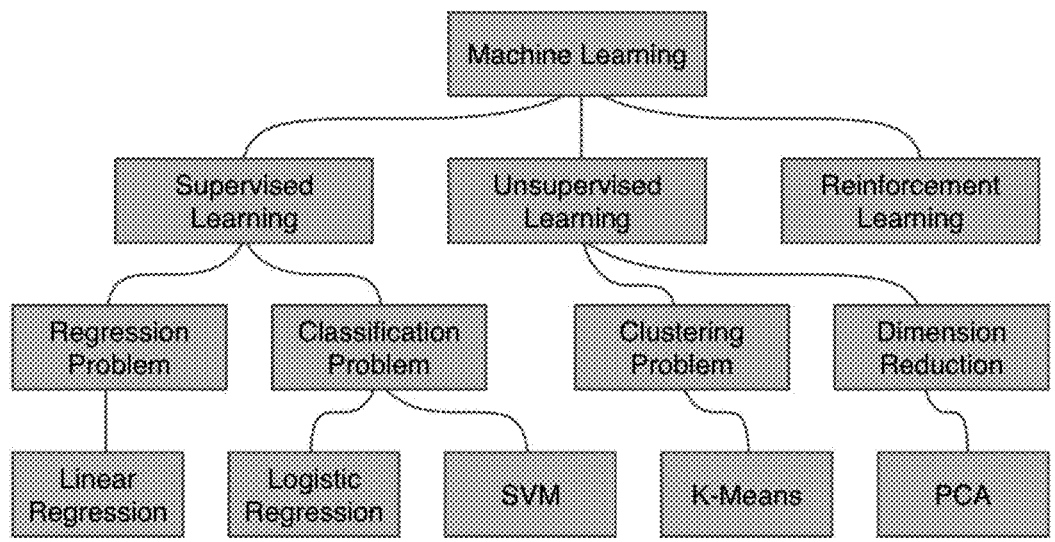
FIG. 1E shows exemplary AI architectures for image recognition of body objects/landmarks and control of the surgery robot.
Figure 1E:
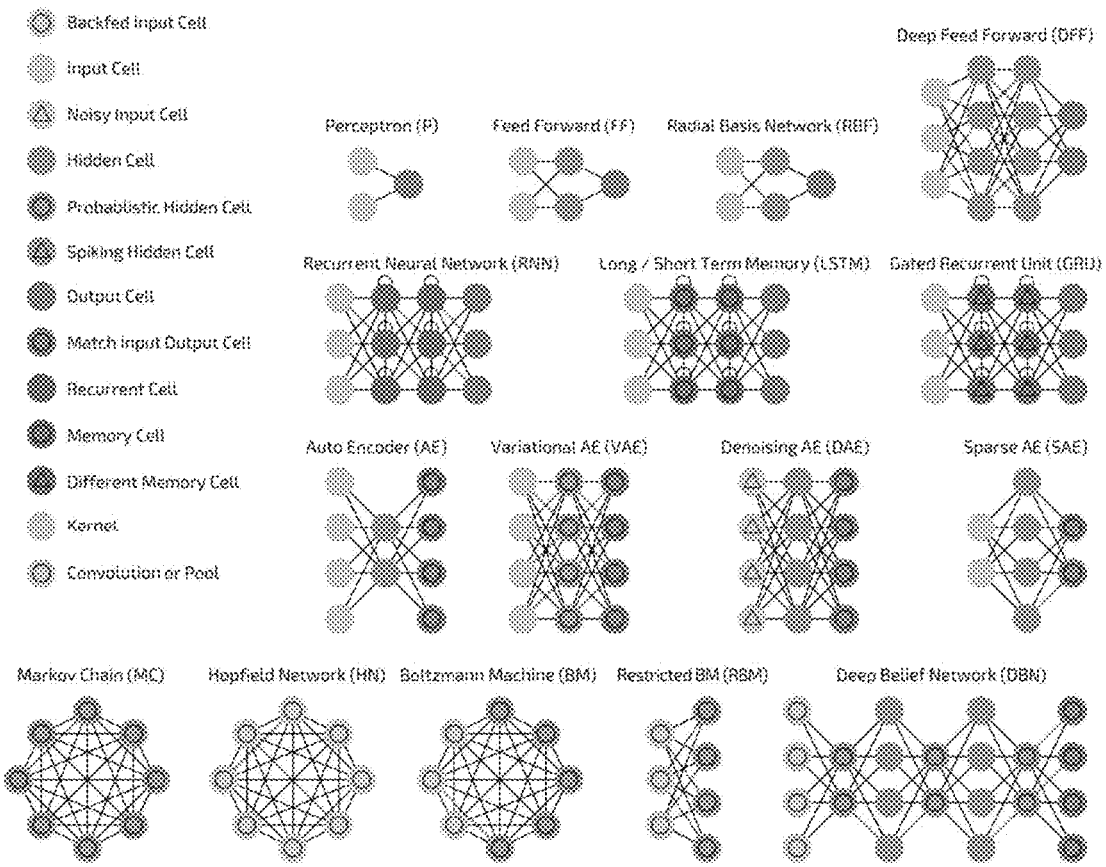

FIG. 1C shows exemplary processes to train and then deploy deep learning machines to learn images for classification while FIG. 1D shows exemplary neural network architectures for controlling robot movements and actuators. FIG. 1E shows exemplary AI architectures for image recognition of body objects/landmarks and control of the surgery robot. One embodiment uses the GPT, BERT, and Transformer architectures with a token bias. The GPT-2 is built using transformer decoder blocks. The model is constructed using the basic concept of Transformer, Attention, etc, for pre-training a dataset composed of Common Crawl, Wikipedia, WebText, Books and some additional data sources. The GPT-3 language model has 175 billion parameters. A parameter is a measurement in a neural network that deploys a large or small weightage to a few aspects of data, for providing that aspect larger or smaller importance in an entire measurement of the data. These are the weights that deliver shape to the data, and provide a neural network an understanding angle on the data. GPT-3 involves adjusted initialization, pre-normalization, and changeable tokenization. It reflects substantial performance on various NLP tasks and benchmarks in three distinct shots, i.e. zero-shot, one-shot and some-shot environments. BERT, on the other hand, uses transformer encoder blocks. One difference between the two is that GPT2, like traditional language models, outputs one token at a time, the model to predict the next token in a sequence, rather than converting one sequence to another functionally identical one. The output layer is modified to reflect the probability biasing. These models predict the next token in a sequence, rather than converting one sequence to another functionally identical one, and the output layer uses probability biasing discussed above.

For position information, a positional embedding is added to each word embedding using sine and cosine functions to form a continuous binary encoding of positions in a sequence. Mulltihead attention is used to encode the input embeddings where input order in the sequence is lost so positional embeddings are used. As is known to one skilled in the art, the transformer uses the encoder attention, the encoder-decoder attention and the decoder attention. The attention mechanism is implemented as a vector multiplication, where the angle of the vector can determine the importance of each value. If the angles of the vectors are close to 90 degrees, then the dot product will be close to zero, but if the vectors point to the same direction, the dot product will return a greater value. Each key has a value associated, and for every new input vector, we can determine how much does this vector relates to the value vectors, and select the closest term using a softmax function. Transformers have a multihead attention; similar to filters in CNN's, each one learns to pay attention to a specific group of words. One can learn to identify short-range dependencies while others learn to identify long-range dependencies. The model to predict the next token in a sequence, rather than converting one sequence to another functionally identical one. There would also be some changes made to output layer (probability biasing). This improves the context-awareness to help the model determine the terms referred to when it's not clear; for example, with words such as pronouns.

The Encoder and Decoder are composed of modules that can be stacked on top of each other multiple times and the modules consist mainly of Multi-Head Attention and Feed Forward layers. The inputs and outputs (target sentences) are first embedded into an n-dimensional space since strings are not used directly. The positional encoding of the different words are added to the embedded representation (n-dimensional vector) of each word. One commonly used attention calculation can be:

$$\text{Attention}(Q, K, V) = \text{softmax}\left(\frac{QK^T}{\sqrt{d_k}}\right)V$$

where Q is a matrix that contains the query (vector representation of one word in the sequence), K are all the keys (vector representations of all the words in the sequence) and V are the values, which are again the vector representations of all the words in the sequence. For the encoder and decoder, multi-head attention modules, V consists of the same word sequence than Q. However, for the attention module that is considering the encoder and the decoder sequences, V is different from the sequence represented by Q. To simplify, the values in V are multiplied and summed with attention-weights a, defined by:

$$a = \text{softmax}\left(\frac{QK^T}{\sqrt{d_k}}\right)$$

Weights a are defined by how each word of the sequence (represented by Q) is influenced by all the other words in the sequence (represented by K). Additionally, the SoftMax function is applied to the weights a to have a distribution between 0 and 1. Those weights are then applied to all the words in the sequence that are introduced in V (same vectors than Q for encoder and decoder but different for the module that has encoder and decoder inputs).

The attention-mechanism can be parallelized into multiple modules and is repeated multiple times with linear projections of Q, K and V. This allows the system to learn from different representations of Q, K and V. These linear representations are done by multiplying Q, K and V by weight matrices W that are learned during the training. Those matrices Q, K and V are different for each position of the attention modules in the structure depending on whether they are in the encoder, decoder or in-between encoder and decoder. The reason is that we want to attend on either the whole encoder input sequence or a part of the decoder input sequence. The multi-head attention module that connects the encoder and decoder will make sure that the encoder input-sequence is considered together with the decoder input-sequence up to a given position. After the multi-attention heads in both the encoder and decoder, the transformer has a pointwise feed-forward layer. This feed-forward network has identical parameters for each position, which can be described as a separate, identical linear transformation of each element from the given sequence.

While the system uses a standard transformer as described above, the process applies the above commonly used transformer architecture and tunes the training for long text generation that is guided by an outline so that the long form text is useful. This combines increased model size while sacrificing convergence by stopping training early. As larger models converge to lower test error in fewer gradient updates than smaller models, large models achieve higher accuracy faster for training and speed during inference is achieved using model compression. In the instant process, large models are used on large text clustered into specific groups or technology or market segments, or IPC code, for example. The output probabilities are biased according to a customization indicium data (for example the IPC mentioned above). Such training creates custom models for each context based on the output probabilities as biased. One embodiment uses quantization and pruning to reduce the inference latency and memory requirements of storing model weights. Quantization stores model weights in low precision and pruning sets predetermined NN weights to zero.

During inference, the process includes:
Input the full encoder sequence (a short phrase) and as decoder input, an empty sequence is used with only a start-of-sentence token on the first position. This will output a sequence with the first element.
That element will be filled into second position of the decoder input sequence, which now has a start-of-sentence token and a first word/character in it.
Input both the encoder sequence and the new decoder sequence into the model with the biased output probability incorporating the context sensitive data. Take the second element of the output and put it into the decoder input sequence.
Repeat this until done.

One embodiment predicts an end-of-sentence token, which marks the end of the phrase expansion into a sentence, paragraph, or long form text, among others.

Multiple runs through the model are used for the text expansion process.

The models can have different parameters of the Transformer, such as the number of decoder and encoder layers, and the results can be tuned and trained with large corpus for improving output.

In another embodiment for video inferencing, the process is trained on predicting an image (or brief video) and generating a longer video sequence. The process includes:
Input the full encoder sequence (a short phrase or starting image/video) and as decoder input, an empty sequence is used with only a start-of-video token on the first position. This will output a sequence with the first element.
That element will be filled into second position of the decoder input sequence, which now has a start-of-video token and a first image in it.
Input both the encoder sequence and the new decoder sequence into the model (optionally with the biased output probability incorporating the context sensitive data in another embodiment). Take the second element of the output and put it into the decoder input sequence.
Repeat this until done.

Multiple runs through the model are used for the video expansion process.

One embodiment generates videos from a milestone image. They can use transformers, GANs, and VAEs, or combinations thereof. One embodiment uses Generative Adversarial Network (GAN), a framework for training generative models in an adversarial setup with two networks, a generator that creates object instances (e.g., images, sentences) and tries to fool a discriminator; and a discriminator is trained to discriminate between real and synthetic object instances.

Figure 4A:
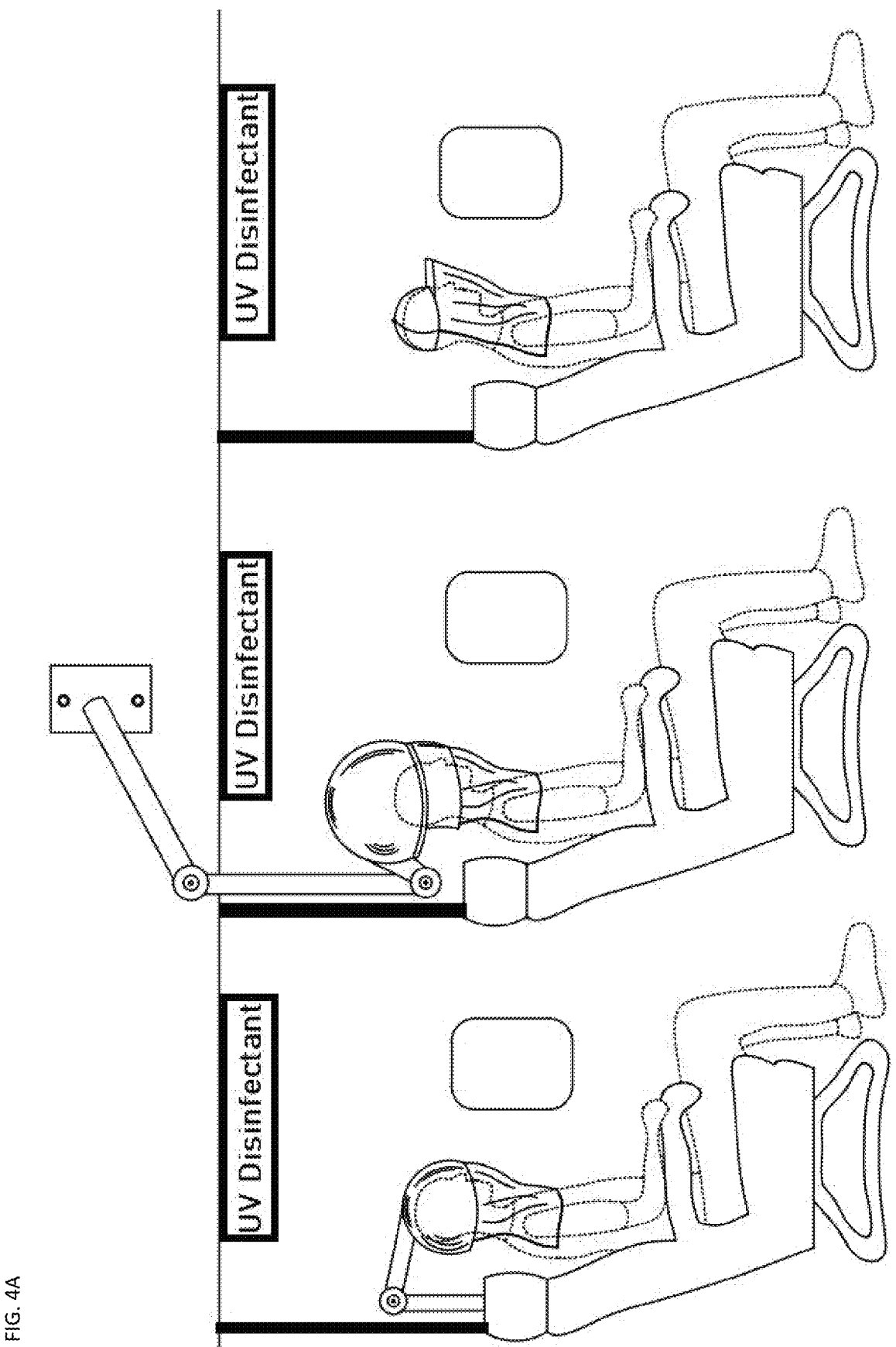
FIGS. 4A-4H show exemplary embodiments of cabin-based protection and display of information to a traveler.
Figure 4B:
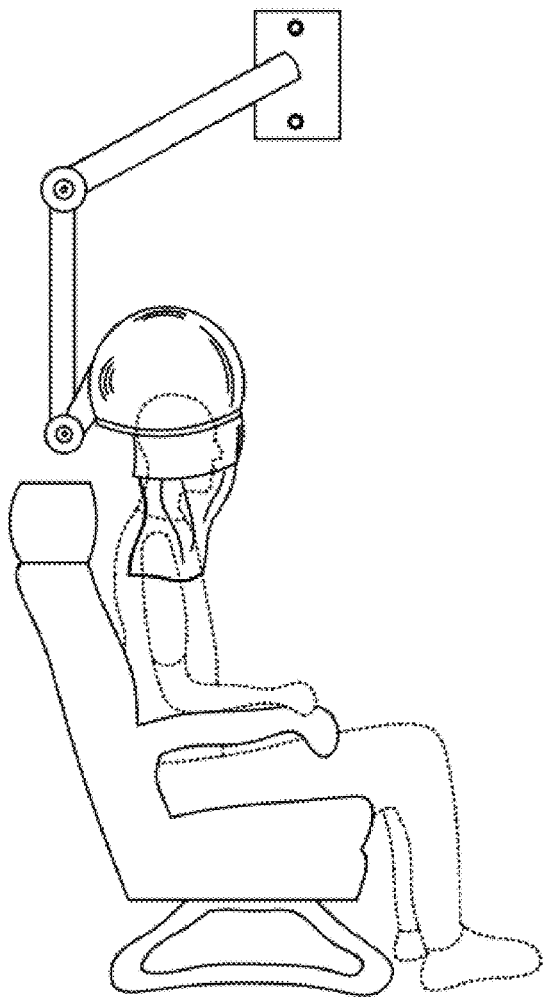
Figure 4C:
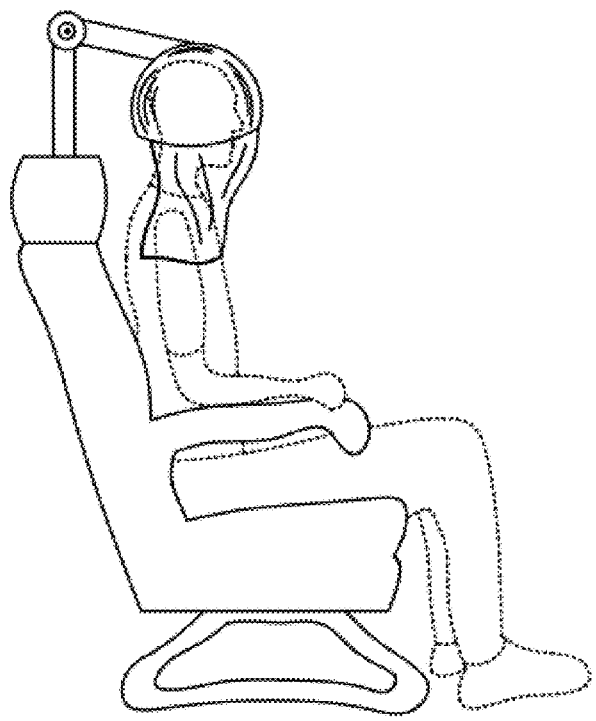
Figure 4D:
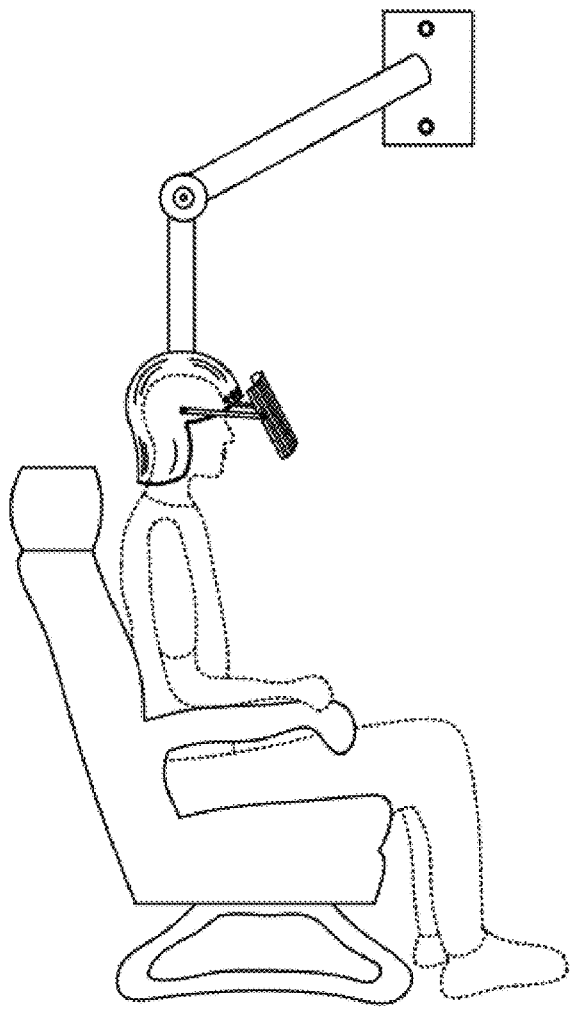
Figure 4E:
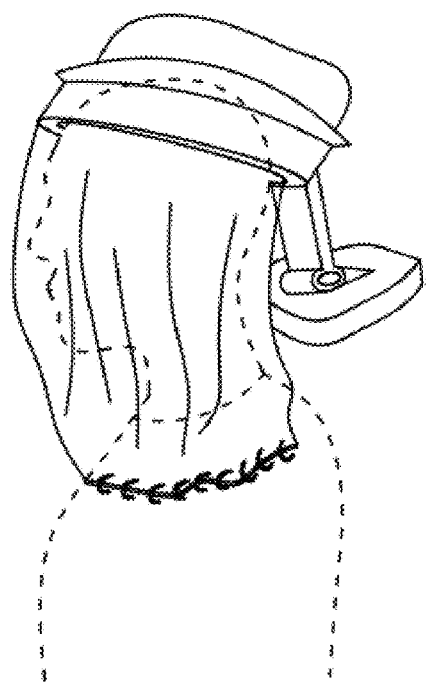
Figure 4F:
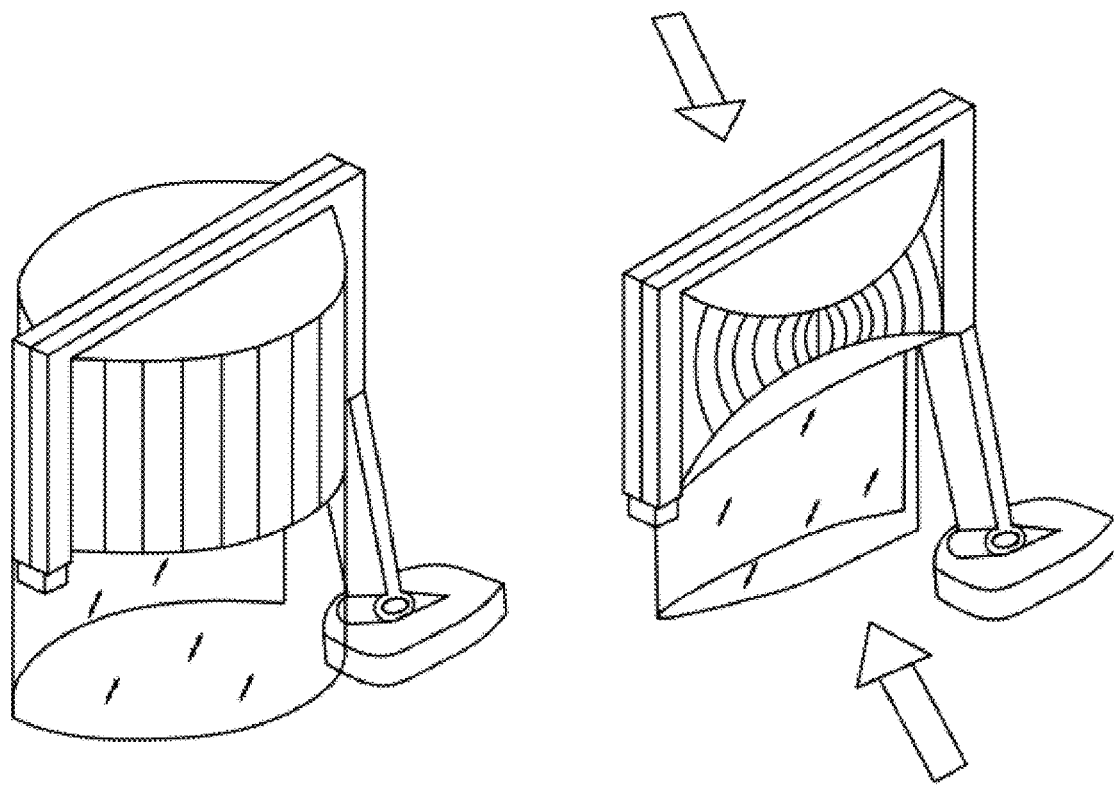
Figure 4G:
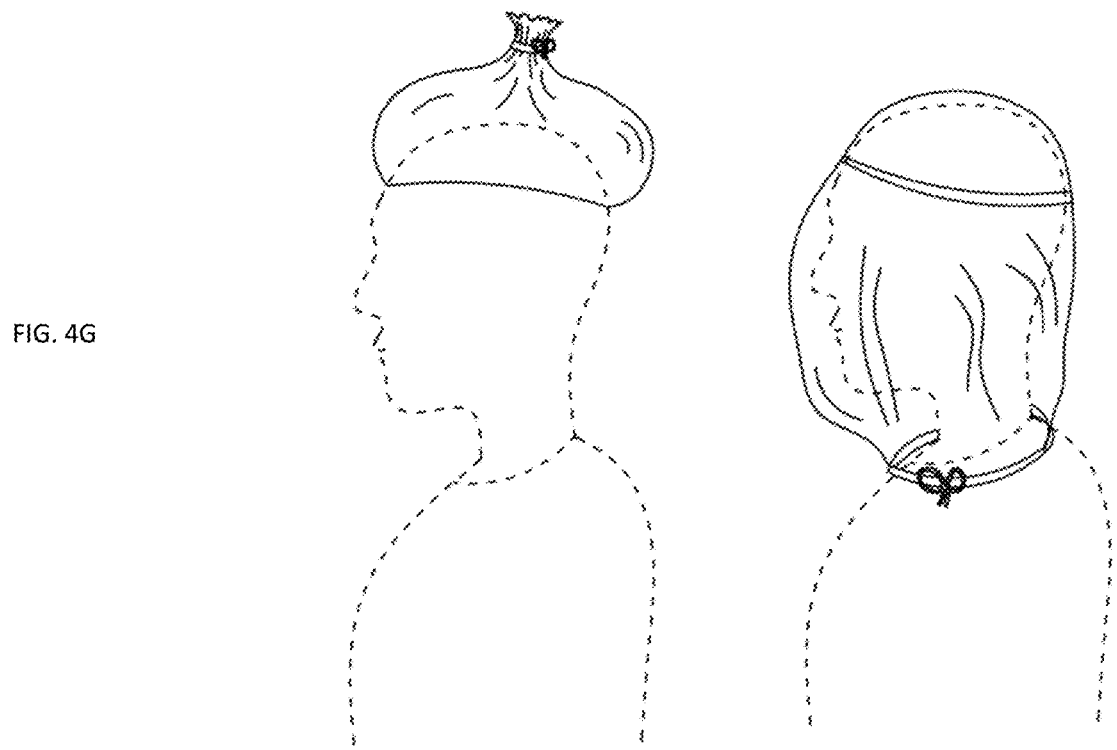

FIG. 4G shows a convolutional network for generating videos from thumbnail images or videos. The input clip goes through a series convolutions and nonlinearities that preserve resolution. After integrating information across multiple input frames (if multiple), the network up-samples temporally. The network outputs codes for a transformation of the input frames, which produces the final video. In the transformations: For each (x; y; t) coordinate in the video expansion, the network estimates a weighted combination of neighboring pixels from the input frame to render the predicted frame. The transformation is applied by convolution. The transformer output probability is biased by video context as done in the prior transformers.

One embodiment uses the GAN with a spatio-temporal convolutional architecture that untangles the scene's foreground from the background. This model can generate tiny videos up to a second at full frame rate better than simple baselines and can predict plausible futures of static images. The generator uses a deep convolutional network that inputs low-dimensional random noise and outputs a video. Spatiotemporal up-convolutions (2D for space, 1D for time) are used to model video. The generator also models the background separately from the foreground. The network produces a static background (which is replicated over time) and a moving foreground that is combined using a mask. A discriminator network is used to distinguish real videos from fake videos.

Another embodiment utilizes GANs with Spatial Transformer Networks (STNs) as the generator or Spatial Transformer GANs (ST-GANs). ST-GANs seek image realism by operating in the geometric warp parameter space. The ST-GAN can generate high-resolution images indirectly since the predicted warp parameters are transferable between reference frames.

Yet another embodiment uses Variational Autoencoders (VAEs) with two neural networks: an encoder comprised of convolutional layers that encode an object (image, text, sound) into a latent vector; and a decoder comprised of deconvolutional layers that decode a latent vector back into the object. As the autoencoder network reconstructs the data but cannot generate new objects, the variational autoencoder (VAE) requires an additional feature that allows it to learn the latent representations of the inputs as soft ellipsoidal regions rather than isolated data points. New data can be generated by sampling latent vectors from the latent space and passing them into the decoder.

In addition to controlling the surgical operation, the neural network can be used to provide local edge processing for IOT devices. A striking feature about neural networks is their enormous size. To reduce size of the neural networks for edge learning while maintaining accuracy, the local neural network performs late down-sampling and filter count reduction, to get high performance at a low parameter count. Layers can be removed or added to optimize the parameter efficiency of the network. In certain embodiments, the system can prune neurons to save some space, and a 50% reduction in network size has been done while retaining 97% of the accuracy. Further, edge devices on the other hand can be designed to work on 8 bit values, or less. Reducing precision can significantly reduce the model size. For instance, reducing a 32 bit model to 8 bit model reduces model size. Since DRAM memory access is energy intensive and slow, one embodiment keeps a small set of register files (about 1 KB) to store local data that can be shared with 4 MACs as the leaning elements). Moreover, for video processing, frame image compression and sparsity in the graph and linear solver can be used to reduce the size of the local memory to avoid going to off chip DRAMs. For example, the linear solver can use a non-zero Hessian memory array with a Cholesky module as a linear solver.

In one embodiment, graphical processors (GPUs) can be used to do multiply-add operations in neural networks. In another embodiment, in a Tensor processing unit (TPU), a systolic array can be used to do the multiply-add operations. The matrix multiplication reuses both inputs many times as part of producing the output. The neural processor can read each input value once, but use it for many different operations without storing it back to a register. Wires only connect spatially adjacent ALUs, which makes them short and energy-efficient. The ALUs perform only multiplications and additions in fixed patterns, which simplifies their design. The systolic array chains multiple ALUs together, reusing the result of reading a single register. During the execution of this massive matrix multiply, all intermediate results are passed directly between 64K ALUs without any memory access, significantly reducing power consumption and increasing throughput.

In another embodiment, original full neural network can be trained in the cloud, and distillation is used for teaching smaller networks using a larger "teacher" network. Combined with transfer learning, this method can reduce model size without losing much accuracy. In one embodiment, the learning machine is supported by a GPU on a microprocessor, or to reconfigure the FPGA used as part of the robot processing as neural network hardware.

The system can implement Convolutional Neural Networks (CNN) such as AlexNet with 5 Convolutional Layers and 3 Fully Connected Layers. Multiple Convolutional Kernels (a.k.a filters) extract interesting features in an image. In a single convolutional layer, there are usually many kernels of the same size. For example, the first Cony Layer of AlexNet contains 96 kernels of size 11×11×3. The width and height of the kernel are usually the same and the depth is the same as the number of channels. The first two Convolutional layers are followed by the Overlapping Max Pooling layers that we describe next. The third, fourth and fifth convolutional layers are connected directly. The fifth convolutional layer is followed by an Overlapping Max Pooling layer, the output of which goes into a series of two fully connected layers. The second fully connected layer feeds into a softmax classifier with 1000 class labels. ReLU nonlinearity is applied after all the convolution and fully connected layers. The ReLU nonlinearity of the first and second convolution layers are followed by a local normalization step before doing pooling. But researchers later didn't find normalization very useful. So we will not go in detail over that. Max Pooling layers are usually used to downsample the width and height of the tensors, keeping the depth same. Overlapping Max Pool layers are similar to the Max Pool layers, except the adjacent windows over which the max is computed overlap each other. The authors used pooling windows of size 3×3 with a stride of 2 between the adjacent windows. This overlapping nature of pooling helped reduce the top-1 error rate by 0.4% and top-5 error rate by 0.3% respectively when compared to using non-overlapping pooling windows of size 2×2 with a stride of 2 that would give same output dimensions.

One embodiment runs TensorFlow with a prebuilt model called "inception" that performs object recognition. YOLO and reinforcement learning can be used for robot control as well. YOLO (You only look once) performs real time object detection. Compared to other region proposal classification networks (fast RCNN) which perform detection on various region proposals and thus end up performing prediction multiple times for various regions in an image, Yolo is more like FCNN (fully convolutional neural network) and passes the image (n×n) once through the FCNN and output is (m×m) prediction. This the architecture is splitting the input image in m×m grid and for each grid generation 2 bounding boxes and class probabilities for those bounding boxes.

Reinforcement learning (RL) provides learning sequential decision making processes that enable robots to learn and adapt to their environment online. An RL agent seeks to maximize long-term rewards through experience in its environment. The robot is pretrained and then customized to its in environment with a few samples (be sample efficient); and the robot uses a combination of 5G edge processing and a reduced matrix to increase performance to take actions continually in real-time, even while learning.

Figure 1F:
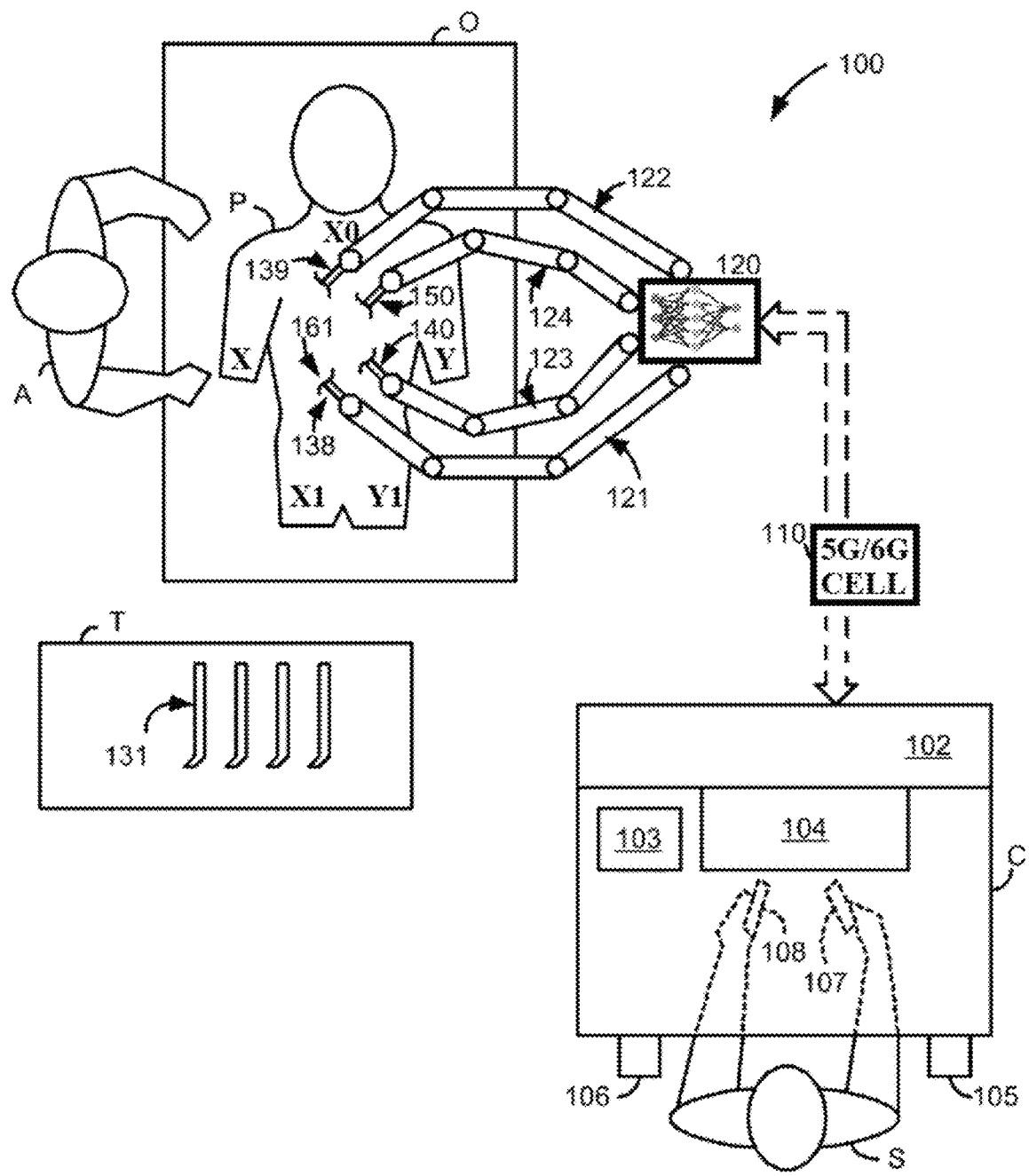
FIG. 1F illustrates, as an example, a top view of an operating room employing a robotic surgical system with AI assistance.

FIG. 1F illustrates, as an example, a top view of an operating room employing a robotic surgical system with AI assistance. The robotic surgical system 100 including a console ("C") (also may be referred to herein as a surgeon console, master console, master surgeon console, or surgical console) utilized by a surgeon ("S") while performing a minimally invasive diagnostic or surgical procedure with assistance from zero or more assistants ("A") on a patient ("P") who is reclining on an operating table ("O"). A plurality of markers X0, X, Y, X1, Y1 . . . Xi, Yi are placed on patient P. These markers serve to tie the digital coordinates to the physical coordinates and improve robot positioning accuracy.

Above, below or near the patient is a scanner which can be X-ray or RF or ultra-sound, among others. The scanner can provide positioning information as well as anatomical imaging of the patient. For example, the scanner can generate lung images for diagnosis. Preferably, the scanner is an ultrawide band (UWB) scanner operating at terahertz (THz) frequency. The system uses a plurality of transceiving monopole antennas within the frequency range of 300-15000 MHz. A reservoir tank can used between the antennas and the human body as a coupling media. The array of antennas can be moved and tuned to the target region of the patient as a real-time radar-based measurement. A single antenna is used for electromagnetic transmission, and 23 others are used for measuring the electromagnetic field. A pulse-shaping circuit, directional coupler, reflector, and amplifier are used in the time domain radar. UWB can be used to compensate for patient motion. When the patient moves, the reflected signals will fluctuate. The fluctuation of signals denoting the movement of objects is transferred to the control center of the surveillant. The information could be fed back instantaneously to the doctors or nurses. It could also be recorded and analyzed in the future for the health condition of the patient. A UWB radar can measure the speed and position of the patient on the mattress and compensate for positioning determination purposes by adding the patient movement vector to the patient HD anatomical map. For more detailed UWB mapping/positioning operations, the UWB transmitter emits discrete pulses to the human body and the reflected pulses from the anatomy arrived at UWB receiver and then the result is recorded. Signal processing is performed through obtaining the pulses response. For example, there exists a definite difference in reflection magnitude between the heart muscle and the blood when detecting the heart wall by UWB radar. Because of the impedance difference between the cardiac muscle and blood, a roughly 10% reflection magnitude of the radio frequency energy at the heart muscle-blood boundary can be expected. The UWB receiver can measure the difference, and show it on the screen, which reflects the status of heart. Similar UWB reflection at chest/lung interface, air/chest interface, and at vessel boundaries can be imaged by adjusting the emitting pulse power. UWB can monitor respiratory patterns, the Apnea monitoring in infants, obstructive sleep apnea monitoring, Polysomnography (sleep related studies), dynamic chest diameters measurement, allergy and asthma crisis monitoring, and chest imaging.

The console C includes a master display 104 (also referred to herein as a display screen or display device) for displaying one or more images of a surgical site within the patient as well as perhaps other information to the surgeon. Also included are master input devices 107 and 108 (also referred to herein as master manipulators or master tool manipulators (MTM), master grips, hand control devices), one or more foot pedals 105 and 106, a microphone 103 for receiving voice commands from the surgeon, and an AI processor 102. The master input devices 107 and 108 may include any one or more of a variety of input devices such as joysticks, gloves, trigger-guns, hand-operated controllers, or the like. The processor 102 may be a computer or a part of a computer that may be integrated into the surgeon console or otherwise connected to the surgeon console in a conventional manner.

The surgeon performs a minimally invasive surgical procedure by manipulating the master input devices 107 and 108 so that the AI processor 102 causes their respectively associated slave arms 121 and 122 (also referred to herein as slave manipulators or slave robots) of the patient side cart (PSC) 120 with AI processors therein to manipulate their respective removeably coupled and held surgical instruments 138 and 139 (also referred to herein as tools or minimally invasive surgical instruments) accordingly, while the surgeon views three-dimensional ("3D") images of the surgical site on the master display 104. The tools 138 and 139 can be Intuitive Surgical Inc.'s ENDOWRIST™ articulating instruments, which allow a full six degrees of freedom of motion. At the operating end of each of the tools 138 and 139 is a manipulatable end effector such as a clamp, grasper, scissor, stapler, blade, needle, or needle holder. A stereoscopic camera 140 (also referred to herein as an body cavity camera) provides right and left camera views to the AI processor 102 so that it may process the information according to programmed instructions and cause it to be displayed on the master display 104.

Sensors are provided on the robot arms to detect force and change in force in X,Y,Z to train the AI processor. Other robotic parameters such as (1) rotation per minutes or RPMs, (2) armature current, (3) angle and direction, (4) sound of motor, etc. are measured. As a drill or knife is robotically controlled, the drill or knife would have highly sensitive sensors for (1) RPMs, (2) armature current, (3) angle and direction, (4) sound of motor, etc. These parameters provide real-time robot set of data. These parameters provide data that is collected in many successful operations. The real-time images not only have all the previous metatags discussed, but also have the real sensitive sensor data for (1) RPMs, (2) armature current, (3) angle and direction, (4) sound of motor, etc. Now the system can be trained to show the sensitive sensors changes for (1) RPMs, (2) armature current, (3) angle and direction, (4) sound of motor, etc. going from one tissue type to another. As above the change sensitive sensors for (1) RPMs, (2) armature current, (3) angle and direction, (4) sound of motor, etc. can be used to compare to real-time operations. If the tissues are identified correctly and within range, and the sensitive sensors data for (1) RPMs, (2) armature current, (3) angle and direction, (4) sound of motor, etc. and their associated changes are within range, the images are annotated with virtual information showing that tissues and sensitive sensors data for (1) RPMs, (2) armature current, (3) angle and direction, (4) sound of motor, etc. are in order. If, however, the sensitive sensors data for (1) RPMs, (2) armature current, (3) angle and direction, (4) sound of motor, etc. or the associated changes appear out of normal range, alarms would sound, and automated robotic stops would be done to investigate the out of norm situation. With this system, the surgeon can create a "sensitivity" of sensitive sensors data for (1) RPMs, (2) armature current, (3) angle and direction, (4) sound of motor, etc. at various parts of the operations, so the system may alarm when it approaches a nerve as the sensitive sensors data for (1) RPMs, (2) armature current, (3) angle and direction, (4) sound of motor, etc. and change of sensitive sensors data alarm for (1) RPMs, (2) armature current, (3) angle and direction, (4) sound of motor, etc. is set at a more sensitive level than another part of the operation.

In yet another aspect, the system includes a hyperspectral camera, an UWB transceiver providing anatomical scans to an AI processor to classify and recognize human anatomical features, and a processor to control robot movement to reach a selected anatomical target. Embodiments can use fiber Bragg grating (FBG) sensors coupled to the UWB transceiver to detect temperature, pressure, position, tilt, among others. The robot uses one or more ultra-wideband (UWB) probes to scan the patient. The UWB radio sensors provide in a radar-like scanning to provide MRI voxel results with high temporal and spatial resolution, good tissue penetration, low exposition by radio waves, and compatibility with existing diagnostic and therapeutic equipment. The probes can be positioned at the tip with fiber Bragg grating (FBG) sensors as detailed above. One or more UWB scanners are placed proximal to the patient to non-invasively scan the patient and provide positioning information on the robot arms inside the patient. In one embodiment, a UWB probe 150 provides two-dimensional ("2D") UWB image slices of an anatomic structure to the AI processor 102 so that the processor 102 may generate a 3D UWB computer model of the anatomic structure and cause the 3D computer model (or alternatively, 2D "cuts" of it) to be displayed on the master display 104 as an overlay to the endoscope derived 3D images or within a picture-in-picture ("PIP") in either 2D or 3D and from various angles and/or perspectives according to surgeon or stored program instructions. Each of the tools 138 and 139, as well as the camera 140 and UWB probe 150, is preferably inserted through a cannula or trocar (not shown) or other tool guide into the patient so as to extend down to the surgical site through a corresponding minimally invasive incision such as Incision 166. Each of the slave arms 121-124 is conventionally formed of linkages which are coupled together and manipulated through motor controlled joints (also referred to as "active joints"). Setup arms (not shown) comprising linkages and setup joints are used to position the slave arms 121-124 vertically and horizontally so that their respective surgical related instruments may be coupled for insertion into the cannula.

The AI processor performs various functions in the system 100. One function that it performs is to translate and transfer the mechanical motion of master input devices 107 and 108 to their associated slave arms 121 and 122 through control signals over 5G or 6G cellular connection 110 so that the surgeon can wirelessly manipulate their respective tools 138 and 139. Alternatively, a direct wired connection between the surgeon console and the system can be done as is conventional. Another function of the AI processor 102 is to implement robotic assisted surgery capability.

Although described as a processor, it is to be appreciated that the AI processor 102 may be implemented in practice by any combination of hardware, software and firmware. Also, its functions as described herein may be performed by one unit, or divided up among different components, each of which may be implemented in turn by any combination of hardware, software and firmware. Program code or instructions for the AI processor 102 to implement the various methods and functions described herein may be stored in processor readable storage media, such as memory.

Prior to performing a minimally invasive surgical procedure, UWB images captured by the UWB probe 150, right and left 2D camera images captured by the stereoscopic camera 140, and end effector positions and orientations as determined using kinematics of the slave arms 121-124 and their sensed joint positions, are calibrated and registered with each other.

In order to associate the UWB image with the rest of the surgical environment, both need to be expressed in the same coordinate frame. Typically, the UWB probe 150 is either labeled with markers and tracked by a tracking device such as the OPTORAK® position sensing system manufactured by Northern Digital Inc. of Ontario, Canada, or held by a robot with precise joint encoders. Then the rigid transformation between the UWB image and the frame being tracked is determined (which is typically referred to as the UWB calibration). To perform the UWB calibration, the UWB probe 150 may be placed in three known orientations defined by the AX=XB calibration phantom. The UWB image frame may then be defined by three fiducials which appear in each of the three poses. The three poses allow three relative transformations based on OPTOIRAK® readings (A) and three relative transformations based on the UWB images (B) for the AX=XB registration. Camera calibration can be done using markers added to a typical checkerboard video calibration phantom, and each corner of the checkerboard is digitized using a calibrated OPTOTRAK® pointer. Thus, the corner positions may be reported with respect to the OPTOTRAK®. The calibration may then be performed by placing the phantom in view of the camera 140 in several dozen orientations, and recording both stereo image data and OPTOIRAK® readings of the four checkerboard corners. The images may then be fed into the calibration toolbox, which determines the intrinsic and extrinsic camera parameters, as well as the 3D coordinates of the grid corners in the camera frame. These coordinates may then be used with the OPTOTRAK® readings to perform a point-cloud to point-cloud registration between the camera 140 rigid body and camera frame.

The processor/controller 102 is configured to use the robot kinematics to report a coordinate frame for the UWB probe 150 tip relative to the camera 140. However, due to inaccuracies in the setup joint encoders, both of these coordinate frames may be offset from their correct values. Thus, it may be necessary to register the offsets between the real camera frame of the camera 140 and the camera frame calculated from the kinematics as well as between the real and kinematic UWB probe 150 frames. With this complete, the kinematics may be used in place of the OPTOTRAK® readings to determine UWB image overlay placement.

If the position of the camera 140 doesn't overly change, a constant transformation may be assumed between the kinematic tool tip and the OPTOTRAK® rigid body. Using an AX=XB formulation, the UWB probe 150 may be moved, for example, to several positions, and the static offset between the tool tip and OPTOTRAK® rigid body registered. The camera offset can be determined with each movement, or alternatively registration may be redone each time the camera is moved. For intra-operative, the registration may be better performed using video tracking of a visual marker on the UWB probe 150 instead of the OPTOTRAK® readings. Thus, if the camera were moved while using tool tracking, the registration can be corrected on the fly as the tool is tracked. In addition to, or alternatively, manual registration of UWB and camera images may be performed using conventional grab, move and rotate actions on a 3D UWB computer model of an anatomic structure, so that the computer model is properly registered over a camera model of the anatomic structure in the master display 104. Slave arms 123 and 124 may manipulate the camera 140 and UWB probe 150 in similar manners as slave arms 121 and 122 manipulate tools 138 and 139. When there are only two master input devices in the system, however, such as master input devices 107 and 108 in the system 100, in order for the surgeon to manually control movement of either the camera 140 or UWB probe 150, it may be required to temporarily associate one of the master input devices 107 and 108 with the camera 140 or the UWB probe 150 that the surgeon desires manual control over, while its previously associated tool and slave manipulator are locked in position.

Robot movement can be constrained by forbidden region virtual fixtures which set predefined limits on robot movement to prevent undesired tissue collision. In another aspect, guidance virtual fixtures may be used to constrain a surgical instrument to move on a fixed trajectory. For example, a suturing trajectory may assist the surgeon to perform suturing movements along a curved path.

In certain embodiments, the robot's computer vision, location sensors, and electrical or pH sensors can differentiate tissues such as endometrial, heart, mucosal and submucosal tissue, such as to adjust one or more treatment parameters (e.g. to stop treatment and/or modify the temperature of treatment) based on the differentiation. Applicable visible sensors include but are not limited to: visible light camera; infrared camera; CT Scanner; MRI; and combinations of these. In some embodiments, energy applied is based on one or more signals from the visible sensor, such as a sensor providing a signal correlating to tissue color wherein the energy delivered is modified based on a tissue color change and/or tissue expansion injectate comprise a visible dye or other visualizable marker used to assess tissue expansion. The robot can include a temperature sensor configured to monitor the temperature of treatment. The robot can include a sensor that measures the pH proximate the tissue being expanded and produces a signal correlating to the amount of tissue expansion based on the measured pH (e.g. based on a change in the measured pH that occurs during tissue expansion). In some embodiments, the robot can have an ultrasound transducer directed at the tissue being expanded and produces a signal correlating to the amount of tissue expansion based on an analysis of an image of the expanding tissue produced by the ultrasound transducer. The robot can include a transducer selected from the group consisting of: fiber optic cable, a heat generating element; a drug delivery element such as an iontophoretic drug delivery element; a magnetic field generator; an ultrasound wave generator such as a piezo crystal; a light producing element such as a visible and/or infrared light emitting diode; a motor; a vibrational transducer; a fluid agitating element; and combinations of these. The robot can dispense a visualizable material is selected from the group consisting of; colored dye; radiopaque agent; ultrasonically visible material; magnetically visible material; and combinations of these. The system is configured to deliver abrasive particles, such as abrasive particles delivered to one or more treatment elements to assist in the treatment of tissue, such as to improve cellular disruption caused by a mechanical abrasion treatment by visualizing the treatment in real time.

For example, a video camera, LIDAR camera, or imaging device can be configured to be inserted into the patient and can comprise a visual light camera; an ultrasound imager; an optical coherence domain reflectometry (OCDR) imager; and/or an optical coherence tomography (OCT) imager, such as when integral to, attached to, contained within and/or proximate to the robot tip, lumen, or other parts of the robot arm. In one embodiment, a multispectral camera or ultrasound transducer mounted to the robot arm tip can be rotated and/or translated to create a multi-dimensional image of the area surrounding the robot arm tip. Image and other information provided can be provided to an operator of system and/or used by a component such as AI processors, to automatically or semi-automatically adjust one or more system parameters such as one or more energy delivery parameters.

Before surgery, the surgeon can do a preoperative plan for performing procedures. The information can include targeted tissue, non-targeted tissue, critical tissue (e.g., tissue to be protected or avoided), access paths, cutting/drilling paths, instrument orientations (e.g., delivery instruments, surgical instruments, etc.), working spaces, safety barriers, hold spots, or the like. The information can be used to determine or modify a surgical plan and can be inputted via a touch screen, keyboard, or the like. A method of using an image in which a sketch on the image indicates parts of the bone are to be removed. This is a freehand adjustment by the surgeon to the preoperative plan, layered on top of medical imaging (MRI, CT, etc.). This adjustment to the surgical plan is transmitted to the AI surgical robot and it only removes the desired area, the surgeon supervises the robot during the procedure to take over/resume the operation if necessary.

During operation, an incision marking module determines an incision spot from the pre-operative plan and scans the patient to determine if s/he is properly positioned on the operating table and calibrates its position markers. The robot arm inserts a guide wire into the selected incision site. The system includes a failsafe that allows the surgeon on hand to stop the process at any point. Stopping the process may include a teaching step in which the surgeon defines the tissue type visible, to improve the functionality of the robot AI software.

The AI guidance system may utilize the camera to take an image of the point of interest and the progression module may compare that image to the image recognition database to determine if the tissue present is the desired tissue type that will allow the surgical robot to proceed. Historical data of many operations that stores the amount of time (video) and the Virtual identified images on the tissue. The tissues identified may be in a time sequence as the operation proceeds. In a real-time operation, the sequence of image-recognized tissue (and the timing of getting to and through these recognized tissues) is compared to the historical database. If the real-time recognized tissues are correlated with the same sequence of tissues in the historical database, the system proceeds. However, if a recognized tissue does not appear in the sequence history, or if the recognized tissue appears earlier than expected, the fail system is alerted, which causes an alarm, with a virtual message over the non-normal images.

In addition, the real-time image is preferably projected into a perspective image such that the surgeon can manipulate the end effector of a tool, 138 or 139, through its associated master input device, 107 or 108, as if viewing the workspace in substantially true presence. By true presence, it is meant that the presentation of an image is a true perspective image simulating the viewpoint of an operator that is physically manipulating the tools. Thus, the processor 102 transforms the coordinates of the tools to a perceived position so that the perspective image is the image that one would see if the camera 140 was looking directly at the tools from a surgeon's eye-level during an open cavity procedure.

One embodiment learns from surgeon motions for a variety of prior operations whose robot motions and corresponding images have been recorded. Robotic manipulators are moved by the surgeon or by precisely designed control algorithms, that are based on an accurate knowledge of the structural and physical parameters of the manipulator. These includes angles between joints, lengths of links, masses, frictions, and so on. The more accurate these parameters are given, the more precisely a control architecture can be designed. The dynamical model of a robot, i.e. the mathematical model describing how inputs affect the movement of each joints, can be very complex, especially when dealing with robots with many Degrees of Freedom (DOFs). Links are often dynamically coupled: the movement, velocity and acceleration of a link affects the other in complex ways. There are inertia effects, centrifugal, Coriolis and gravitational effects, non-linear frictions and so on. Machine learning (ML) allows computers to learn directly from data and is intuitive to understand why it is useful in this case. Much as a human baby, a robot can learn how to move simply by moving. A carefully designed machine learning algorithm can learn to move in a trial-and-error fashion, doing many trials and analyzing the effects of its actions. A framework consists of three main components: motion retargeting, motion imitation, and domain adaptation. 1) First, given a reference motion, the motion retargeting stage maps the motion from the surgeon's actions to the robot's actions. 2) Next, the motion imitation stage uses the retargeted reference motion to train a policy for imitating the motion in simulation. 3) Finally, the domain adaptation stage transfers the policy from simulation to a real robot via a sample efficient domain adaptation process. All data is provided to a deep learning network for learning effective surgical procedures. Initially the trained robot operates as an assistant to the surgeon, and with sufficient data, the robot can operate autonomously and the surgeon simply supervises the robot and takes over only when needed. The embodiment takes a motion sensor data from a surgeon during an operation used as training data (as stored by the robot during prior operations) and uses reinforcement learning to complete goals via rewards to train a control policy. Optional motion capture of surgeon motion is filmed from multiple angles performing various movements while wearing a suit filed with reflective "markers." The markers enable the computer to build a model of the points in space of each limb of the surgeon. The videos can rotate the image of each frame to help the DNN at understanding unusual positions of the human body, and each of these "poses" are assembled into a "trajectory" of limbs from one frame to the next, to reconstruct the entire movement of the surgeon arms in the video. The marker movement provides extra data to the robotic arm movements captured by sensors in the robot. The robotic system records all actions taken by the surgeon while performing various tasks. The movements are recorded and the robot is then programmed to reproduce the tasks while adapting to changes in the patient tissue, organ, or muscle, for example. By leveraging reference motion data, a single learning-based approach is able to automatically synthesize controllers for a diverse repertoire of behaviors for legged robots and the use of sample efficient domain adaptation techniques into the training process enables the system to learn adaptive policies in simulation that can then be quickly adapted for real-world deployment. To transfer a policy trained in simulation to the real world, sample efficient domain adaptation techniques adapt the policy to the real world using only a small number of trials on the real robot. Th system applies domain randomization during training in simulation, which randomly varies the dynamics parameters, such as mass and friction. The dynamics parameters are then also collected into a vector and encoded into a latent presentation by an encoder where latent encoding is passed as an additional input to the policy. The dynamics parameters of the simulation are varied during training, and also encoded into a latent representation that is provided as an additional input to the policy. When transferring the policy to a real robot, the encoder is not used and the AI processor determines action that maximizes the robot's rewards in the real world. This is done using advantage weighted regression, a simple off-policy reinforcement learning algorithm.

Mobile Surgery Systems

The robotic surgery system is advantageously small for mobility purposes. For example, the robot surgery system can be positioned on a plane where plane movement is accounted for and suitably compensated in case a person needs emergency surgery. In this system, a 5G or 6G or satellite communication system provides low latency high bandwidth communication with medical professionals on the ground, and the robot performs surgery autonomously but supervised by surgeons, among others. Images from scanners such as CT or UWB scanners are used to detect COVID. Lung segmentation is used to identify and localize whole lung regions, which were then used as input for scanner-based prediction of COVID-19 disease. Multiple classification models and rationales can be used, including a hybrid model that performs 3D classification on multiple crops (i.e., several slices) at fixed resolution within an image, and a full 3D image classification implementation considering one complete volume at a fixed size. In one embodiment, scanner images are provided to lung segmentation for localization to chest cavity region. Following cropping to lung region, two methods were considered for differentiation of COVID-19 from other clinical entities. The lung segmentation model is trained using the AH-Net architecture. The hybrid 3D and full 3D models use a Densnet-121 architecture adapted to utilize 3D operations (i.e., 3D convolutions) compared to original 2D implementation. Images were clipped to HU range (−1000, 500) and cropped to bounding box fitting to the maximum dimensions of lung regions with an extended 5 voxel buffer. For the full 3D model, the entire lung region (without masking) was resampled to size 192×192×64 for training and inference. For the hybrid model, images were resampled to resolution 1 mm×1 mm×5 mm and sub-crops of 192×192×32 were sampled from lung regions, applying mask to obtain lung-only tissue, at a frequency of 6 crops/patient for training and 15 crops/patient at inference. A Full 3D Model resampled the cropped lung region of CT to a fixed size (192×192×64 voxels) for input to algorithm. Hybrid CT resampled the cropped lung region of CT to fixed resolution (1 mm×1 mm×5 mm) and sampled multiple 3D regions (192×192×32) for input to algorithm. At training, 6 regions/patient were used. At inference, regions/patient were used and results were averaged to produce final probability of COVID-19.

Figure 2A:
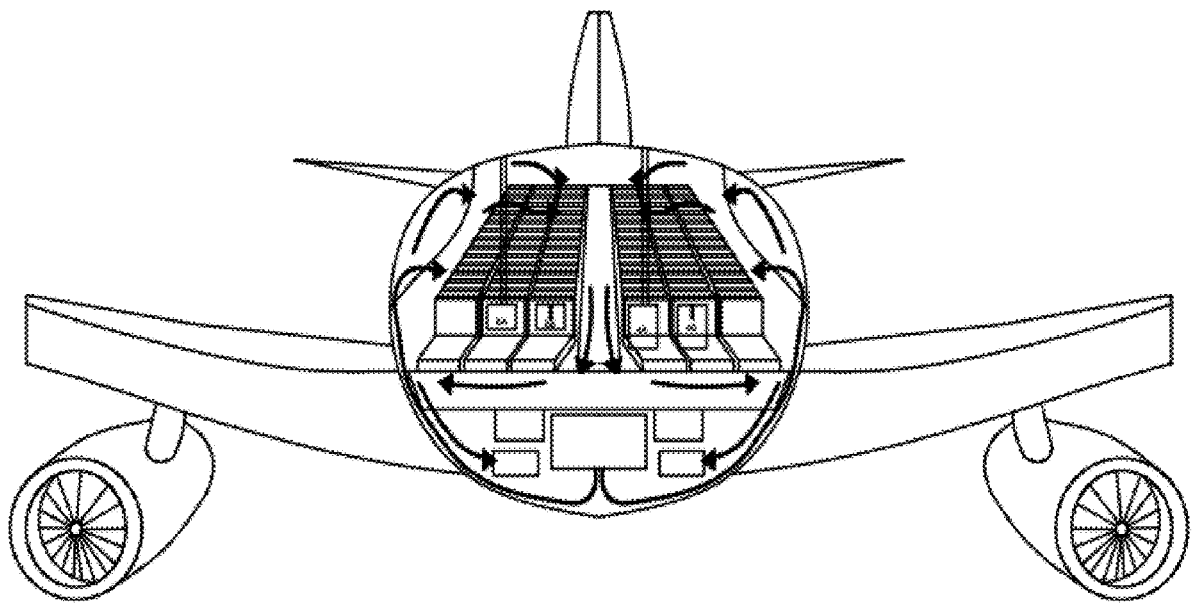
FIGS. 2A-2B show an exemplary mobile travel vehicle cabin with enclosures for traveler protection.
Figure 2B:
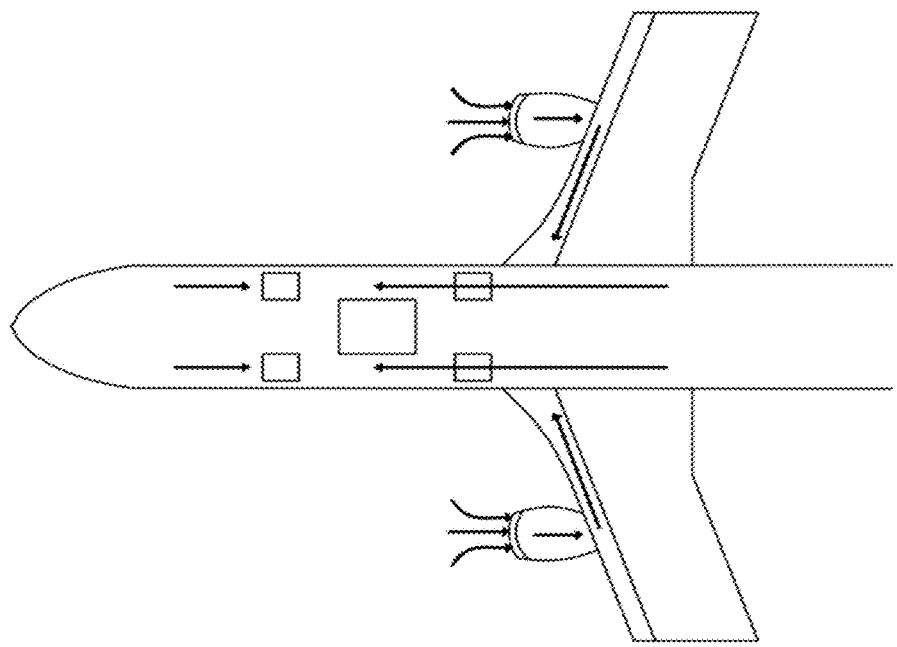

FIG. 2A shows exemplary mobile robotic surgery environment on a plane. FIG. 2B shows exemplary air flow for airplane cabin. As shown in FIG. 2A, outside air enters through the engine turbines and is compressed, heating it. It then passes through cooling packs located below a cabin 2. The packs help regulate the temperature of the compressed air. Meanwhile, air from the cabin travels to the same area to pass through HEPA filters. These filters, also used in hospitals, are capable of removing at least 99.9% of particles like bacteria, viruses and fungi. The two air sources are then infused 50-50 through an air-mixing unit and circulated back to the cabin. The mixed air enters the cabin through overhead vents and downward in a circular motion.

Incoming filtered air is provided from the top of the cabin to full enclosures 4A or 6A, or alternatively can be routed through seats to partial enclosures 4B or 6B. The full enclosures provide protection down to the bottom of the seat, while the partial enclosures provide protection to a region between the neck and the seat bottom and provides more interactions with fellow passengers, but less protection than the full enclosure with better air seal. In these embodiments, the enclosures or chambers can have substantially rectangular or square shapes, or as described and illustrated below, can be substantially oval or curvilinear-shaped for esthetic reasons.

A portion of the air are recirculated while most leaves the cabin through floor vents. From there, about half of the exited cabin air is dumped outside while the rest is sent back to the HEPA filter to be mixed again with the fresh outside air. A cabin's air volume gets refreshed over the course of two to three minutes.

In one embodiment, inflatable or expandable hoods (origami hoods) can be stored in aircraft passenger service units (PSUs) and associated systems. These PSUs have a chassis configured to structurally couple to a corresponding portion of an aircraft structure (e.g., to an airframe). Such a chassis can also be configured to modularly arrange and/or to retain one or more PSU fixtures. The PSU fixture is configured to provide one or more services (e.g., information services, lighting services, environmental services, life safety services, passenger convenience services) to a passenger cabin of an aircraft. Some gaspers have an adjustable configuration to permit adjustment of a pressure loss through the vent, and thereby to permit adjustment of a flow rate of air through the vent. The PSU has separate components for each feature, passenger oxygen, lighting, and gasper. Dependent on the pitch between seat rows, a spacer may be employed to fill in gaps between PSU fixtures. The PSUs with the inflatable hoods can be made compatible with an existing fleet of aircraft and different PSU configurations can be made corresponding to different airline customer desires. The PSU can include a projector that may project an image on the cabin wall or on the user view (middle hood) so that the OLED display does not need to be incorporated in the hood for embodiments that are disposable or user replaceable as desired for cleanliness concerns.

One aspect can be a cabin, comprising: inlets and outlets adapted to be coupled to an air filter; a chair; a partial or full air isolation chamber coupled to the chair, the chamber receiving breathable filtered air from the air filter, the chamber removing bad air from the chamber and send bad air to the filter to be filtered; and means to place a passenger in the full or partial chamber. Variations of the above cabin can include the following:

The chamber has a first portion to fit over a user head.

The chamber has a second portion to fit over a user eye.

The chamber has a third portion to fit below a mouth and sealably connected to user shoulder or below to provide air sealing.

The chamber can be a drop down hood that can drop down from a cabin ceiling or a PSU.

The chamber can be a seat top extension with pivotable and extendable hood receiving air from tubings inside the seat and run under the seat to the air filter.

The chamber can be portable headworn devices that receive air from portable hood, cap, mask, headsets, and other wearable items.

The chamber can have displays to provide virtual, augmented, or extended reality (VR/AR/XR) views.

The chamber can have audio and haptic feedback actuators.

The chamber can simulate wind and mist.

Optionally an oxygen cartridge can be coupled to the chamber to supply air in case of fire.

For VR, the chamber can have a moveable door over the display to block external views.

For AR/XR, the display can be flexible and foldable OLED displays, or to save power, can be unicolor e-ink displays.

To save power, the display can be colored icons on a side of the display.

The chamber can have built-in air filter and/or built-in disinfectant systems such as UVC LEDs. The UVC LEDs can clean the air from the outside, and can be movable over the chamber and activated prior to use to clean the chamber.

Mobile Air Protection Systems

FIG. 2C shows an exemplary travel protection system for travelers. The system includes an enclosure or chamber 10 such as a bubble chamber that includes an air inlet 12 injecting air under positive pressure into the chamber. The positive pressure keeps pathogens emitted from a neighbor from being inhaled by the user. The enclosure/chamber 10 has an air suction tube 14 to pull air droplets by the user away from the chamber 10 and into a built-in air disinfectant system in box 18.

On aspect can be a mobile chamber with built-in air disinfectant using UVC LEDs, for example. Optional disposable air filter such as N95 filters can be used. The mobile chamber can have a clear view chamber and such mobile chamber can be incorporated into a wearable mask with air filter in place. Optionally an oxygen cartridge can be coupled to the mask to supply air in case of fire.

Another aspect can be a mobile chamber with built-in air disinfectant using UVC LEDs, for example. Optional disposable air filter such as N95 filters can be used. The mobile chamber can have a flexible transparent/translucent OLED display in front of the eyes. A processor and data storage device can render images on the display to guide the user. The processor can have a low latency transceiver such as a 5G transceiver to receive data quickly. Additionally, the processor can offload compute intensive processors to nearby edge processors over the 5G connection and as a result reduces the battery size needed and increase device uptime prior to recharging. Thus, the mobile chamber can be incorporated into a wearable mask with air filter in place. The chamber can also be fixed to seats and beds, for example.

In one embodiment, the air disinfectant system includes a small motor with an air circulation fan that pulls in ambient air. The motor is small, such as laptop CPU cooling motors), and further the air can be pulled through user-replaceable N95 filters with melt-blown non-woven fabric. Preferably the N95 filter includes electret treatment to provide electrostatic adsorption capacity, which will further enhance the particle filtration capacity. Alternatively, materials with good hydrophobic properties but slightly larger structural pores can be used, such as polyester fibers, that is, polyester. While not as good as N95, polyester can protect against droplets after being folded in multiple layers. Important factors in the filter material include filtration efficiency, bacterial filtration efficiency (BFE) and respiratory resistance: Filtration efficiency: Under the condition of airflow (30±2) L/min, the filtration efficiency for aerodynamic median diameter (0.24±0.06) μm sodium chloride aerosol is not less than 30%; Bacterial filtration efficiency: Under specified conditions, the filtration efficiency for aerosols of *Staphylococcus aureus* with an average particle diameter of (3±0.3) μm is not less than 95%; Breathing resistance: In the condition of filtering efficiency and flow rate, the inhalation resistance does not exceed 49 Pa, and the exhalation resistance does not exceed 29.4 Pa. Among them, the second criterion to ensure the bacterial filtration effect is the filtration efficiency of *Staphylococcus aureus* bacterial aerosol (3 microns) is not less than 95%. The new coronavirus is an enveloped, non-segmented, single-stranded positive-stranded RNA virus with round or oval particles and a diameter of about 60-140 nm (0.06 to 0.14 microns). Although medical surgical masks have only 30% filtration efficiency for 0.3 micron-sized particles, since pathogens such as viruses and bacteria cannot exist in the air, they must be attached to dust, droplets and another microcluster, so they can also provide effective virus protection. The filter can be separately disinfected and reused when irradiated with ultraviolet light (wavelength 254 nm, intensity 303 uw/cm2, action 30 seconds).

One embodiment uses ultraviolet UV-C light-emitting diode (UVCLED) which is strong enough to destroy the genetic material—either DNA or RNA—of viruses and bacteria. To effectively kill viruses, UV-C light emission can be in a range of 200 to 280 nanometers, which has potential for harm to eyes/skin as well. The LED is inside of a protective enclosure at or near the air circulation fan to avoid skin irritation and eye damage. The UVC-LED can include an n-type semiconductor layer, a p-type semiconductor layer, an active layer, a first electron blocking layer and a second electron blocking layer. The active layer is located between the n-type semiconductor layer and the p-type semiconductor layer, and the wavelength of the maximum peak of the spectrum emitted by the active layer ranges from 230 nm to 280 nm, and the concentration of magnesium in the active layer is less than 1017 atoms/cm3. The first electron blocking layer and the second electron blocking layer are located between the p-type semiconductor layer and the active layer, the concentration of magnesium in the second electron blocking layer is greater than the concentration of magnesium in the first electron blocking layer, and the concentration of magnesium in the second electron blocking layer is greater than 1018 atoms/cm3.

In extended reality embodiments, an optional flexible display such as an OLED display 16 can render augmented reality, virtual reality, or extended reality images to provide information to the user. The display 16 is connected to a control box 18 with processor(s) that can render augmented reality. In one embodiment, to minimize battery weight, the box 18 is connected to 5G transceivers and transfers the rendering operations to a nearby edge 5G rendering system with low latency so that the display 16 is responsive to user operation while the processing can be done remotely. The control box 18 has air pipes feeding air into air inlet 12 and pipes for collecting air returning from outlet 14. These pipes or tubes are connected to an air filter system that includes an air pump with an air disinfection system such as an ultraviolet light system that integrally exposes the air to ultraviolet. Such exposure to ultraviolet light C kills any pathogens before such air is then circulated into bubble chamber and the output collected from the user's exhalation can also be provided to the disinfectant UV light sources to kill any possible pathogens emanating from the user.

The transparent OLEDs (sometimes referred to as T-OLEDs) can be used to display images, and in one embodiment, can be lighting panels—these are thin, area-lit and efficient lighting panels, that can be made transparent. In another embodiment, the display 16 can have an under-the-OLED camera which enables a selfie camera in a full-screen OLED AR/VR device. The display can optionally include touch functionality using capacitive or resistive sensors. In another embodiment, the display 16 can provide a "translucent" mode, so that the user can control the degree of virtual reality versus augmented reality. In another embodiment, a bone conduction audible system is coupled to bony structures on the head near the ear to provide sound for the user. A plurality of sound actuators can be used to provide 360-degree surround sound for the user.

In one implementation, the transparent OLED is made by providing a flexible glass, and forming a polymer layer laden with dryer at one side of the flexible glass; forming an insulative glue layer containing nano fibers or nano particles at the other side of the flexible glass to form a transparent flexible package substrate; coating a number of strips of flexible package glue at one side of the transparent flexible package substrate with the polymer layer, or directly coating flexible package glue on the entire surface of the other side of the transparent flexible package substrate with the polymer layer; oppositely assembling a manufactured flexible OLED substrate and the transparent flexible package substrate, wherein an OLED element is located corresponding to the polymer layer, and the flexible OLED substrate is adhered on the transparent flexible package substrate via the flexible package glue, and UV curing or thermal curing the flexible package glue to form a sealed flexible display device. One method includes directly adhering an insulative glue layer containing nano fibers or nano particles at the other side of the flexible glass, or: coating insulative glue material containing nano fibers or nano particles at the other side of the flexible glass, and curing the same to form the insulative glue layer; a main material of the insulative glue layer is acrylic resin body or epoxy resin body, which is filled with nano fibers or nano particles. A thickness of the flexible glass provided in the step 1 is smaller than 100 um, and a thickness of the polymer layer is 5-100 um. The OLED display substrate thus uses a flexible substrate and an OLED lighting element located on the flexible substrate. The thickness of the flexible glass is less than 100 um; and the thickness of the polymer layer is 5-100 um.

In a low power embodiment, only a select portion of the display 16 is enabled for rendering. To save power, a plurality of single-color LEDs can provide guidance with minimal power consumption. For example, the leftmost and rightmost LEDs are in a first color for indications, such as turn-left and turn-right. A plurality of second color LEDs are used for continuous animations across the frame using binocular rendering. The center four LEDs (orange, green, green, blue) are exclusively used for notifications. A mobile app allows remote triggering of different notification patterns for LEDs.

In one embodiment, ambient air outside the chamber 10 is picked up by the extender pipe/tube which eventually feeds into the air disinfectant unit in the control box 18. In one embodiment, flexible solar panels or other suitable energy scavenger devices can be part of the flexible extender to provide energy to the box 18.

FIGS. 3A-3C shows various operational views of an exemplary AR/VR/XR device that has the flexible screen 16 with a plurality of visibility conditions. In this example, a cap provides the screen 16 in front of the cap, while the control box 18 can be mounted on top or on the back of the cap. Preferably the box 18 is on top of the cap or the hood of FIGS. 4A-4G below. The display 16 is preferably a flexible OLED display that can be rolled, folded, or bent to a small shape for storage when not needed, and the display 16 can be unfolded to provide full visibility as shown in FIG. 3A. In the embodiment of FIG. 3A, the display 16 has a mount arm that can be removably be attached to a wearable item such as a cap. The cap can have a plurality of mounting means such as buttons or Velcro or zipper based mounting for the cap and the display mount arm. A rail is provided to expand the display from its mount position all the way to the other side of the cap. When fully expanded, the display 16 can wrap around the cap to provide a 180 degree view coverage as shown in FIG. 3A. The arm can be folded or slidably shortened to provide a partial or shorter display depth, as shown in FIG. 3B. The display can be moved to any point between the two sides of the cap to provide a partial extended reality view and a direct view for one or both eyes as desired. In one embodiment, the display 16 can be pleated, or folded by doubling the plastic back on itself (similar to a pleated fan or pleated flag) for ease of compression. Alternatively, the plastic screen 16 can be rolled in or out of the arm along a guide rail on the cap or wearable device.

The embodiment of FIGS. 3A-3C can still provide significantly safe air to the user and yet provide social interactions among people in known environments such as in an office whose workers have already been vetted through temperature checking and COVID pre-testing, for example. However, in unknown spaces such as in an airplane cabin with potential for large virus-containing droplets like a sneeze or a cough, the user can get additional protection with a flexible extension coupling the bottom of the facemask to the wearer's clothing and thus extending the bottom of the screen to the user's shirt/body. In one embodiment, the facemask or screen can be magnetically attached to the user's clothing via a flexible extender between the bottom of the screen and the user's clothing. Such flexible extender is comfortable to use, while restricting the flow of uncontrolled air to the user. The extender has an internal air pipe/tube that connects to the return air tube from outlet.

In one embodiment, the cap can carry an optional oxygen supply or breathable air supply. The air supply can be connected and turned on during severe air pollution period, an epidemic, or during fire emergencies. The system can buy the user valuable time to get out of life-threatening situations. To expedite escape, the system can communicate via the 5G transceiver to obtain map data and instructions on how to escape an emergency.

Another aspect can be a hat/cap/headwear with a flexible transparent/translucent OLED display in front of the eyes. A processor and data storage device can render images on the display to entertain the user. The processor can have a low latency transceiver such as a 5G transceiver to receive data quickly. Additionally, the processor can offload compute intensive processors to nearby edge processors over the 5G connection and as a result reduces the battery size needed and increase device uptime prior to recharging.

Variations of the headwear such as cap/helmet/crown/jewelry can be seen in FIG. 3D where the facemask can be rolled in an out of a mask housing or arm extending downward from one side of the cap. When not needed, the face mask is retracted inside the cap housing. When the facemask is needed, it can be pulled out of the housing and movably rolls from one side of the cap to the other side to cover the face of the cap wearer.

The headwear can have a button, Velcro, or secure means on each side of the headwear to which an arm can be attached. The arm can be secured on the headwear when not in use, and can drop down to the side of the face (next to the ear for example). The flexible display can be rolled or folded in an accordion like manner during storage in or near the arm, and can be extended from one side of the headwear to the other side over the face. Once extended, the flexible and clear display can act as a facemask and also can render images as part of VR/AR/XR operation.

As shown in FIG. 3D, the headwear can have a button, Velcro, or secure means on each side of the headwear to which an arm can be attached. The arm can be secured on the headwear when not in used, and can drop down to the side of the face (next to the ear for example). The arm can have one or more additional foldings to reduce the height of the arm. During use, the arm is fully extended, and then the flexible display can be moved along a rail across the two sides of the face. The flexible display can be rolled or folded in an accordion like manner during storage in or near the arm, and can be extended from one side of the headwear to the other side over the face. Once extended, the flexible and clear display can render images as part of VR/AR/XR operation.

To be discrete, the housing for the motor/electronics can be behind the head.

The chamber can have displays to provide virtual, augmented, or extended reality (VR/AR/XR) views.

The chamber can have audio and haptic feedback actuators.

For VR, the chamber can have a moveable door over the display to block external views.

For AR/XR, the display can be flexible and foldable OLED displays, or to save power, can be unicolor e-ink displays.

To save power, the display can be colored icons on a side of the display.

The chamber can simulate wind by controlling airflow

The chamber can simulate mist by using a micropump or inkjet pump that spreads droplets of water to the user's face or body. The water can be cooled or heated using suitable resistive temperature actuators for example.

The chamber can include air filter and can have built-in air disinfectant using UVC LEDs, for example. Optional disposable air filter such as N95 filters can be used.

The chamber can be a pivotable and extendable to adjust the view.

The chamber can be a hood with neck air seal to isolate the air breathed by the user from ambient air.

The chamber can be portable headworn devices that receive air from portable hood, cap, mask, headsets, and other wearable items.

An oxygen cartridge can be coupled to the chamber to supply air in case of fire.

FIG. 4A shows an exemplary plane interior, while FIGS. 4B-4H show various embodiments of a hood or mask for airplane or train travelers, among others. Various options are shown in FIG. 4B, for example hood based or cap-based PPE. These hoods/masks provide isolated air interiors with filtered and clean air for passenger protection. A drape connects the bottom of the hood assembly to the traveler's clothing and provides a sealed environment for breathing. Optionally the hood provides infotainment via flexible screens such as OLED displays or projectors that can project on the screens. The air flow and air temperature are controlled using suitable motors and heaters and the air distribution system is not shown in detail since there are known many suitable embodiments. The specification of air flow/temperature can be adjusted by dials on the seat/hood or alternatively via a smart phone app in communication with the controller in box 18. The cabin chair provides in a variety of adjustable positions from full upright to semi-reclining. Mounted on chair and positioned above it is a hood. Hollow mounting column is affixed to the back of the chair and allows vertical movement of the hood with respect to the chair to comfortably accommodate subjects of varying body proportions and height. The chair is formed with recesses containing air columns to supply and remove air from the user. The hood extends from the seat and preferably covers the lower rear portion of the head and the neck and provides better air seal. The hood has a means of selectively diverting a controllable portion of the heated air flowing into hood and directing this air through the vents in the chair back so as to produce a relaxing and therapeutic effect on the subject. A desired portion of drying air flowing through air duct can be diverted into the chair back cavity, through vents and against the user's back and shoulders providing a soothing and relaxing effect. Vents surround the user's body sucks air away from the user and sucks down a suitable blanket, pad, or sealing polyester cloths to keep cabin air outside of the hood. A chair control permits the user to adjust the chair in any one of a range of positions from fully upright to semi-reclining. Other features such as a lower back massaging unit or helmet stereo headphones can be included for added comfort and relaxation and the additional controls located on the chair arms. The control can be Bluetooth enabled so that a mobile app can adjust the chair to fit the user needs. In one embodiment, a clear shield rises from the top of the seat to the cabin ceiling in each row to prevent coughing from one row to reach adjacent rows of seats. Each row has optional disinfectant system such as UVC disinfectant LEDs that can be activated by a cleaning crew to kill pathogens on the surfaces of reach row, and a display can show the passenger the disinfectant status.

FIG. 4B shows an exemplary hood that drops down from the cabin ceiling while FIG. 4C shows a seat mounted hood. These embodiments can be used with the standard oxygen air mask or as a substitute for the aircraft emergency oxygen systems or air masks. In regular flight operation, the hood or mask can provide filtered air to passengers, and oxygen can flow when the cabin pressurization system fails, and the cabin altitude has climbed above a safe level. The hood/masks are stored in compartments near passenger seats and near areas like lavatories and galleys, and during an emergency can transfer an oxygen source, like a centralized gaseous cylinder or decentralized chemical oxygen generator. One embodiment of the hood has a semi-oval or semi-egg-shaped top portion with a top connected to the gas supply on the cabin ceiling so that the user can sit down and then pull down the hood to a comfortable position and lock in the hood position. The hood has a middle clear shield portion or face mask so that the user can see. One embodiment shown in FIG. 4D provides a hood with a moveable facemask or shield whose position is user adjustable. Such configuration is also good for displaying AR/VR images The middle shield portion can be clear plastic, or can be an OLED display, or can be a display OLED with user controllable transparency so that the user can darken the hood if s/he wishes to sleep. At the bottom of the middle shield portion is a removable polyester fabric that acts as an air filter. Removability can be affected by a zipper or Velcro connection, for example. The polyester fabric can include a weighted bottom so that the fabric provides a good air seal between the hood interior and the cabin air. For example, the bottom can be like a lead apron in dental X-Ray sessions that is flexible yet provides a weight to seal the apron to the user's clothing. Alternatively, the weighted polyester apron can be a cape, a poncho, a shoulder pad, or any suitable shapes to provide a sealed connection from the bottom of the middle shield portion/facemask to the user's clothing, as shown in FIG. 4E.

An optional air return (or air suck-up) tube can be provided to further isolate the interior of the sealed air region inside the hood assembly and the cabin air. Various ports are used for admission of atmospheric air into the interior of the hood. The ports can be provided in an end wall, in a front wall and in two lateral walls of the hood. Streamlets of air which enter the interior of the housing through such ports are caused to flow into a discrete (separately produced) tubular or frustoconical guide which induces the streamlets to flow toward the impeller of an air conveying unit. The impeller is driven by an electric motor and causes the air to flow into an extension of the hood on its way into the plenum chamber. A suitable air heating unit is provided in the housing to raise the temperature of air to a desired level upstream of the plenum chamber.

FIG. 4F shows an expandable hood, while FIG. 4G shows an inflatable embodiment. The hood has an outer panel whose front part defines an opening for the face, nose, mouth, eyes and chin of the user, and a foraminous inner panel having perforations in the form of pores or the like. When not in use, the hood can be collapsed into a minute package ready to be confined in the seat top, preferably connected to the plane's air supplying apparatus which supplies air to keep the hood in expanded or inflated condition and also breathing air to the user via the foraminous inner panel. At the bottom of the hood is a removable polyester fabric that acts as an air filter. Removability can be affected by a zipper or Velcro connection, for example. The fabric can include a weighted bottom so that the fabric provides a good air seal between the hood interior and the cabin air. An optional air return (or air suck-up) tube can be provided to further isolate the interior of the sealed air region inside the hood and the cabin air. During an emergency, as detailed below, oxygen can be sent to the air inlets of the hood and otherwise the standard filtered air generated by the aircraft is provided for breathing and/or hood inflation, for example.

One embodiment subdivides the side wall of the hood into longitudinal cells which terminate in a central distribution chamber at the apex of the hood, above which the housing containing the motor-driven blower in box 18, protruding partly into the distribution chamber and located coaxially with respect to the hood axis, is mounted in such a manner that, during use, it supports its weight which is reduced by the upward force of the air cushion formed in the distribution chamber when the hood is inflated, above the hair on its bottom surface and on the inner jacket of the hood. Due to the coaxial mounting of the housing containing the motor-driven blower with respect to the hood axis, the hood is in balance on the head so that additional means of fastening, such as bands tied around the chin, are not necessary and free lateral space between inner jacket and hair or head as in solid hoods, is gained. In addition, the housing containing the motor-driven blower is supported over the hair on the air cushion by a larger surface so that no disagreeable pressure is exerted on the head. According to the invention, the motor-driven blower is of the radial type on whose thrust face at least one heating coil is mounted, in the plane of the impeller and coaxially with respect to it. In this manner, the motor-driven blower and the housing may be made flat.

After the motor is switched on, air is suctioned through air intake openings connected to the cabin air supply inlet, heated by a heating coil, and forced into the space formed by the outer and inner jacket. The air inflates the hood while forming an air cushion in the distribution chamber, and flows onto the hair to be dried, through the openings provided in the inner jacket. The motor-driven blower supports itself on the air over the air cushion formed in the distribution chamber. This air cushion produces stabilization of the apex of the hood as well as an ideal airflow transfer into the lateral cells.

Another aspect can be a cabin with individual air chamber with an exterior and air distribution channels that deliver air toward the user in interior portion. The air chamber can extend from the PSU, the wall, or the ceiling of the cabin. Another embodiment can extend from the seat. The user can pull on the unit to extract it from its storage location and guide it over the head. At the bottom of the chamber, a drape can connect the chamber to the user's chest, shoulder, or body to provide a semi-sealed environment from the drape to the chamber. The drape can be a fabric that is multiple folded to keep out pathogens, yet enable the user to easily and comfortably enter/exit the chamber.

Variations of the chamber can be:

The chamber can have a hood with an exterior portion, air channels distributed along the perimeter of the exterior, and an interior portion with a plurality of air openings facing the user.

The chamber can be inflatable, with airflow channels and openings facing the user to deliver fresh breathable air to the user. An exit channel or tube can be positioned at the bottom of the chamber or near the mouth of the user with a pump to remove used air away from the user.

The chamber can have a drape that sealably and removably attach the bottom of the chamber to user clothing. This can be weighted flexible fabric such as polyester fabric that acts as an air filter. Removability can be affected by a zipper or Velcro connection, for example. The fabric can include a weighted bottom so that the fabric provides a good air seal between the hood interior and the cabin air.

The chamber can have foldable or inflatable components to reduce the size of the chamber when not used.

The chamber can be a helmet covering the entirety of the user face down to the neck level. A rubber with weighted bottom can provide an air seal between the user's shoulder and the helmet so that clean air from the cabin air filter is precisely delivered to the user's nose/mouth for breathing and any virus dispersed by droplets cannot get to the user eye, nose or mouth.

The chamber can have heating or cooling circuits to adjust temperature of air delivered to the user.

The chamber can include a flexible transparent/translucent OLED display in front of the eyes. A processor and data storage device can render images on the display to entertain the user. The processor can have a low latency transceiver such as an ultrawideband (UWB) transceiver to receive data quickly. Additionally, the processor can offload compute intensive processors to nearby edge processors over the UWB connection and as a result reduces the battery size needed and increase device uptime prior to recharging.

To be discrete, the housing for the motor/electronics can be behind the head.

The chamber can have displays to provide virtual, augmented, or extended reality (VR/AR/XR) views.

The chamber can have audio and haptic feedback actuators.

For VR, the chamber can have a moveable door over the display to block external views.

For AR/XR, the display can be flexible and foldable OLED displays, or to save power, can be unicolor e-ink displays.

To save power, the display can be colored icons on a side of the display.

The chamber can simulate wind by controlling airflow

The chamber can simulate mist by using a micropump or inkjet pump that spreads droplets of water to the user's face or body. The water can be cooled or heated using suitable resistive temperature actuators for example.

The chamber can include air filter and can have built-in air disinfectant using UVC LEDs, for example. Optional disposable air filter such as N95 filters can be used.

The chamber can be a pivotable and extendable to adjust the view.

The chamber can be a hood with neck air seal to isolate the air breathed by the user from ambient air.

The chamber can be portable headworn devices that receive air from portable hood, cap, mask, headsets, and other wearable items.

An oxygen cartridge can be coupled to the chamber to supply air in case of fire.

FIG. 4C shows an exemplary seat mounted hood with an arm extending from the seat top. The hood has a semi-oval or semi-egg-shaped top portion with a base connected to the extendable and pivotable arm so that the user can lift the hood above the head prior to sitting down, then the user can lower the hood to a comfortable position and lock in the hood position. The hood has a middle clear shield portion or face mask so that the user can see. The middle shield portion can be clear plastic, or can be an OLED display, or can be a display OLED with user controllable transparency so that the user can darken the hood if s/he wishes to sleep. At the bottom of the middle shield portion is a removable polyester fabric that acts as an air filter. Removability can be affected by a zipper or Velcro connection, for example. The fabric can include a weighted bottom so that the fabric provides a good air seal between the hood interior and the cabin air. An optional air return (or air suck-up) tube can be provided to further isolate the interior of the sealed air region inside the hood assembly and the cabin air. A number of ports are used for admission of atmospheric air into the interior of the hood. The ports can be provided in an end wall, in a front wall and in two lateral walls of the hood. Streamlets of air which enter the interior of the housing through such ports are caused to flow into a discrete (separately produced) tubular or frustoconical guide which induces the streamlets to flow toward the impeller of an air conveying unit. The impeller is driven by an electric motor and causes the air to flow into an extension of the hood on its way into the plenum chamber. A suitable air heating unit is provided in the housing to raise the temperature of air to a desired level upstream of the plenum chamber.

In an inflatable embodiment, the hood has an outer panel whose front part defines an opening for the face, nose, mouth, eyes and chin of the user, and a foraminous inner panel having perforations in the form of pores or the like. When not in use, the hood can be collapsed into a minute package ready to be confined in the seat top, preferably connected to the plane's air supplying apparatus which supplies air to keep the hood in expanded or inflated condition and also breathing air to the user via the foraminous inner panel. At the bottom of the hood is a connection fabric connecting the user to the hood bottom in a manner that does not allow virus to easily enter the user, yet the connection fabric allows the user flexibility in entering/exiting the chamber. The connection fabric can be removable polyester fabric that has a plurality of layers which act as an air filter. Removability can be affected by a zipper or Velcro connection, for example. The fabric can include a weighted bottom or a magnetic latch that snappably secures the fabric to corresponding magnets placed on user clothing so that the fabric provides a good air seal between the hood interior and the cabin air. An optional air return (or air suck-up) tube can be provided to further isolate the interior of the sealed air region inside the hood and the cabin air.

The hood can be adjusted as to the height and the reach/extension over the user head. One embodiment provides a height adjustment of the hood assembly, as by telescoping the sections, to position the hood assembly by height and by the distance to the head from the seat so that it is comfortable for the user. For example, the section to adjust the height and the section to adjust the reach can be on track means to allow relative movement between the two sections. The first section is movable vertically up and down relative to the base assembly for adjusting the height of the hood assembly when in the elevated position. The first section is movable vertically in and out relative to the base assembly for adjusting the reach of the hood assembly when in the elevated position.

FIG. 4D shows an exemplary hood with a face mask. The facemask may be attached to the hood by left and right attachment arms which may be pivotally affixed to the hood and the face mask at pivot points which can use any suitable pivotal type attachment. A second pivot point may additionally serve to pivotally attach the hood to the hood-to-cabin arm or to a hood-to-seat arm. Attachment arm may be a single, rigid member in a preferred embodiment for the purpose of decreased cost of manufacture. However, it is possible to construct the attachment arm with a plurality of pivotally attached rigid members, or a malleable, semi-rigid member in order to enable the face mask to be placed at the position desired by the operator or user to cover the hood. The hood can extend to contact the collar bone and can have a rubber sheet or apron to provide an air seal for the user's head in the hood. Suitable air pump, heater, and air tubing/piping are not shown.

In another aspect, the air chamber can have an openable face mask, and the chamber can have an exterior and air distribution channels that deliver air toward the user in interior portion. The air chamber can extend from the PSU, the wall, or the ceiling of the cabin. Another embodiment can extend from the seat. The user can pull on the unit to extract it from its storage location and guide it over the head. At the bottom of the chamber, a drape can connect the chamber to the user's chest, shoulder, or body to provide a semi-sealed environment from the drape to the chamber. The drape can be a fabric that is multiple folded to keep out pathogens, yet enable the user to easily and comfortably enter/exit the chamber.

Variations of the chamber can be:

The chamber can have a hood with an exterior portion, air channels distributed along the perimeter of the exterior, and an interior portion with a plurality of air openings facing the user.

The chamber can be inflatable, with airflow channels and openings facing the user to deliver fresh breathable air to the user. An exit channel or tube can be positioned at the bottom of the chamber or near the mouth of the user with a pump to remove used air away from the user.

The chamber can have a drape that sealably and removably attach the bottom of the chamber to user clothing. This can be weighted flexible fabric such as polyester fabric that acts as an air filter. Removability can be affected by a zipper or Velcro connection, for example. The fabric can include a weighted bottom so that the fabric provides a good air seal between the hood interior and the cabin air.

The chamber can have foldable or inflatable components to reduce the size of the chamber when not used.

The chamber can be a helmet covering the entirety of the user face down to the neck level. A rubber with weighted bottom can provide an air seal between the user's shoulder and the helmet so that clean air from the cabin air filter is precisely delivered to the user's nose/mouth for breathing and any virus dispersed by droplets cannot get to the user eye, nose or mouth.

The chamber can have heating or cooling circuits to adjust temperature of air delivered to the user.

The chamber can include a flexible transparent/translucent OLED display in front of the eyes. A processor and data storage device can render images on the display to entertain the user. The processor can have a low latency transceiver such as an ultrawideband (UWB) transceiver to receive data quickly. Additionally, the processor can offload compute intensive processors to nearby edge processors over the UWB connection and as a result reduces the battery size needed and increase device uptime prior to recharging.

To be discrete, the housing for the motor/electronics can be behind the head.

The chamber can have displays to provide virtual, augmented, or extended reality (VR/AR/XR) views.

The chamber can have audio and haptic feedback actuators.

For VR, the chamber can have a moveable door over the display to block external views.

For AR/XR, the display can be flexible and foldable OLED displays, or to save power, can be unicolor e-ink displays.

To save power, the display can be colored icons on a side of the display.

The chamber can simulate wind by controlling airflow

The chamber can simulate mist by using a micropump or inkjet pump that spreads droplets of water to the user's face or body. The water can be cooled or heated using suitable resistive temperature actuators for example.

The chamber can include air filter and can have built-in air disinfectant using UVC LEDs, for example. Optional disposable air filter such as N95 filters can be used.

The chamber can be a pivotable and extendable to adjust the view.

The chamber can be a hood with neck air seal to isolate the air breathed by the user from ambient air.

The chamber can be portable headworn devices that receive air from portable hood, cap, mask, headsets, and other wearable items.

An oxygen cartridge can be coupled to the chamber to supply air in case of fire.

Referring now to the drawings in greater detail, FIG. 4E shows a hood assembly pivotally mounted atop a head mounting assembly. The lower portion of head mounting assembly forms an impeller housing received within a base unit. The head assembly includes an upper cover or shell portion, and the exterior wall portion of a somewhat elongated generally annular drying air distribution plenum. The head assembly has a movably mounted cover surrounding a plenum and an air flow control system is mounted for pivotal movement about a portion of a plenum disposed atop the head mounting unit, the lower portion of which also includes an impeller and a motor housing and which is pivotally attached to a base unit. In the preferred construction, air is taken in through openings in the base, and is directed by the impeller upwardly through the head support element past an air heater in the head mounting unit for distributing about the periphery of the head within the annular plenum and vents outwardly from the interior of the head under the control of the adjustable cover vents. For storage and transportation, the cover or shell portion of the head is moved downwardly to a position closely overlying the plenum, the mounting unit pivoting relative to the base as well as to the head assembly, to permit both the base and the head mounting unit to be received within the head assembly and retained therein. For storage after a trip, the cover or shell portion of the head is moved downwardly to a position closely overlying the plenum, the mounting unit pivoting relative to the base as well as to the head assembly, to permit both the base and the head mounting unit to be received within the head assembly and retained therein.

FIG. 4F shows an exemplary collapsible hood. The hood has two foldable semicircular halves on either side of a thin support hook frame which is sized to comfortably cover the user's head. The frame can be nestled into the top of the seat, and the frame can be telescopically raised high when the user sits down, and then the frame can be lowered into a comfortable position for the user and locked/secured into place. Each side of the frame consists of a lower semicircular bow which is a foldable part, for instance, of a soft plastic and a semicircular plate hinged to the frame. When folded into the frame for storage, the parts are swung inwardly the soft material and forms a flat case requiring a minimal of storage space. A motor-fan-unit draws dry air through air intake ducts, and a suction fan with a fan blade sucks in filtered air through inlet. The sucked-in air can be cooled or heated by suitable air conditioner (heater or air cooler). From this duct the air escapes through a plurality of openings into the collapsible hood. In one embodiment, all or part of the inner three walls of the frame can be provided with apertures as slots which distribute the air within the hood relatively uniformly in all directions. In another embodiment, in place of the foldable bow, a collapsible hood can be used. In or at the hood top formed of an inflatable shell is a connector to the seat or cabin ceiling where air from the cabin is used for blowing up air chambers of the hood so that this hood will be erected and constitute a comparatively shape-unvarying hood body which on its inner side has a plurality of nozzle orifices from which a filtered air stream is issued in the direction of the interior of said hood. During use, the collapsible hood is inflated to the proper comfort level, and the hood bottom can be connected to the user's clothing to provide an air seal and filtered air can be provided to the sealed hood.

FIG. 4G shows a disposable hood embodiment to avoid sharing the hood and provide protection from prior user contamination of the hood. This embodiment is foldable and can be compacted for storage in the PSU or alternatively in the seat pocket. One embodiment has a plurality of guide structures in the disposable hood which allow the disposable hood to take form as an oval shape over the head when inflated. The guide structures can be two bendable elongated bars that move from a stored position that overlaps the guide structures to a deployed position where the guide structures are moved to a position perpendicular to each other. Another embodiment provides a clear bag with three closed sides forming a protective bubble enclosure and sealed to have only a single opening that will fit over any persons head, the opening being provided with a drawstring to permit quick closing of the bag about the neck of the wearer as well as quick removal. The clear bag is attached to the air supply of the airline cabin, and exhausted air is attached to air exhaust pipe of the cabin. The opening is of such a size that not only will allow air to easily enter the hood but also permit the wearer to place it over his head. Surrounding the opening is a drawstring having each of its ends extending freely exteriorly of the hood so that they may be easily grasped. The drawstring is slidable with a sleeve formed by integrally securing an elongated strip circumferentially on the exterior of the hood or by providing suitable loops on the surface of the hood to hold the string. The drawstring is thus capable of being closed and tied about the wearer's neck to substantially hermetically close the opening. The hood may be made of any material not porous to smoke or harmful gases. The material is preferably any convenient plastic and should be thin to be light in weight and substantially transparent to allow the wearer to see clearly no matter how the hood is placed over the head. The open end may be provided with a reinforcing strip providing a collar. Thus, the drawstring may be secured better and less likely to cut the neck of the user. The drawstring may be replaced by a hook and loop fastener such as Velcro or other tie means. The Fabric can be 3.5 Mil Low Density Polyethylene with Barrier Film, heat sealed on all sides including drawstrings or elastic area. The bag may be formed by one or two pieces of nylon, plastic, polyethylene that will be head welded as a seam on top and sides of the bag and will create permanent bond. Gussets on top and on sides may be utilized to maximize air reservoir and to increase the rigidity of the bag to enable to stay erect. A flexible material may be inserted at the seamed edges to further enhance the firm structure keeping it in a preferred upright position.

In a further aspect, the air chamber can have an openable face mask, and the chamber can have an exterior and air distribution channels that deliver air toward the user in interior portion. The air chamber can extend from the PSU, the wall, or the ceiling of the cabin. Another embodiment can extend from the seat. The user can pull on the unit to extract it from its storage location and guide it over the head. At the bottom of the chamber, a drape can connect the chamber to the user's chest, shoulder, or body to provide a semi-sealed environment from the drape to the chamber. The drape can be a fabric that is multiple folded to keep out pathogens, yet enable the user to easily and comfortably enter/exit the chamber.

Variations of the chamber can be:

The chamber can have a hood with an exterior portion, air channels distributed along the perimeter of the exterior, and an interior portion with a plurality of air openings facing the user.

The chamber can be inflatable, with airflow channels and openings facing the user to deliver fresh breathable air to the user. An exit channel or tube can be positioned at the bottom of the chamber or near the mouth of the user with a pump to remove used air away from the user.

The chamber can have a drape that sealably and removably attach the bottom of the chamber to user clothing. This can be weighted flexible fabric such as polyester fabric that acts as an air filter. Removability can be affected by a zipper or Velcro connection, for example. The fabric can include a weighted bottom so that the fabric provides a good air seal between the hood interior and the cabin air.

The chamber can have foldable or inflatable components to reduce the size of the chamber when not used.

The chamber can be a helmet covering the entirety of the user face down to the neck level. A rubber with weighted bottom can provide an air seal between the user's shoulder and the helmet so that clean air from the cabin air filter is precisely delivered to the user's nose/mouth for breathing and any virus dispersed by droplets cannot get to the user eye, nose or mouth.

The chamber can have heating or cooling circuits to adjust temperature of air delivered to the user.

The chamber can include a flexible transparent/translucent OLED display in front of the eyes. A processor and data storage device can render images on the display to entertain the user. The processor can have a low latency transceiver such as an ultrawideband (UWB) transceiver to receive data quickly. Additionally, the processor can offload compute intensive processors to nearby edge processors over the UWB connection and as a result reduces the battery size needed and increase device uptime prior to recharging.

To be discrete, the housing for the motor/electronics can be behind the head.

The chamber can have displays to provide virtual, augmented, or extended reality (VR/AR/XR) views.

The chamber can have audio and haptic feedback actuators.

For VR, the chamber can have a moveable door over the display to block external views.

For AR/XR, the display can be flexible and foldable OLED displays, or to save power, can be unicolor e-ink displays.

To save power, the display can be colored icons on a side of the display.

The chamber can include a phone clip support in front of the eye so that the user can use a smart phone to render video in place of a dedicated display on the chamber to save cost and still provide entertainment. One embodiment allows the smart phone to control the operations of the chamber including chamber temperature, humidity, wind level, scent change, among others.

The chamber can simulate wind by controlling airflow, and fragrance can be added to the air flow.

The chamber can simulate mist by using a micropump or inkjet pump that spreads droplets of water to the user's face or body. The water can be cooled or heated using suitable resistive temperature heaters and thermoelectric coolers/Peltier Junction/water evaporation cooling, for example.

The chamber can include air filter and can have built-in air disinfectant using UVC LEDs, for example. Optional disposable air filter such as N95 filters can be used.

The chamber can be a pivotable and extendable to adjust the view.

The chamber can be a hood with neck air seal to isolate the air breathed by the user from ambient air.

The chamber can be portable headworn devices that receive air from portable hood, cap, mask, headsets, and other wearable items.

The chamber can apply UVC radiation to kill pathogens entering the breathable air. Such UV LED is inside of a UV shield to protect the user from errant radiation that can harm skin/eye.

An oxygen cartridge can be coupled to the chamber to supply air in case of fire.

Figure 4H:
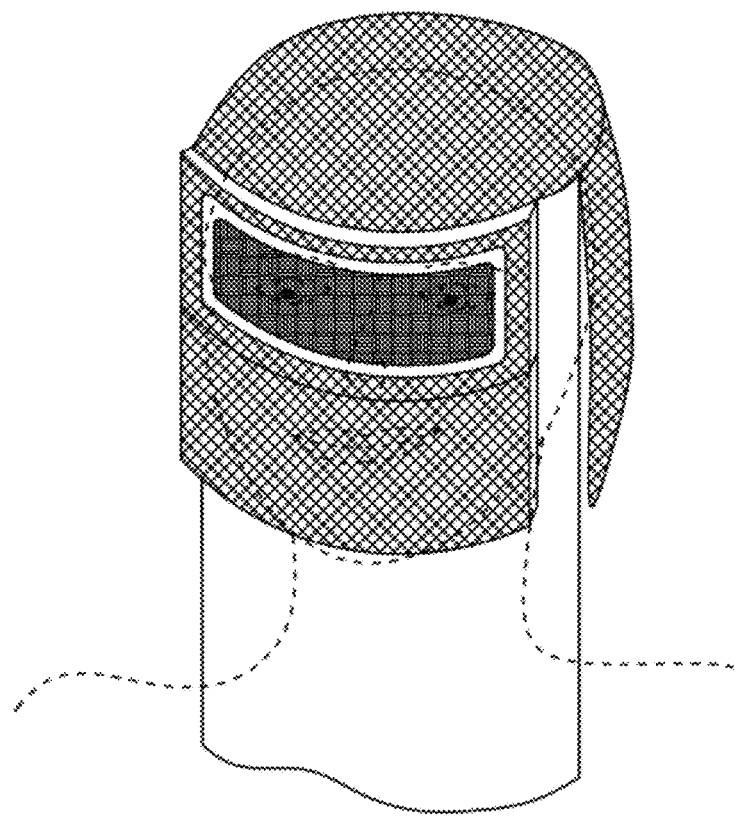

FIG. 4H shows an exemplary AR/VR/XR embodiment with a head worn gear. The headgear can provide a glass in front of the eye in one embodiment. The headgear can also mount a cell phone in front of the eyes via suitable phone clips and the phone can run an AR/VR/XR app. The device includes a cover for the eye, nose and lip. The cover is attached to an air filter unit with a motor, a disinfectant unit (such as a shielded UV C LED to expose pathogens to UV C). Optionally, the air filter unit includes an air fragrance unit with one or more fragrance disposables that can render specific scents on demand. For example, the fragrance can be an ocean fragrance that can be dispensed when the AR/VR scene is for an ocean trip. In scenes of a rose garden, the fragrance can be the smell of rose dispensed or mixed from one or more disposable fragrance units. The unit simulates hundreds of smells to immerse the user into virtual world. For example, the unit can provide the smell of burning rubber in a racing game when the pedal is pressed, or the gunpowder odor in a game with guns.

The unit uses a thermal scent generator which can be a resistive heater that warms up the supply cartridge and provides the aroma to the user via the air vents/tubing in the hood or headworn gear. One embodiment is based on the same hardware as vaping devices, and uses basically the same liquid as e-cigarettes, albeit without nicotine. The unit holds an array of replaceable cartridge, containing individual aroma capsules, that are user replaceable. Distinct scents accurately simulate the atmosphere of games and movies. The aromas are safe to inhale and are similar to those used in the food industry. In other embodiments, a water mist can be dispensed to simulate rain, heat can be provided to the hood to simulate the desert, wind can be simulated by increasing air flow, and vibration can be dispensed via the force feedback haptic motors and/or the bone conduction hearing system. The system can be used to provide personal aromatherapy device at any time. The hood/mask can help users immerse into a perfect state of relaxation with selected aroma setting and drift away from stress.

In a further aspect, a reality head gear can include a head gear with a chamber that sealably encloses the air in contact with the eyes and the mouth. The chamber has an air inlet with a filter that protects the user from pathogens in the outside air. The filter can be N95 type filter, and may have an ultraviolet C type LED to kill pathogens. Air exhaled by the user is fed back to the filter to be mixed with fresh air rather than be released to the environment to protect nearby people from accidental coughing or other droplet dissemination by the user to the ambient environment. Thus, the unit protects both the user and nearby people from pathogen.

Variations of the headgear type chamber can be:

The headgear can be a portable hood, cap, mask, headsets, and other wearable item with a chamber.

The chamber can be inflatable, with airflow channels and openings facing the user to deliver fresh breathable air to the user. An exit channel or tube can be positioned at the bottom of the chamber or near the mouth of the user with a pump to remove used air away from the user.

The chamber can have foldable or inflatable components to reduce the size of the chamber when not used.

The chamber can be a helmet covering the entirety of the user face down to the neck level. A rubber with weighted bottom can provide an air seal between the user's shoulder and the helmet so that clean air from the cabin air filter is precisely delivered to the user's nose/mouth for breathing and any virus dispersed by droplets cannot get to the user eye, nose or mouth.

The chamber can have heating or cooling circuits to adjust temperature of air delivered to the user.

The chamber can include a flexible transparent/translucent OLED display in front of the eyes. A processor and data storage device can render images on the display to entertain the user. The processor can have a low latency transceiver such as an ultrawideband (UWB) transceiver to receive data quickly. Additionally, the processor can offload compute intensive processors to nearby edge processors over the UWB connection and as a result reduces the battery size needed and increase device uptime prior to recharging.

To be discrete, the housing for the motor/electronics can be behind the head.

The chamber can have displays to provide virtual, augmented, or extended reality (VR/AR/XR) views.

The chamber can have audio and haptic feedback actuators.

For VR, the chamber can have a moveable door over the display to block external views.

For AR/XR, the display can be flexible and foldable OLED displays, or to save power, can be unicolor e-ink displays.

To save power, the display can be colored icons on a side of the display.

The chamber can simulate wind by controlling airflow, and fragrance can be added to the air flow.

The chamber can simulate mist by using a micropump or inkjet pump that spreads droplets of water to the user's face or body. The water can be cooled or heated using suitable resistive temperature heaters and thermoelectric coolers/Peltier Junction/water evaporation cooling, for example.

The chamber can include air filter and can have built-in air disinfectant using UVC LEDs, for example. Optional disposable air filter such as N95 filters can be used.

The chamber can be a pivotable and extendable to adjust the view.

The chamber can be can plug into and receive air from sources such as a cabin air supply vent or a room air supply vent if one is available to reduce power consumption on the portable air filter/UV LED.

The chamber can apply UVC radiation to kill pathogens entering the breathable air. Such UV LED is inside of a UV shield to protect the user from errant radiation that can harm skin/eye.

An oxygen cartridge can be coupled to the chamber to supply air in case of fire.

The above systems when used in an aircraft can provide supplemental oxygen suitable for breathing as a standalone device. The device includes a small oxygen storage vessel for storing high pressure gaseous oxygen that preferably is sealed by a pressure seal to prevent flow from the oxygen storage vessel until the pressure seal is broken. The pressure seal may, for example, be a rupture disc formed of frangible material capable of being fractured to open the oxygen storage vessel and initiate the flow of oxygen from the oxygen storage vessel. A manifold is connected in fluid communication with the oxygen storage vessel and a pressure regulator that is connected in fluid communication with the manifold to receive the flow of oxygen at the high, first oxygen pressure from the oxygen storage vessel through the manifold. The pressure regulator is configured to deliver the flow of oxygen at a second oxygen pressure lower than the first oxygen pressure. In a presently preferred aspect, the second oxygen pressure is 16 psig. In a presently preferred aspect, the pressure seal is disposed in the manifold. One or more flow control valves are connected in fluid communication with the pressure regulator, and a flow controller is connected to the one or more flow control valves to control the operation of the one or more flow control valves. The flow controller typically is configured to rapidly supply oxygen at an initial altitude, such as 30,000 ft. or greater, for example, and throughout at least a portion of subsequent descent of the aircraft, such as above 10,000 ft., for example, typically for periods of approximately 12-22 minutes, for one or more persons, for example. The manifold includes an initiator configured to break the pressure seal to initiate a flow of oxygen from the oxygen storage vessel, and receives a flow of oxygen from the oxygen storage vessel at a first oxygen pressure. The initiator preferably includes a lance configured to mechanically break the rupture disc. Other devices for fracturing the rupture disc may alternatively be suitable, as long as an appropriate pressure seal can be maintained downstream of the oxygen storage vessel and opened as desired. An ambient cabin air pressure sensor connected to the flow controller and disposed within the container housing. The ambient cabin air pressure sensor is typically a transducer configured to detect the ambient cabin air pressure in the aircraft and generate an ambient cabin air pressure signal indicating the ambient cabin air pressure in the aircraft. The one or more flow control valves each have a flow control valve outlet, and receive and meter the flow of oxygen at the second oxygen pressure from the pressure regulator to one or more breathing hoods or masks as detailed above, each of which is connected to a corresponding flow control valve outlet, by metering small quantities of oxygen to the one or more breathing masks by a pulse oxygen system, in which the flow controller receives the ambient cabin air pressure signal from the ambient cabin air pressure sensor in the aircraft, and determines what quantity of oxygen is to be provided to the one or more breathing masks to control operation of the one or more flow control valves responsive to the ambient cabin air pressure signal. In a presently preferred aspect, the small quantities of oxygen that are metered to the one or more breathing masks that are less than that typically provided by a chemical oxygen generator, while an equivalent level of hypoxia protection is provided by the pulse oxygen system in aircraft decompression events. The pulse oxygen system typically adjusts an allotment of oxygen to each individual user as function of the user's actual demand for oxygen, such as according to a user's respiration rate, for example, wherein faster breathing results in a faster delivery rate of the user's oxygen allotments.

Figure 5A:
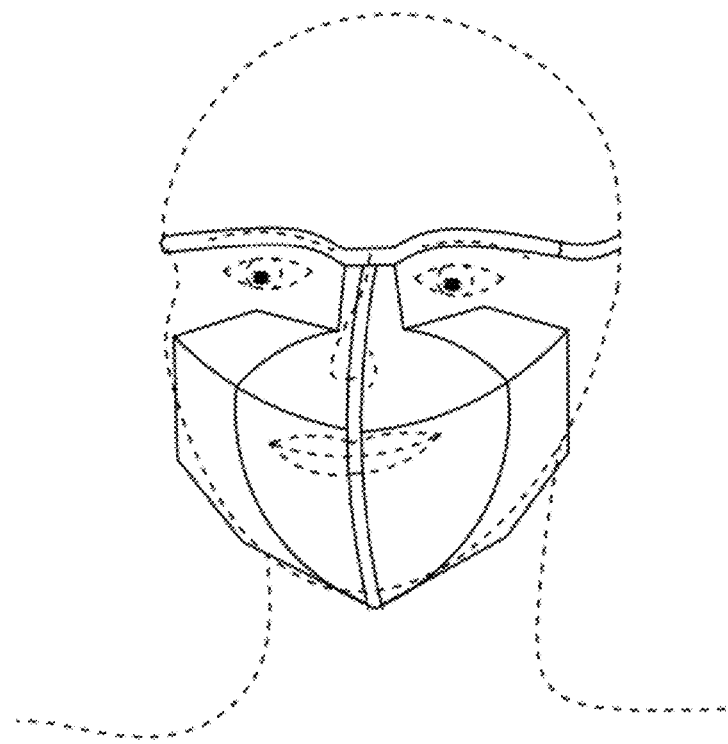
FIGS. 5A-5J show exemplary mobile embodiments of the air protection system.

FIGS. 5A-5J show exemplary PPE embodiments. In FIG. 5A, a top frame hooks on the wearer's ears to mechanically support a chamber covering the nose and mouth. An optional display can extend over the eyes for AR/VR/XR rendering. Power can be provided via a power back clipped on the belt or alternatively can be from a pack attached to the back of the head, for example.

Figure 5B:
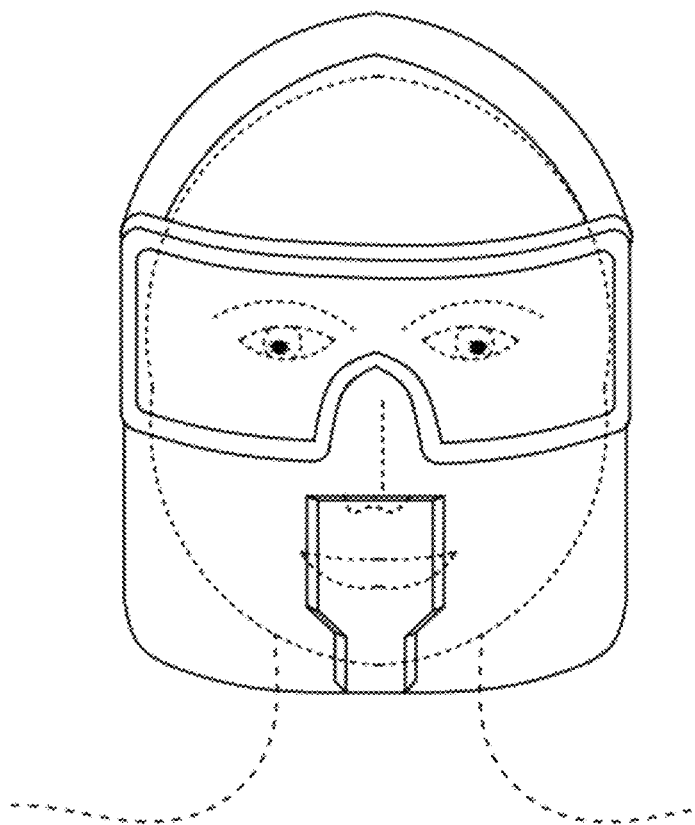
Figure 5C:
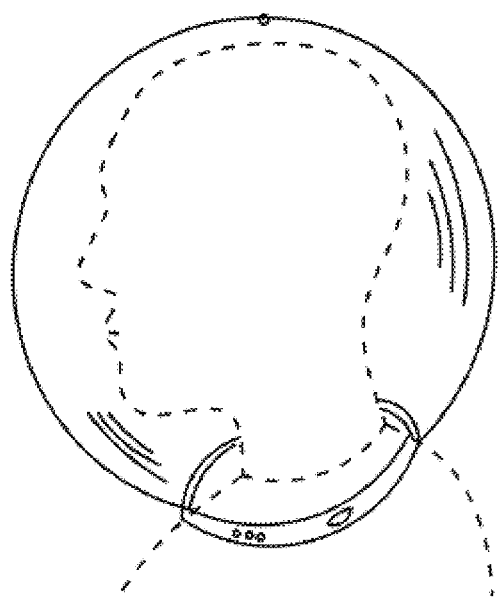
Figure 5D:
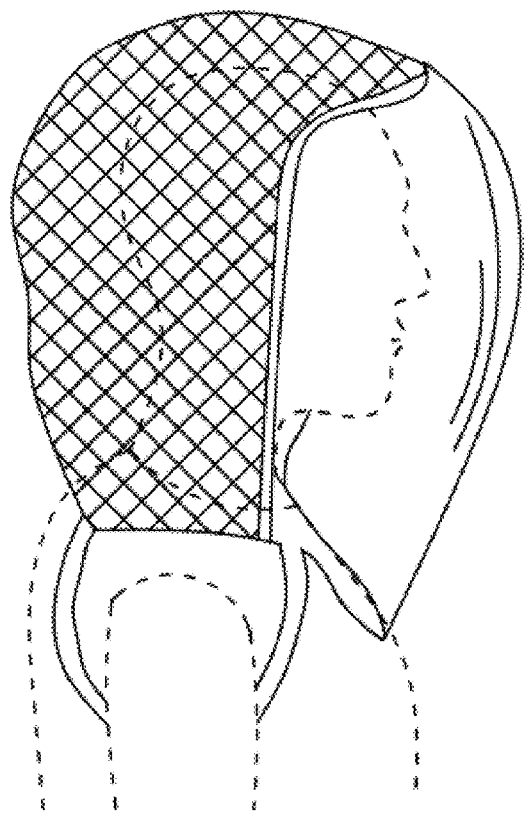
Figure 5E:
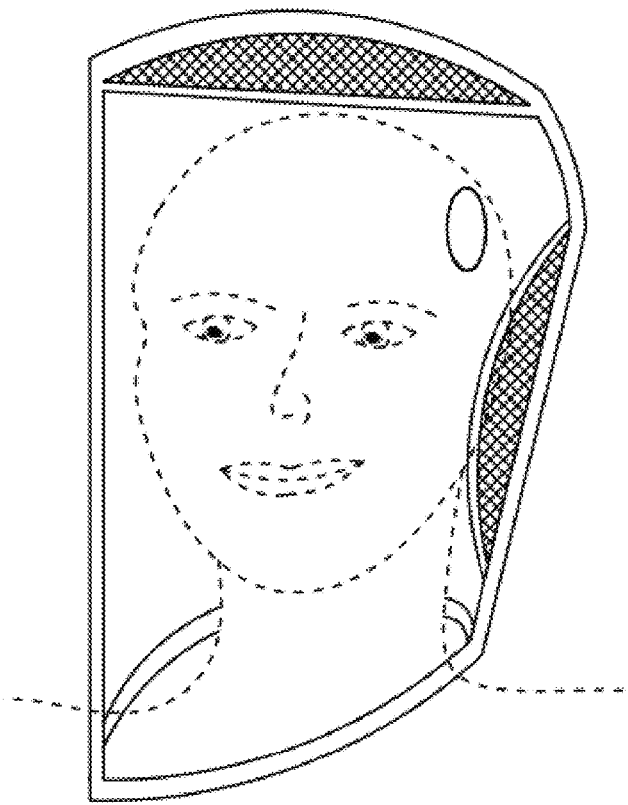
Figure 5F:
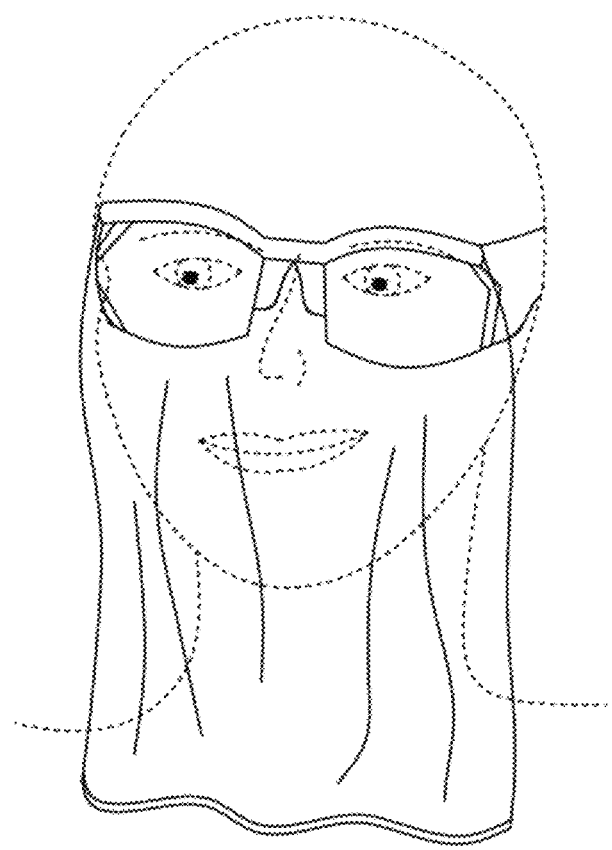
Figure 5G:
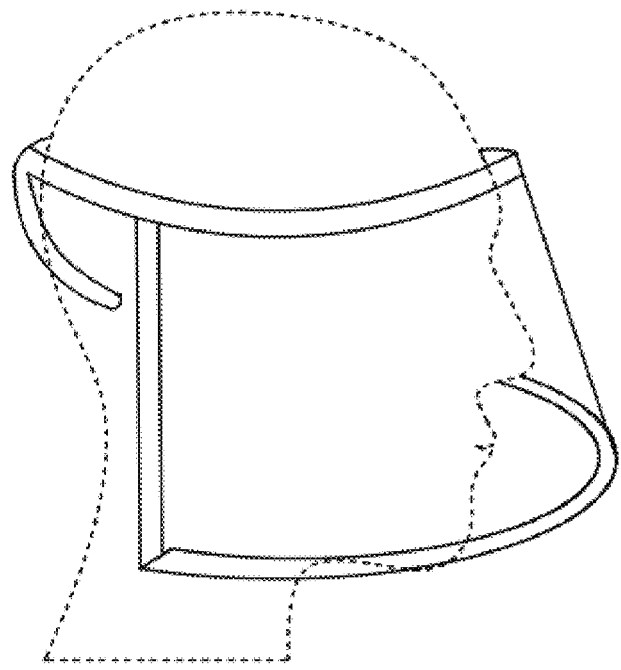
Figure 5H:
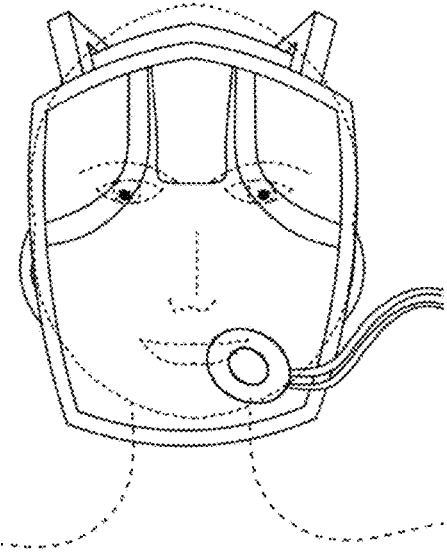
Figure 5I:
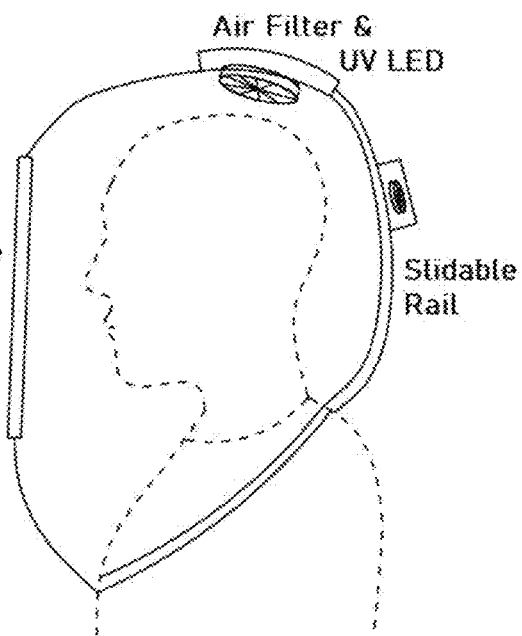
Figure 5J:
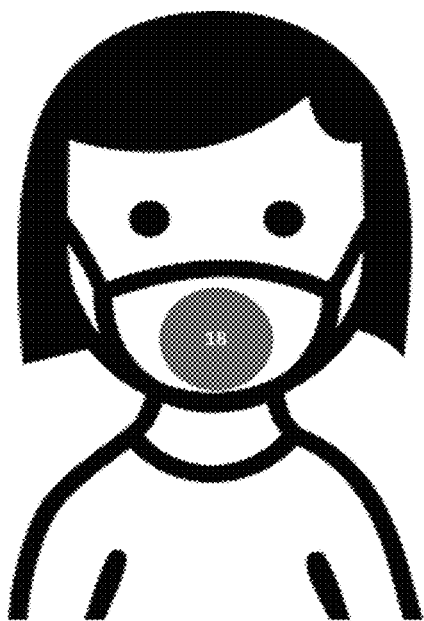

FIG. 5B shows a headset with mouth/nose protective chamber. FIG. 5C shows an astronaut like helmet PPE that circularly covers the head. FIG. 5D shows an elongated helmet where the clear viewing chamber extends past the shoulder down to the chest level. FIG. 5E shows a wedge shaped helmet. FIG. 5F shows an eye-glass embodiment with a flexible drape extending from the glass frames down to the user's neck or chest. The drape can be rolled into a small housing when not in use and when used, can be pulled down. To provide air seal, magnetic latches on the bottom of the drape can secure the drape to the wearer's clothing, and flexible bars can be bent to follow the facial/neck contours and provide a sealed environment in a discrete and comfortable manner. FIG. 5G shows another face mask embodiment, while FIG. 5H shows a face mask with a filtered air connection. FIG. 5I shows a helmet with an integrated unit including air filter and air disinfectant using UVC LEDs. Outside air is sucked in by the fan and directed through an opening where the UVC LED can shine through and kill pathogens. The air is then filtered and then fed to the interior of the helmet. The integrated unit can be moved along a slidable rail so that the user can adjust the placement of the unit as desired. A clear flexible display is provided at the front of the helmet to provide the user with computer assistance (such as in AR/VR/XR application, or navigation, or any medical/emergency information, for example). FIG. 5I shows another face mask embodiment covering the mouth and nose with the integrated unit including air filter/disinfectant. The mask version of FIG. 5I is small and can be pocketable in comparison with the helmet equivalent of FIG. 5I.

Methods are also disclosed. For example, a method of providing service to one or more occupants of an aircraft can include operating an aircraft having an air vent and a light. A flow of air can be provided through the vent. Power can be provided to the light. The light and the vent can be arranged as set forth herein.

Other methods include providing access to an interior region of an aircraft by an occupant and projecting a display of information onto a wall of the interior region. For example, an aircraft can have a projector positioned in a passenger service unit. The act of projecting a display can include operating the projector.

The system can include a chamber with an exterior portion, an interior portion, and air distribution channels in between and coupled to a filtered air source, wherein the channels deliver filtered air toward the interior portion; a clear panel coupled to the head housing; and a flexible connector coupled to the view panel and adapted to be secured to a body to provide a sealed environment and control entry of a pathogen outside the exterior portion. The system can include the following:

2 the air distribution channels are coupled to a seat, a cabin floor, or a cabin ceiling.

3 the chamber housing is foldable or inflatable and stored in a storage chamber in a wall, a seat, or a passenger service unit (PSU).

4. the connector comprises a rubber portion or a polyester drape coupling the chamber with a user chest, shoulder, or body to provide a semi-sealed environment to keep out pathogens.

5. an exit channel or tube positioned near a nose or mouth to remove exhaust air.

6. heating or cooling circuit to adjust a temperature of air delivery.

7. a flexible transparent display positioned in front of user eyes.

8. a low latency transceiver wirelessly coupled to a remote processor.

9. an ultrawideband (UWB) or 5G transceiver with low latency data communication.

10. an edge processor wirelessly coupled to the low latency transceiver, wherein the edge processor offloads compute intensive processing to reduce power consumption by a processor for the display.

11. a housing for control electronics on top of the chamber or on a side opposite to the clear panel.

12. the clear panel comprises a display to provide virtual, augmented, or extended reality (VR/AR/XR) views.

13. one or more audio and haptic feedback actuators.

14. the clear panel comprises a moveable shield or door.

15. the clear panel comprises a flexible and foldable OLED display or an e-ink display.

16. low-power icons on a side of the clear panel.

17. a motor to simulate wind in the chamber with generated airflow.

18. a water pump to simulate moisture, humidity, or mist in the chamber.

19. a pivotable and extendable arm coupled to the chamber to adjust the view.

20. an oxygen supply or cartridge to supply air in case of fire.

Also disclosed are aircraft. Also disclosed are other forms of transit, such as space craft, automobiles, trains, and boats. Such other forms of transit can include any one or more features of technologies disclosed herein.

Thus, incorporating the principles disclosed herein, it is possible to provide a wide variety of embodiments of the innovative principles described herein.

The system can operate with edge computing—moving computation and data storage away from large centers and relying more heavily on local storage and caching, with reduced energy footprints. One embodiment relies on transformers in the cellular base stations located near a mobile device (such as transformers running on a 5G base station in communication for surgical edge processing, among others).

Chatbots Treating Mental Issues

The COVID-19 pandemic and the resulting economic recession have negatively affected many people's mental health and created new barriers for people already suffering from mental illness and substance use disorders. As the pandemic wears on, ongoing and necessary public health measures expose many people to experiencing situations linked to poor mental health outcomes, such as isolation and job loss. To address these issues, chatbots as detailed below can be used with in home assistants such as Amazon Alexa to support patients. The chatbots can also be integrated into surgical robots to provide human touch, particularly in embodiments with mood detection.

In one aspect, a method to assist people in an infectious disease outbreak includes: providing a mobile fitness device to monitor and upload activity and vital sign to a fitness device server on a periodic basis; collecting daily health data from the fitness device server, collecting medical data for a person from a medical institution, and collecting infectious treatment data from predetermined sources including a government and a non-governmental organization (NGO); training a chatbot with a deep neural network with the collected data; and responding to a query by querying data from the mobile fitness device and retrieving an answer from the deep neural network based on vital sign and activity history. In another aspect, a system includes a mobile fitness device to collect exercise and vital signs from a user; and a chatbot to assist people in an infectious disease outbreak with a processor to: provide a mobile fitness device to monitor and upload activity and vital sign to a fitness device server on a periodic basis; collect daily health data from the fitness device server, collecting medical data for a person from a medical institution, and collecting infectious treatment data from predetermined sources including a government and a non-governmental organization (NGO); train a chatbot with a deep neural network with the collected data; and respond to a query by querying data from the mobile fitness device and retrieving an answer from the deep neural network based on vital sign and activity history.

Implementations of the above aspects may include one or more of the following additions to the above aspect:

2. training the deep learning machine with logically grouped or clustered data to provide context and biasing the answer based on the context.

3. grouping the data by age, sex, race, home location, health history, exercise history, family genetics, social economics, or risks for one or more diseases.

4. collecting recent data from mobile fitness devices, retrieving prior interactions with the user and prior health reports, and history of people in contact with the user.

5. collecting contract tracing data and training the deep neural network with the contact tracing data and data from people having contacts with a user.

6. capturing contract tracing data using ultra-wide-band (UWB).

7. determining a group or cluster best matching the person's health condition data and apply the customization information to bias the learning machine to generate a context-sensitive answer.

8. detect a user emotion during a chat and altering the answer based on the user emotion to provide empathy or to request professional help.

9. detecting emotion using a user facial expression or a verbal expression.

10. detects risks including suppressed immune system, a cancer condition, an organ transplant condition, infectious disease susceptibility, a healthcare work condition, an at-risk location.

11. collecting vital signs from mobile fitness device and detecting a core body temperature pattern, breathing pattern, coughing pattern, and walking/exercise patterns to detect changes indicative of an infectious disease.

12. detecting a breathing rate, a coughing pattern, a walking pattern, an exercise pattern.

13. detecting with the chatbot and the mobile fitness device fever or chills, cough, shortness of breath or difficulty breathing, fatigue, muscle or body aches, Headache, New loss of taste or smell, sore throat, congestion or runny nose, nausea or vomiting, diarrhea, breathing problem, chest pain or pressure, confusion during chat, ability to wake or stay awake, color change in a lip or a face.

14. detecting if a chronic condition needs treatment, and recommending treatment when treatment is suspended.

15. providing a rich text, a structured markup, a schema, microdata, or sematic tags on a web page for search engine optimization.

16. providing a ClaimReview Schema on a web page to improve trust in a disease recommendation.

17. receiving from a patient a narrative of a medical issue, generating one or more hypothesis and retrieving symptoms for each hypothesis, matching the symptoms with prior medical history; identifying one or more probable diagnosis based on the narrative and prior medical history; and probing the patient for confirmatory indications.

In another aspect, a chatbot can be used for determining an infection candidate, comprising: receiving C OVID trial enrollment criteria from a user including a combination of genetic variants for which a drug or therapy is likely to respond; searching a knowledge base of patient test information received from a plurality of independent entities for patients that match the trial enrollment criteria, wherein the knowledge base comprises an ontology data structure that identifies a causal relationship between a genetic variant and a phenotype based on a combination of the genetic variant and modifier variant information, wherein the knowledge base links the genetic variant and the modifier variant information, wherein the modifier variant information is based on curated evidence, and wherein the modifier variant information identifies whether modifier variants that modify a severity of the phenotype are likely to exist; and providing to the user search results for consented patients that match the trial enrollment criteria; wherein at least one of the receiving, searching, or providing are performed by one or more computers. In implementations, the test information comprises at least one of patient test information, patient sequence variant information, patient medical record information, patient location information, test site location information, patient phenotype information, and patient consent information.

Advantages of the medical chatbot includes one or more of the following. The bot enables healthcare companies and government entities to reach patients and audience directly. The bot answers questions in a realistic and with empathy through engaging use of personality, knowledge and display of empathy. The length of the agent's utterances is important in achieving better results with human evaluators. If they're too short, the responses are dull and communicate a lack of interest; if they're too long, the chatbot seems to waffle and not listen. The bots also use real time data from fitness monitoring devices such as smart watch and incorporate that information into the conversation and get timely assistance or care for the patient. The bot helps agencies save time and money on patient care. Patients and customers expect 24/7 availability, but they hate waiting on hold. They also ask many of the same questions over and over (and over) again. The bots greet potential customers, by identifying their needs, asking basic questions, (i.e., "Do you have any symptoms?") and only direct urgent care issues to medical professionals. Bots can do the selling with the right script. With the bot, conversational commerce leaves room for personalized upselling as the bot makes suggestions. The bots are capable of retaining information, and those details can reach out personally, offering relevant content at the right time. The bot reminds employees to apply the hand sanitizer and cleaning wipes on the premises, and checks that their offices all be cleaned and sanitized frequently. The system reminds employees at appropriate time to conform to Social Distancing. Data from chatbot screening enables employees to feel comfortable coming back to their offices. A person who is known to be infected or showing symptoms is not to be allowed access. The system provides Privacy & Security. Like other sensitive healthcare information, COVID-19 status data needs to be handled extremely carefully by employers. Top of mind considerations include receiving consent from employees to share their health information, securing data infrastructure to store this info, and limiting access control to this information within the company. The system provides flexibility for multiple inputs. Guidance from government agencies and the scientific community is changing all the time on what an employer needs to verify to bring an employee back to work. This includes a combination of antibody test results, data pulled from contact tracing apps, and any history of confirmed infection. HR teams need to connect these inputs to a variety of human resources information systems (HRIS) to match active employee records with COVID-19 related data. With people consent, the system can combine different inputs (such as user-submitted information and trusted third-party sources) to verify this sensitive data while restricting access to employees and designated admins.

The AI architecture can be used for other communication issues, for example, to generate long text or video using the neural network architectures. These other uses are detailed next.

In another aspect for AI content generation, computerized systems and methods are disclosed to generate a document by providing a document structure having one or more seed landmark texts therein, each landmark text including a milestone overview text and a plurality of component texts; from the milestone overview text, generating one or more computer-generated text suggestions to supplement the milestone overview text; combining the milestone overview text with each component text and generating one or more computer-generated component text suggestions; and creating the document by combining the milestone overview, the one or more computer-generated text suggestions, and each component text with corresponding one or more computer-generated component text suggestions.

In yet another aspect, a method to generate content with a plurality of images or video includes providing a multimedia structure having one or more seed landmark images therein, each landmark image including a milestone overview text and a plurality of component texts; from the milestone overview text, generating one or more computer-generated image suggestions to supplement the landmark image; combining the milestone overview text with each component text and generating one or more computer-generated component image suggestions; and creating the content by combining the landmark image and the one or more computer-generated image suggestions.

In a further aspect, a method provides a chatbot trained with context sensitive data whose response is biased during runtime with highly customized responses and with realistic human like response is presented.

In yet another aspect, a chatbot serves in place of human agents to provide answers for customers. The bot detects user emotions and if it detects charged emotions, get help from the best matching agent to help the customer.

In yet a further aspect, a web site content generator renders AI content that is SEO optimized. The text includes ontology or semantic tags to aid a search engine in locating best matching responses that are in natural language.

Implementations of the above aspects may include one or more of the following additions to the above aspect:

2. the document structure comprises an outline, wherein each landmark text comprises a chapter overview, and wherein the component texts comprise a chapter outline.

3. the document comprises a fiction work, a non-fiction work, a computer readable code, a machine specification, or a mechanical description.

4. the document structure comprises one or more figures, wherein each figure comprises a brief description of the drawing, a figure description overview, and a detailed description for the figure with component texts corresponding to items in the figure.

5. biasing neural network weights with the milestone overview text when generating a context-sensitive component text suggestion.

6. the combining further comprises combining a title and a background text with the one or more seed landmark texts and providing the combined title, background, and seed landmark texts to a learning machine to synthesize artificial-intelligence-generated text.

7. extracting one or more references from a figure and annotating the one or more references with text; and forming one or more artificial-intelligence-generated reference text suggestions.

8. performing grammar analysis and suggesting grammar correction and editing the document for conciseness.

9. applying a transformer with an encoder that reads the text input and a decoder that produces a prediction for the text.

10. the transformer comprises a generative pre-trained transformer (GPT).

11. applying GPT (Generative Pre-trained Transformer) model or a BERT (Bidirectional Encoder Representations from Transformers) model to generate the text.

12. determining when two pieces of text, component, module, code, data structure, or image perform a similar task and showing the determined text, component, module, code, data structure, or image to a user.

13. breaking-down the milestone overview text into one or more alternate components with different component text but capable of performing the milestone overview text based on teachings from prior art documents and showing the one or more alternate components as a artificial-intelligence-generated design around satisfying the milestone overview text, wherein the breaking-down comprises applying an artificial intelligence software to detect similarity of functions.

14. detecting plagiarism in the document by matching the document text to text crawled from the Internet.

15. generating a part list by detecting noun phrases (NPs) in the document and corresponding numbers for the NPs.

16. generating a list of claimed elements.

17. generating a list of unclaimed elements.

18. The method of claim 1, wherein the document is part of a portfolio accessible to one or more licensees.

19. granting rights to the document and/or guiding text generation with a chatbot.

Advantages of the system may include one or more of the following. The system increases communication effectiveness. The system generates good technical writing in a time-saving manner, and the results avoid misunderstanding and increase workplace efficiency by promoting good communication between engineers and other staff. The system directs the writing to the intended audience will allow the reader to understand the content on the first read, rather than needing to ask for additional details or explanation. By understanding the audience's goal in reading the document, the system helps the writer to highlight the important data, focusing on significant supplementary or background information and bringing such information to the user to decide. Thus, the information needed for a decision, instruction or education take center stage. The system keeps the information accessible and uses the simplest and most direct language to convey the information with a neutral and professional tone. The system helps the users with diagrams or schematics where they add value and increase reader comprehension. When used, the diagrams are directly referenced within the text and clearly explained in the text. The system provides a Visual and intuitive user interface with built-in semantic and technical understanding, automatic relevant passage suggestions. The system reduces the cost of writing documents by serving as writing assistants that fill (or inbetween) details based on the abstract. For more technical descriptions where engineering details are important, the system can expand from an abstract to a full description with clarity. In other applications that demand flowery language, the efficiency of human drafters can be improved significantly when a master drafter generates a summary of the major points in the article, and the computer fills in the missing details, much similar to inbetweening of animation. The user would draw the keyframes which define the movement, then, hands the scene to a human or computer assistant. The assistant does the clean-up and the necessary inbetweens, or, in large studios, only some breakdowns which define the movement in more detail, before handing down the scene to their assistant, the inbetweener, who does the rest. The system can adapt the detail resolution or rate to the current scene. Detailed points may be written on threes or fours chapters of writeups. Different scenes components of a story might be animated at different resolutions or rates to conform to the master drafter's command. The result is a significant speedup in document generation, while cost is reduced.

One embodiment provides a chatbot to provide advice to patients of an infectious disease such as COVID19. Such chatbot may get the U.S. Food and Drug Administration (FDA) 510(k) and European CE approval for public use. The system applies a trained chatbot operating in concert with mobile fitness monitoring and contact tracing to assist users in answering their health questions in an efficient timely manner that minimizes compute resources and health professional time to free them up for ICU patients, for example. The system can receive FDA 501k or CE clearance approval. The chatbot crawls official government communications about COVID-19 from governments and the World Health Organization as well as predetermined vetted sources, the chatbot in conjunction with a mobile app assesses known symptoms and answers questions about government policies.

The process starts with the appropriate deep neural network architecture (for example, retrieval, generative, and retrieve/refine, transformer-based, BERT-based, GPT-based, among others) for a learning machine, and then performs the following:

Collect training data and update on periodic basis:

Store non-public information into a database from a site desiring to have a chatbot to answer questions, including hospital databases for patient private data and databases containing mobile fitness tracking devices for users Crawl web site of WHO, government agencies, and predetermined research institutions knowledgeable about infectious diseases to extract instructions, frequently asked questions (FAQs) and question and answers (Q&As), and all publicly available text Crawl the internet for any mention of solutions/methods/product names including negative reviews as training data Train learning machine with data that is logically grouped or clustered to provide context and accuracy (for example, by age, sex, race, home location, health history, social economics, risks for lung or breathing diseases etc) and periodically update training with new data Gather customization information from user by collecting recent data from mobile fitness devices and by interacting with the user and retrieving prior interactions with the user and prior health reports by the user, as well as by the clusters of people the user is affiliated with Determine the trained group or cluster best matching the health condition information and apply the customization information to bias the learning machine to generate context-sensitive chats that are optimized to answer or interact with the user regarding symptoms Detect user emotions during the interaction based on user facial expression (periodic sampling of camera image and/or verbal expression), or based on text response by user, or by explicit happiness rating next to the chat box text entry space If user is satisfied with the interaction based on detected emotion, continue responding/chatting If user appears ill, upset or exhibits unusual behaviors not observed before, request opportunity to have a health professional to follow up at later time, or optionally select a call-center agent best matched to the user profile or need and transfer to selected agent at a call center for assistance.

As part of the analysis, the chatbot detects users with higher risk such as users with suppressed immune systems (cancer treatment or who have recently had an organ transplant), unvaccinated users that may be susceptible against common infectious diseases, healthcare workers, users who are at or traveling to at-risk areas where they may be exposed to mosquitoes that carry pathogens, among others.

In one implementation, vital signs from smart watches can be used to monitor core body temperature pattern, breathing pattern, coughing pattern, and walking/exercise patterns to detect changes indicative of an infectious disease. The breathing rate/pattern can be detected through EKG or other means. The coughing pattern can be detected by sound using a microphone, or can be done through body motions as detected by accelerometers, which also detect the walking/exercise patterns. Contact tracing can be done to detect group activities and associated people to see if there are group activities indicative of an outbreak in the group. Communications with members of such group are also used to infer on-set of the disease among the group.

Such information can be used when the chatbot asks the user for symptoms. Symptoms of infectious disease are particular to the type of disease. For example, Symptoms may appear 2-14 days after exposure to the virus. Symptoms of COVID-19 may include Fever or chills, Cough, Shortness of breath or difficulty breathing, Fatigue, Muscle or body aches, Headache, New loss of taste or smell, Sore throat, Congestion or runny nose, Nausea or vomiting, Diarrhea, Trouble breathing, Persistent pain or pressure in the chest, New confusion, Inability to wake or stay awake, or Bluish lips or face, according to the CDC. Symptoms of influenza include: Fever, Chills, Congestion, Fatigue, Muscle aches and headache. Other infectious diseases, such as Shigella, cause more serious symptoms, including Bloody diarrhea, Vomiting, Fever, Dehydration (lack of fluid), and Shock.

The system also helps patients with chronic conditions, many of whom are foregoing urgent care out of fear of getting Covid-19 at the hospital. For example, if the user's medical history shows hypertensive from the data, and if the user is not being treated for or charged for high blood pressure medicine, the system can alert the doctor and suggest medicine for their hypertension. The chatbot can detect situations maybe they were taking it, stopped taking it, and they haven't gotten a refill because of Covid.

The chatbot can serve factual answers to user's questions. Users often query a search engine with a specific question in mind and often these queries are keywords or sub-sentential fragments. The chatbot may rely on multiple methods to measure the matching degree between a question and an answer candidate.

The system becomes a source for trusted information on a topic of interest to the site clients and prospective buyers means that the web pages are successfully putting the user experience first. Schema, a semantic vocabulary of tags (or microdata), can be added to a site's HTML code to enhance search engines' ability to read and represent web pages in SERPs. While rich snippets do not directly influence a site's rankings, structured data markup to enable rich snippets may generate indirect SEO paybacks by making your page more effortlessly indexable. It also informs search engines about what's important to you in your content and does a better job with accurate and targeted metadata. The markup provides search engines with better structured content which in turn it can use to provide answers to searchers. It can affect rankings in SERPs and improve the domain authority of the website by indirectly influencing the page's visibility through SERP featured snippets.

ClaimReview Schema markup is used to help search engines interpret your pages to fit the context of a search query. At a high level, claimReviewed, claimUrl, claimUrilOriginal are all attributes of ClaimReview. The system can use Google Data Search is surfacing new datasets that can be sourced to back up the computer-generated text's claims. ClaimReview-based factcheck markup defines a structure that corresponds to the kind of information included in many fact-checking pages. The fundamental notion is a ClaimReview has an author (schema.org/author), which is typically an Organization (schema.org/Organization) (i.e. the fact checking organization or publisher), but could also be a Person (schema.org/Person). The claimReviewed (schema.org/claimReviewed) property of a ClaimReview (schema.org/ClaimReview) summarizes the claim being reviewed. This may include clarifications of the original wording to address intelligibility, civility, context or brevity, and can include translations. This value of the claimReviewed (schema.org/claimReviewed) property is typically a simple textual string (but could be a Claim (schema.org/Claim) with a text (schema.org/text) property, although this is not encouraged). The itemReviewed (schema.org/itemReviewed) property of ClaimReview (schema.org/ClaimReview) indicates specific manifestations of the claim being reviewed. This can either be a Claim (schema.org/Claim) [preferred] or [historically] a CreativeWork (schema.org/CreativeWork) within which the claim is described or reported. The value of itemReviewed (schema.org/itemReviewed) (preferably a Claim (schema.org/Claim) to avoid ambiguity) has an author (schema.org/author), which is a Person (schema.org/Person) or Organization (schema.org/Organization) that has made the claim. A Claim (schema.org/Claim) can be associated with a CreativeWork (schema.org/CreativeWork) it occurs in, using the appearance (schema.org/appearance) or firstAppearance (schema.org/firstAppearance)properties. This is preferable to describing appearances using itemReviewed (schema.org/itemReviewed) as it distinguishes more explicitly between the author (schema.org/author) of the Claim (schema.org/Claim) versus author (schema.org/author) of materials discussing those claims. The reviewRating (schema.org/reviewRating) property of the ClaimReview (schema.org/ClaimReview) indicates a Rating (schema.org/Rating) of the claim. A rating can be summarized textually with a alternateName (schema.org/alternateName) property, and with a numerical rating on a scale from worstValue (schema.org/worstValue) (lowest) to bestValue (schema.org/bestValue) (highest). The author (schema.org/author) (or creator (schema.org/creator), publisher (schema.org/publisher) of a ClaimReview (schema.org/ClaimReview), or of a Claim (schema.org/Claim), or CreativeWork (schema.org/CreativeWork), can be either an Organization (schema.org/Organization) or Person (schema.org/Person).

In another embodiment, the sensor(s) can collect vital signs such as temperature, heart rate, ECG, EEG, PPG, and bioimpedance, among others. For example, in one aspect, a system includes a cellular, WiFi, or and Bluetooth or UWB transceiver coupled to a processor; an accelerometer or a motion sensor coupled to the processor; and a sensor coupled to the processor to sense mood body vital sign, wherein text, image, sound, or video is rendered in response to a sensed mood or body vital sign; and a wearable device operating wirelessly with the processor, wherein the wearable device includes at least one sensor coupled to a back of the wearable device and wherein the wearable device recognizes and executes the speech command. In another aspect, a mobile system, comprising: a transceiver to communicate data via a personal area network (PAN); an accelerometer and a gyroscope; a processor coupled to the transceiver, the accelerometer and the gyroscope, the processor executing one or more applications to record user speech and to record data regarding movement detected by the accelerometer and the gyroscope; two or more sensors in communication with the processor to detect user vital sign data; and a health application executed by the processor to generate a health analysis using the vital sign data and the data regarding movement detected by the accelerometer and the gyroscope, wherein the transceiver communicates the analysis to another computer via the PAN.

In yet another aspect, a system includes a processor; a cellular, WiFi, or Bluetooth or UWB transceiver coupled to the processor; an accelerometer or a motion sensor coupled to the processor; and a sensor coupled to the processor to sense mood, wherein text, image, sound, or video is rendered in response to the sensed mood. In another aspect, a system includes an accelerometer to detect movement or fitness; a sensor coupled to a wrist, hand or finger to detect blood-oxygen levels or heart rate or pulse rate and mounted on a wristwatch wearable device and a voice communication device having a wireless transceiver adapted to receive blood-oxygen level or heart rate or pulse rate from the sensor over a wireless personal area network (PAN). In yet another aspect, a system includes a cellular telephone having a vital sign sensor thereon to detect heart rate, pulse rate or blood-oxygen levels; and a wristwatch wearable device in wireless communication with the cellular telephone, including: a sensor coupled to a wrist, hand or finger to detect blood-oxygen levels, heart rate or pulse rate; a wireless transceiver adapted to communicate with the cellular telephone over a wireless personal area network (PAN); and a processor coupled to the sensor and the transceiver to send pulse rate to the cellular telephone. In a further aspect, a health care monitoring system for a person includes one or more wireless nodes forming a wireless network to communicate data over the wireless network to detect a health problem. Implementations can include watches that capture fitness data (activity, heart rate, blood pressure, walking rate, dietary or calorie consumption, among others) and sending the data to a hospital database where medical and fitness data is used to treat the patient. Other implementations include collecting data from different devices with different communication protocols such as blood pressure measurement devices, scales, glucose meters, among others, and upload the data to a computer which converts the data into an intermediate format that is compatible with different protocols for interoperability purposes. In another aspect, a heart monitoring system for a person includes one or more wireless nodes forming a wireless network; a wearable sensor having a wireless transceiver adapted to communicate with the one or more wireless nodes; and a software module receiving data from the wireless nodes to detect changes in patient vital signs. In another aspect, a monitoring system includes one or more wireless nodes forming a wireless network; a wearable blood pressure sensor having a wireless transceiver adapted to communicate with the one or more wireless nodes; and a software module receiving data from the wireless nodes to detect deteriorations in patient vital signs. In another aspect, a health care monitoring system for a person includes one or more wireless nodes forming a wireless mesh network; a wearable appliance having a sound transducer coupled to the wireless transceiver; and a bio-electric impedance (BI) sensor coupled to the wireless mesh network to communicate BI data over the wireless mesh network. In another aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth. In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected. In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected. In yet another aspect, a monitoring system for a person includes one or more wireless nodes forming a wireless network; and a wearable device including: a processor; a transceiver coupled to the processor to communicate with the one or more wireless nodes; a wearable sensor on a patch or bandage secured to the person's skin and coupled to the processor; an accelerometer coupled to the processor; and a thumb sensor coupled to the processor. In another aspect, a health monitoring system for a person includes a mobile telephone case including a cellular transceiver to provide wireless data and voice communication; a sensor including one or more electrodes mounted on the mobile telephone case to contact the person's skin and capture bio-electrical signals therefrom; an amplifier coupled to the electrodes; a processor coupled to the amplifier; and a screen coupled to the processor to display medical data such as images of the bio-electrical signals. Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth or UWB VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected. In another aspect, a monitoring system for a person includes one or more wireless bases; and a cellular telephone having a wireless transceiver adapted to communicate with the one or more wireless bases; and an accelerometer to detect a dangerous condition and to generate a warning when the dangerous condition is detected. In one aspect, systems and methods include one or more entities including a sensor configured to provide data in at least a first information standard from a first manufacturer and a second information standard from a second manufacturer; and an electronic health record database configured to: capture information from the one or more entities, normalize the captured information from first and second manufacturers in a common format, and add metadata for the captured information. In another aspect, an interoperable health-care system includes a network; one or more medical data collection appliances coupled to the network, each appliance transmitting data conforming to an interoperable format; and a computer coupled to the network to store data for each individual in accordance with the interoperable format. The user can take his/her weight, blood pressure, and cholesterol measurement daily, and the data is sent from a health base station to a monitoring service at his doctor's office. Periodically, the user gets an automated health summary generated by a service at his doctor's office as well as information to help him maintain a healthy lifestyle. The health information can be stored in an external HIPAA compliant health storage database so that the user and his doctor can access his health information over the web. The system extends health care system into the home and can record personal health data on a systematic periodic basis. Appointments can be automatically scheduled with providers. Long-term data for medical baseline can be collected. The system can also provide predictive alerts for high-risk conditions. The system can perform initial triage utilizing biosensors, images, e-mail/chat/video.

In one embodiment, the radio is a micro-positioning radio such as a 5G enabled micro-positioning radio. IOT modules include a computer processor connected to UWB via either a cable or via a socket connection. The modules also include a communication radio to send data to a separate processor for display. Modules can be placed on corners but can also be in a variety of components or added as a plug and play using magnets or other forms of temporary attachments. The modules can be placed on a support structure such as a room or a vehicle in a temporary fashion without manually measuring the position because the UWB can be used to range between modules and establish the room, office vehicle, lab, conference room, or cubicle as a constellation with known relative positions. The ranges between the modules are inputted to the software on the processor. The software uses the ranges to create a known geometric constellation of the UWB radios and then uses the known offset of the modules to calculate the relative locations of the modules to one another. These ranges are then used by the software on the processor to trilaterate to the external device. The relative location of the external device is used by software on the processor to produce a range and bearing to the potential target. Event Horizon Calculation is then done. The range and bearing are inputted to software that is running the main event loop to track the event horizon—the timing associated with a possible collision. The software stores the data in a linked list and uses this linked list to compare the current range and bearing to the previous range and bearing for that same external device. The distance between the current and previous locations is used to calculate the rate of speed and the time associated with nearby people, and then the radio ID of the nearby people can be recorded to enable accurate and rapid automated contact tracing. In this manner, contact tracing using a mobile app, smartwatches, and physical tracing is provided to rapidly contain infections. One embodiment provides a UWB Exposure Notification Service for proximity detection of nearby wearable devices and smartphones, and for the data exchange mechanism. Exposure Notification Service uses the UWB service for detecting device proximity. It uses a Temporary Exposure Key generated every 24 hours for privacy consideration. The result is a Diagnosis Key—The subset of Temporary Exposure Keys uploaded when the device owner is diagnosed as positive for the coronavirus. A Rolling Proximity Identifier, which is a privacy-preserving identifier derived from the Temporary Exposure Key can be sent in the broadcast of the UWB payload. The identifier changes about every 15 minutes to prevent wireless tracking of the device. An Associated Encrypted Metadata (AEM) is privacy-preserving encrypted metadata used to carry protocol versioning and transmit (Tx) power for better distance approximation. The Associated Encrypted Metadata changes about every 15 minutes, at the same cadence as the Rolling Proximity Identifier, to prevent wireless tracking of the device.

Another embodiment provides a smartphone app for employers that uses UWB signals (but Bluetooth can be used as well), Wi-Fi, GPS and other data to track where employees go around the office, who they come into contact with and for how long, to enable human resources or corporate security managers to quickly access the data in the event of a workplace outbreak and notify employees who may have been exposed. Employees will wear wristbands or carry credit card-size badges that collect UWB signals about their whereabouts and proximity to one another; that data is sent to devices that transmit it to the cloud. The chatbot identifies spots where infected workers may have recently gathered, enabling companies to shut down specific areas, rather than an entire building, for deep cleaning. The badges are preferred where employees are not allowed to bring their personal phones, as well as to people who would rather not have their employers track them on their smartphones. A Health Dashboard allows HR admins to view a list of their active employees, the most recent COVID-19 health status for each employee, and the date the record was last updated. Admins can view more details about each employee's COVID-19 history (such as a list of test results over time), and can click to verify or re-verify an employee's status. When an employer clicks "Verify", the designated employee will receive a communication such as a text or an email taking them to a consent-based chatbot flow where they can securely share their COVID-19 health data with their HR team. The employee will be required to submit information such as recent lab test results, and the system may then verify that information with the lab itself. The employee can connect tracing apps to the platform, confirming they have not been in contact with an infected individual.

Office management will opt for the screening of all employees, vendors and visitors entering their facility based on the most appropriate methods for their particular space. These may include app-enabled questionnaires, temperature checks, newly installed thermal cameras or direct virus testing when it becomes more widely available. Hourly or daily screenings of employees, vendors and visitors, making it commonplace and fully integrated with the security access control system to screen out people presenting with symptoms or known to be infected. As the availability of testing increases, those carrying antibodies or testing negative for the virus will screen in and be allowed access. Lobbies include testing stations, screening queues, speed lanes, designated check in times and self-check kiosks. A building access control system is used as part of the contact tracing by mandating credential use for both entry and exit traffic for buildings, floors, tenant office suites and common areas at all times. UWB proximity data can be further supplemented via intelligent face recognition learning machines to investigate close personal contact for more detailed tracking so people who are impacted by pathogen exposure can be quickly and easily notified. The chatbot can monitor and manage real-time space occupancy, supplementing physical guides to reinforce social distancing with real-time data reporting to provide notifications for issues such as exceeding floor-level occupancy and suggest the need for greater social distancing if the number of people in a space is too high. Utilizing access control, the chatbot can assist tenants in enforcing staggered work schedules to minimize density.

By enabling a network of readily connected health and medical devices, people with Covid or infectious disease or other chronic diseases will be able to share vital sign information such as blood pressure and glucose level with their doctors. Adult children will be able to remotely watch over their aging parents and proactively help them manage safely in their own homes. Diet and fitness conscious individuals will also be able to seamlessly share their weight and exercise data with fitness consultants through the Internet. The above system forms an interoperable health-care system with a network; a first medical appliance to capture a first vital information and coupled to the network, the first medical appliance transmitting the first vital information conforming to an interoperable format; and a second medical appliance to capture a second vital information and coupled to the network, the second medical appliance converting the first vital information in accordance with the interoperable format and processing the first and second vital information, the second medical appliance providing an output conforming to the interoperable format. The appliances can communicate data conforming to the interoperable format over one of cellular protocol, ZigBee protocol, Bluetooth protocol, WiFi protocol, WiMAX protocol, USB protocol, ultrawideband (UWB) protocol. UWB is a short-range, wireless communication protocol that uses a wide spectrum of several GHz. UWB acts as a radar that can continuously scan an entire room and precisely lock onto another UWB object or mobile device to discover its location and communicate data and for location discovery and device range with precision. The appliances can communicate over two or more protocols. The first medical appliance can transmit the first vital information over a first protocol (such as Bluetooth or UWB protocol) to a computer, wherein the computer transmits the first vital information to the second medical appliance over a second protocol (such as ZigBee protocol). The computer can then transmit to a hospital or physician office using broadband such as WiMAX protocol or cellular protocol. The computer can perform the interoperable format conversion for the appliances or devices, or alternatively, each appliance or device can perform the format conversion. Regardless of which device performs the protocol conversion and format conversion, the user does not need to know about the underlying format or protocol in order to use the appliances. The user only needs to plug an appliance into the network, and the data transfer is done automatically so that the electronic "plumbing" is not apparent to the user. In this way, the user is shielded from the complexity supporting interoperability. In another aspect, a monitoring system for a person includes one or more wireless nodes and a stroke sensor coupled to the person and the wireless nodes to determine a medical problem, for example a stroke attack. The stroke monitoring system is interoperable with emergency vehicle and/or hospital systems and provides information to quickly treat stroke once the patient reaches the treatment center.

In one aspect, a monitoring system for a person includes one or more wireless nodes and an electromyography (EMG) sensor coupled to the person and the wireless nodes to determine a medical issue such as a stroke attack. In another aspect, a health care monitoring system for a person includes one or more wireless nodes forming a wireless mesh network; a wearable appliance having a sound transducer coupled to the wireless transceiver; and a bioelectric impedance (BI) sensor coupled to the wireless mesh network to communicate BI data over the wireless mesh network. In a further aspect, a heart monitoring system for a person includes one or more wireless nodes forming a wireless mesh network and a wearable appliance having a sound transducer coupled to the wireless transceiver; and a heart disease recognizer coupled to the sound transducer to determine cardiovascular health and to transmit heart sound over the wireless mesh network to a remote listener if the recognizer identifies a cardiovascular problem. The heart sound being transmitted may be compressed to save transmission bandwidth. In yet another aspect, a monitoring system for a person includes one or more wireless nodes; and a wristwatch having a wireless transceiver adapted to communicate with the one or more wireless nodes; and an accelerometer to detect a dangerous condition and to generate a warning when the dangerous condition is detected. In yet another aspect, a monitoring system for a person includes one or more wireless nodes forming a wireless mesh network; and a wearable appliance having a wireless transceiver adapted to communicate with the one or more wireless nodes; and a heartbeat detector coupled to the wireless transceiver. The system may also include an accelerometer to detect a dangerous condition such as a falling condition and to generate a warning when the dangerous condition is detected. Implementations of the above aspect may include one or more of the following. The wristwatch determines position based on triangulation. The wristwatch determines position based on RF signal strength and RF signal angle. A switch detects a confirmatory signal from the person. The confirmatory signal includes a head movement, a hand movement, or a mouth movement. The confirmatory signal includes the person's voice. A processor in the system executes computer readable code to transmit a help request to a remote computer. The code can encrypt or scramble data for privacy. The processor can execute voice over IP (VOIP) code to allow a user and a remote person to audibly communicate with each other. The voice communication system can include Zigbee VOIP or Bluetooth or UWB VOIP or 802.XX VOIP. The remote person can be a doctor, a nurse, a medical assistant, or a caregiver. The system includes code to store and analyze patient information. The patient information includes medicine taking habits, eating and drinking habits, sleeping habits, or excise habits. A patient interface is provided on a user computer for accessing information and the patient interface includes in one implementation a touch screen; voice-activated text reading; and one touch telephone dialing. The processor can execute code to store and analyze information relating to the person's ambulation. A global positioning system (GPS) receiver can be used to detect movement and where the person falls. The system can include code to map the person's location onto an area for viewing. The system can include one or more cameras positioned to capture three dimensional (3D) video of the patient; and a server coupled to the one or more cameras, the server executing code to detect a dangerous condition for the patient based on the 3D video and allow a remote third party to view images of the patient when the dangerous condition is detected. More details are disclosed in application Ser. Nos. 16/894,040 and 16/894,058, the contents of which are incorporated by reference.

One embodiment can serve as a physician assistant that has a corpus of the medical literature. The corpus has recent publications as well. The physician assistant chatbot can communicate with the patient prior to admission and, based on the communications, can generate a list of issues for the physician.

The chatbot enables virtual triage to scale front-line response. Automating their question-answer needs frees up doctors and medical resources to respond. The chatbot walks patients through questions and provides answers. Based on individual responses, the bot initially walks users through predefined conversational workflows to guide subsequent question-answering. One method for the chatbot includes: receiving from a patient a narrative of a medical issue, generating one or more hypothesis and retrieving symptoms for each hypothesis, matching the symptoms with prior medical history; identifying one or more probable diagnosis based on the narrative and previous medical history; and probing the patient for confirmatory indications.

Once the relevant details have been captured, the chatbot can take actions such as a specific recommendation to the patient (to schedule a virtual visit, call a provider, visit an emergency department, review educational information, etc.) The chatbot uses data that is frequently updated with the guidelines from the CDC and other clinical sources such as the Mayo Clinic. The chatbot can automate next step actions such as scheduling virtual or in-person visits, talking with a live or online chat agent, or requesting a review of specific patient education material. The chatbot supports symptomatic and at-risk individuals as they manage symptoms, using assessments that can be sent through chatbot, text-message or phone calls at regularly scheduled intervals. One embodiment helps employers screen, check-in and manage their employees to provide and optimize employee health, direct individuals to supportive resources, and provide clearance for work. Another embodiment supports patient emotional health with personalized conversations using psychological techniques. To further help one improve their emotional health, the app features personalized meditations as well as the ability to track mood and monitor emotional health. As users communicate with the chatbot, it will learn more about them and fine-tune the experience to fit their needs.

In one embodiment for generating technology or field specific long form text to answer a COVID technical question using patent literature, the process is as follows:

First, the field needs to be identified. For example, the transformer training can be tailored to specific classifications such as the IPC code. In one embodiment, the process identifies the international patent classification (IPC) code using various ways: 1) ask user to indicate or select IPC with graphical user interface, or 2) auto detect IPC from contextual data Token Bias Process Train BERT (or similar transformer) to classify sections of patent text (title, summary, abstract, technology field, . . . ) to predict an IPC Given user contextual data (title, summary, abstract, technology field, . . . ), predict likely IPC Assign token values to each IPC class (outside of vocabulary)

Tokenize input text

Prepend IPC token to input block—This has the effect of notifying the model at train and generation time of the IPC class at each forward pass, thus biasing predictions towards IPC-specific outputs One exemplary model has the following parameters: block_size=200, vocab_size=52000, and the ipc parameters are: n_ipcs=1500, the final dimensions of the model are: block_size=201 and vocab_size=53500

The token bias includes:

Collate all contextual data (title, claims, abstract, field of invention, . . . )

Tokenize context via model tokenizer

Determine token frequencies as map {token:freq}

At generation step, augment token sampling probabilities using a predetermined policy, for example:

P=sampling probability distribution over all tokens in vocabulary i=initial token prob given prompt f=frequency of token in context d=high-frequency damper (0-1 for damping effect, >1 for emphasis)

a=augmentation constant (user selected)

overwrite i:

$i <= (i*(f\hat{}d))*_a$ (This has the effect of selectively biasing generation of more frequent tokens)

Re-normalize P s.t. sum(P)==1 (required for sampling):

P_aug<=softmax(P)

Sample next token using P_aug instead of P.

The foregoing customization of response can be used in other applications such as chatbots and SEO optimization.

A chatbot system that applies the above methodology to answering user questions on an automated basis, thus greatly reducing cost and increasing customer convenience due to its ability to resolve issues 24×7 can be as follows:

Select deep neural network architecture (for example, retrieval, generative, and retrieve/refine, transformer-based, BERT-based, GPT-based, among others) for a learning machine Collect training data and update on periodic basis:

Store non-public information into a database from a site desiring to have a chatbot to answer questions, including CRM databases for common user questions and non-public product maintenance or service information for products Crawl web site of the company desiring to have the chatbot to answer questions to extract user manuals, FAQs and all publicly available text Crawl fan sites or product review sites for information about company/product/service Crawl competitor sites to extract industry text Crawl the internet for any mention of the company name or product names including negative reviews and flag such reviews for company responsive text as training data Train learning machine with data that is logically grouped or clustered to provide context and accuracy (for example, by technology field; by product; by customer type (engineers, housewife, student, . . . , or by industry/specialization, etc) and periodically update training with new data Gather customization information from user by interacting with the user and retrieving prior interactions with the user and prior purchases and complaints/returns by the user Determine the trained group or cluster best matching the customization information and apply the customization information to bias the learning machine to generate context-sensitive chats that are optimized to answer or interact with the user Detect user emotions during the interaction based on user facial expression (periodic sampling of camera image and/or verbal expression), or based on text response by user, or by explicit happiness rating next to the chat box text entry space If user is satisfied with the interaction based on detected emotion, continue responding/chatting If user is dissatisfied based on detected emotion, select a call-center agent best matched to the user profile or need and transfer to selected agent at a call center One embodiment employs the poly-encoder architecture which encode global features of the context using multiple representations (n codes, where n is a hyperparameter), which are attended to by each possible candidate response. This final attention mechanism gives improved performance over a single global vector representation (so-called "biencoders"), whilst still being tractable to compute compared to simply concatenating input and output as input to a Transformer (or "crossencoders"). A Seq2Seq Transformer architecture is used to generate responses rather than retrieve them from a fixed set. One implementation is based on the ParlAI version with Byte-Level BPE tokenization trained on the pre-training data, as implemented in HuggingFace's Tokenizers.

To avoid producing dull and repetitive chat responses, given the dialogue history, the retrieval model is first used to produce a draft response which is then appended to the input sequence of the generator, along with a special separator token. The generator then outputs a response as normal given this modified input sequence. Alternatively, the system can retrieve from a large knowledge base, instead of retrieving an initial dialogue utterance and then condition the generation on the retrieved knowledge. The same retrieval system uses a TF-IDF-based inverted index lookup over the collected/crawled data to produce an initial set of knowledge candidates. A Transformer retriever model is then used to rank the candidates and select a single sentence which is used to condition generation. A Transformer-based classifier is trained to choose when to perform retrieval or not on a per-turn basis, as some contexts do not require knowledge. This was trained as a two-class classifier discriminating between contexts that require knowledge or not in the fine-tuning tasks.

The domain specific training of the learning machine enables it to have in-depth knowledge if sufficiently interrogated. The system uses industry specific jargon due to the domain training so that it does not use generic/simpler language and it does not repeat oft-used phrases.

The system uses classifiers of toxic language trained on adversarial toxic data that fools existing classifiers and is then used as additional data to make them more robust. The classifier at test time to detect toxic language before it is rendered by the chatbot. The system also mitigates race and gender bias in dialogue through conditional generation, controlling the amount of racial or gendered words to be more neutral.

In the user emotion detection, the chatbot can request access to camera and microphone (mike). If permitted, a variety of analysis can be done, but if not, text-based emotion analysis can be done. The system uses deep learning to recognize emotional intent patterns in human text, speech and facial expressions and respond to those cues in appropriate, empathetic ways—such as offering directions or information. Sentiment analysis for understanding the underlying feelings and emotions in opinions, whether written or spoken. One embodiment uses the transformers described herein and trained to analyze emotion based on the video/sound/text. A transformer model is used to fuse audio-visual-text modalities on the model level. A multi-head attention produces multimodal emotional intermediate representations from common semantic feature space after encoding text, audio and visual modalities, as supplemented by long-term temporal dependencies with self-attention.

If camera/mike access is allowed, facial analysis for frowning and voice pitch analysis and text sentiment analysis can be done in one embodiment. In other embodiments, posture, what's happening in the environment, physiological information such as what's going on with the nervous system, and smile context detection on a specific person in a specific situation can be done. Additionally, patterns in people with similar characteristics like gender sampled across cultures can be done to increase emotion detection accuracy. A number of emotional detection modules can be used, for example: DELTA is a deep learning based natural language and speech processing platform; Emotion Recognition Neural Networks using DNN with tensorflow; Emopy—deep neural net toolkit for emotion analysis via Facial Expression Recognition (FER); Emotion Recognition—Real time emotion recognition; Speech Emotion Analyzer—The neural network model is capable of detecting five different male/female emotions from audio speeches. (Deep Learning, NLP, Python); Cony Emotion—This repo contains implementation of different architectures for emotion recognition in conversations; Deepface—A Lightweight Deep Face Recognition and Facial Attribute Analysis (Age, Gender, Emotion and Race) Framework for Python; Emotion Detection—Real-time Facial Emotion Detection using deep learning; Emotion—Recognizes human faces and their corresponding emotions from a video or webcam feed; and Multimodal Emotion Recognition—A real time Multimodal Emotion Recognition web app for text, sound and video inputs; among others, the content of the documentations from their respective github sites are incorporated-by-reference.

For text only analysis, one embodiment uses the vaderSentiment package that provides a measure of positive, negative, and neutral sentiment. For given input text data, vaderSentiment returns a 3-tuple of polarity score percentages and a single scoring measure, referred to as vaderSentiment's compound metric. Other suitable sentiment analysis tools can be used.

If user dissatisfaction is detected, the system forwards the user to a call center agent using a selection process determined by the learning machine trained for routing users to agents includes rating agents on performance or success of agent data and caller data, or both. The checking for optimal interaction includes combining agent work performance, agent demographic/psychographic data, and other work performance data ("agent data"), along with demographic, psychographic, and other business-relevant data about callers ("caller data"). Agent and caller demographic data can be: gender, race, age, education, accent, income, nationality, ethnicity, area code, zip code, marital status, job status, credit score, for example. Agent and caller psychographic data can cover introversion, sociability, work/employment status, film and television preferences, among others.

A chatbot system applies the above methodology to routing a caller to a predetermined call center agent to optimize conversion, sales, or any other business goals. The process is as follows:

Select deep neural network architecture (for example, retrieval, generative, and retrieve/refine, transformer-based, BERT-based, GPT-based, among others) for a learning machine Collect training data and update on periodic basis:

Store non-public information into a database from a site desiring to have a chatbot to answer questions, including CRM databases for common user questions and non-public product maintenance or service information for products, and CRM databases for customer profiles and agent profiles Crawl web site of the company desiring to have the chatbot to answer questions to extract user manuals, FAQs and all publicly available text Crawl fan sites or product review sites for information about company/product/service Crawl competitor sites to extract industry text Crawl the internet for any mention of the company name or product names including negative reviews and flag such reviews for company responsive text as training data Train learning machine with data that is logically grouped or clustered to provide context and accuracy (for example, by customer profile; by agent grade/performance, by agent-caller interaction history; by technology field; by product; by customer type (engineers, housewife, student, . . . , or by industry/specialization, etc) and periodically update training with new data Gather customization information from user by interacting with the user and retrieving prior interactions with the user and prior purchases and complaints/returns by the user Determine the trained group or cluster best matching the customization information and apply the customization information to bias the learning machine to generate context-sensitive chats that are optimized to answer or interact with the user Route caller to select agent based on trained learning machine Detect user emotions during the interaction based on user facial expression (periodic sampling of camera image and/or verbal expression), or based on text response by user, or by explicit happiness rating next to the chat box text entry space If user is satisfied with the interaction based on detected emotion, continue agent-caller interaction If user is dissatisfied based on detected emotion, select another call-center agent best matched to the user profile or need and transfer to new selected agent or supervisor (escalation of service)

The training data includes caller data associated with one or more callers (e.g., a caller on hold), agent data associated with one or more agents (e.g., one or more available agents). Caller data (such as a caller demographic or psychographic data) is determined or identified for a caller. The system can get caller data from available databases by using the caller's contact information as an index. Available databases include, but are not limited to, those that are publicly available, those that are commercially available, or those created by a contact center or a contact center client. If the caller's contact information is not already known, caller data can be retrieved from the CallerID information or by requesting this information of the caller at the outset of the contact, such as through entry of a caller account number or other caller-identifying information. Other business-relevant data such as historic purchase behavior, current level of satisfaction as a customer, or volunteered level of interest in a product may also be retrieved from available databases. Agent data includes agent grades (which may be determined from grading or ranking agents on desired outcomes), agent demographic data, agent psychographic data, and other business-relevant data about the agent (individually or collectively referred to in this application as "agent data"), along with demographic, psychographic, and other business-relevant data about callers (individually or collectively referred to in this application as "caller data"). Agent and caller demographic data can comprise any of: gender, race, age, education, accent, income, nationality, ethnicity, area code, zip code, marital status, job status, credit score, and the like. Agent and caller psychographic data can comprise any of introversion, sociability, desire for financial success, film and television preferences, and the like. One method of determining agent demographic or psychographic data can involve surveying agents at the time of their employment or periodically throughout their employment such as agent grades, demographic, psychographic, and other business-relevant data, along with caller demographic, psychographic, and other business-relevant data. The learning machine matches each caller with each agent and estimates the probable outcome of each matching along a number of optimal interactions, such as the generation of a sale, the duration of contact, or the likelihood of generating an interaction that a customer finds satisfying.

The exemplary method may include determining caller data associated with one or more callers (e.g., a caller on hold), determining agent data associated with one or more agents (e.g., one or more available agents), comparing the agent data and the caller data with the transformers, and matching the caller to an agent to increase the chance of an optimal interaction. The learning machine predicts and recommends optimal interactions for every agent against every available caller. Alternatively, the computer model can comprise subsets of these, or sets containing the aforementioned sets. For example, instead of matching every agent logged into the contact center with every available caller, examples can match every available agent with every available caller, or even a narrower subset of agents or callers. Likewise, the present invention can match every agent that ever worked on a campaign—whether available or logged in or not—with every available caller. Similarly, the computer model can comprise predicted chances for one optimal interaction(s).

If best match is no possible, conventional routing via an Automatic Call Distribution (ACD) queue order or the like is done by determining a queue order of the caller. For example, if other callers are on hold waiting for an available agent, the caller may be queued with other callers, e.g., a system may order the callers in terms of hold time and preferentially map those callers that have been holding the longest. The system then maps the agent that has been waiting or idle the longest with the caller that has been holding the longest. The caller may then be routed to the agent. The system can preferentially route callers to those agents shown to have greater ability to generate sales, can increase the chances of achieving greater sales during the contacts. Similarly, other agents may be shown to generate shorter interactions with callers than that of other agents at the same contact center. By preferentially routing contacts to the agents shown to generate shorter interactions with callers, a contact center or contact center client can decrease its overall need for agents and communication bandwidth, and therefore, reduce its costs.

In exemplary search engine optimization (SEO) system, the process is as follows:

Select deep neural network architecture (for example, retrieval, generative, and retrieve/refine, transformer-based, BERT-based, GPT-based, among others) for a learning machine Collect training data:

Gather customization information from user by collecting web site map and proposed web site content for new web site design, or by crawling an existing web site, focusing on frequently asked questions (FAQs) and question and answers (Q&As) and all publicly available text Gather marketing input including marketing positioning, top keywords/semantic concept/questions to be ranked from SEO tools identifying top keywords are being used and what questions are being asked to create high quality content (system can handle target keywords with accurate keyword volume and difficulty metrics)

Crawl competitor sites to extract industry text

Crawl the internet for any mention of the company name or product names

Train the learning machine with data that is logically grouped or clustered to provide context and accuracy (for example, by technology field; by product; by customer type (engineers, housewife, student, . . . , or by industry/specialization, etc)

Determine the trained group or cluster best matching the customization information and apply the customization information to bias the learning machine to generate context-sensitive structured data markup.

Generate proposed web content that anticipates answers and solutions in the content and grow the authority of the domain Generate Semantic Knowledge Mapping and schema markup for crawlers to use Test SEO performance, and generate new text and repeat until SEO performance reaches a predetermined target The content generator suggests contents for the Website that are Topic Relevant, enabling website to be relevant to the topic and everything that is related and useful. High-scoring web pages do more than just provide sales copy or direct answers to questions. They also contain supporting information. Many times, one answer surfaces another question from the reader, so the system provides related answers and anticipate their needs. Include information the company knows customers will need—and haven't thought of before. This can be done with the custom training data such as frequently asked questions (FAQs) and question and answers (Q&As) related to the industry overall and specifically the company.

The software provides a structured approach to content creation combined with structured data markup. The software anticipates answers and solutions in the content and grow the authority of the domain to grow. In one embodiment, search tools such as Moz are queried on a periodic basis and the system can update its semantic knowledge map to generate content with the following:

1. Research user signals to create a list of questions asked.
2. Narrow the target audience and the top questions asked.
3. Use Jump Links to take viewers immediately to answers
4. Match and organize answers.
5. Optimize existing content for conversational phrases.
6. Provide answers to all top related questions.
7. Add semantic-rich search terms to content.

In addition, the system can convert existing web site content with the following:

Content Improvement: Rewriting web content with more conversational language.

Featured Snippets: Optimizing on page content to earn featured snippets atop organic results.

Schema Markup: Using structured data markup to tag elements of web pages and help search engines more accurately interpret them.

Production questions such as size, color, what a product is made of, etc., are things people are asking. Consumers are asking more questions related to a specific product before making a purchase. Follow the instructions carefully when implementing product markup. The system incorporates JSON-LD markup when possible and fitting. Reviewers often answer the questions other buyers are likely to ask. The system generates wording that aligns which purchase intent. On top of the page, the system creates a table of context, each jump-link taking the user to the part of the page answering each question. Creating jump links makes the work easier for a site visitors to quickly see just the answer that they want. Jump links to specific answers lessens your chances of a low bounce rate and improves crawling and indexing. The system automatically maintains the accuracy and freshness each product item's schema. Maintaining a correct schema helps site's content get featured in the PAA and for additional Related Questions.

Users want the best matching, concise answer immediately. With so many questions being asked, the system deciphers which answers are most needed. This helps structure the order for creating or optimizing that content. Voice searches are more conversational by nature when evaluated to text searches. Local searchers questions most often fall in this segmentation. When on the go and a need arises, people tend to speak a query. The system generates semantic knowledge mapping for both mobile and desktop search experience. The content generated by the system provides the audience with a road map to help them along their purchase journey. The common questions asked may vary at each stage; many fit long-tail keywords. For example early on consumers will likely be price comparison shopping, so their questions will center on value and use. Before pulling the trigger on a purchase, they may be asking about return policies and means of shipping.

The system generates Semantic Knowledge Mapping and generates contextual language instead of verbatim keywords. It focuses on the whole context of searcher's queries. The content length is controlled to match a searcher's intent which differs for detailed informational content and a quick answer in summary form. The system provides a semantic analysis of the natural language content, the system assists the web site content creator to locate the words in the creator's original content that capture the real meaning of the original text and then suggests text elements to assign to their logical and grammatical role and build relationships between different concepts in the text that align with BERT.

The system can apply a knowledge-based library of concepts to help search engines detect different businesses or entities are 'Known for' or to define entities better connected relationships. Web pages for specific entities may gain top positioning in search results when user engagement history indicates that search intent may include that entity within a query. The Natural Language system discerns syntax, entities, and sentiment in text, and organizes text into a predefined set of categories. The resulting content is also highly succinct, with more factual content that is written by authoritative sources. It is also engaging.

The system can transform "traditional SEO copy-writing" to better match the SEO's semantic search and update the Knowledge Graphs, entities. The system is optimized for the Searcher who Relies on Voice-Activated Searching which changes their search behavior from text input to spoken input. The system converts the original text into structured data markup that fits the context with entities along with their unique identifiers which may be used to help describe the content to search engines.

The system generates snippets, structured data, and knowledge graphs to answer people's questions and to convert the website's answers into featured snippets. Generating fresh and unique answer-rich content improves placement as a featured snippet. This is one means of giving the assistants more answer response material to match to spoken queries.

The text generation generates ontological markups or schema markups for entities on web page content, relationships to other entities, their connected relationships to attributes (properties) about those entities and the relationships to entity classifications. The system automatically generates a site's architecture, ontologies, and structured data. The system can handle Query Segmentation related to segmenting out a specific query into units of a smaller size. The system can perform custom entity modeling—especially because entity understanding helps us communicate better with real consumers. The entities provide search engines with a better and deeper understanding of topics which in turn, enable information about the Entity to be delivered in any language (with live translation if necessary), since language has only a supportive role for the query—like a modifier. Whatever Entity Understanding and Entity Relationships the search engine learns in one language can automatically be translated to other languages in the Knowledge Graph. The computer-generated markups are optimized for Direct Answers or direct answers to queries, similar a Featured Snippet. The system provides correct product/service markup and anchor text to assist gaining the position of answering the query.

The computer-generated text leverages the transformer chat-bot contents that are conversational in nature. The content produced for a website or blog incorporates conversational language. With conversational sentences integrated into a website's content, it will be simpler for users to find information on those subjects using text or voice search. A featured snippet is a block of text an SEO shows on the top of organic results for question queries, and the snippet can be used for voice assistant response.

The FAQs are provided with a question and answer schema to the FAQ as featured snippets. Schema code enables search engines to extract facts and information about entities for matching queries better. The site can associate the relationships between its content entities to their attributes and classifications. A confidence scores is then generated form relationships and added to Google's library of answers it may draw from. It not only identifies each page's highlights but is aware of notes, media elements, reviews and such within them, too.

Embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions. Computer readable program instructions described herein can be stored in memory or downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. Computer readable program instructions for carrying out operations may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Python has a large amount of libraries that are super handy for implementing sentiment analysis or machine learning from scratch. NLTK, or the Natural Language Toolkit, is one of the leading libraries for building Natural Language Processing (NLP) models, thus making it a top solution for sentiment analysis. It provides useful tools and algorithms such as tokenizing, part-of-speech tagging, stemming, and named entity recognition. SpaCy is an industrial-strength NLP library in Python which can be used for building a model for sentiment analysis. It provides interesting functionalities such as named entity recognition, part-of-speech tagging, dependency parsing, and word vectors, along with key features such as deep learning integration and convolutional neural network models for several languages. Scikit-learn is a machine learning toolkit for Python that is excellent for data analysis. It features classification, regression, and clustering algorithms. TensorFlow is the dominant framework for machine learning in the industry. It has a comprehensive ecosystem of tools, libraries, and community resources that lets developers implement state-of-the-art machine learning models. PyTorch is another popular machine learning framework that is mostly used for computer vision and natural language processing applications. PyTorch also offers a great API, which is easier to use and better designed than TensorFlow's API. Keras is a neural network library written in Python that is used to build and train deep learning models. It is used for prototyping, advanced research, and production. CoreNLP is Stanford's proprietary NLP toolkit written in Java with APIs for all major programming languages to extract the base of words, recognize parts of speech, normalize numeric quantities, mark up the structure of sentences, indicate noun phrases and sentiment, extract quotes, and much more. OpenNLP is an Apache toolkit designed to process natural language text with machine learning and supports language detection, tokenization, sentence segmentation, part-of-speech tagging, named entity extraction, chunking, parsing, and conference resolution. Weka is comprised of a set of machine learning algorithms for data mining tasks. It includes tools for data preparation, classification, regression, clustering, association rules mining, and visualization. R is a programming language that is mainly used for statistical computing. Its most common users include statisticians and data miners looking to develop data analysis. Caret package includes a set of functions that streamline the process of creating predictive models. It contains tools for data splitting, pre-processing, feature selection, model tuning via resampling, and variable importance estimation. Mlr is a framework that provides the infrastructure for methods such as classification, regression, and survival analysis, as well as unsupervised methods such as clustering.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform embodiments.

Additionally, it is understood in advance that the teachings recited herein are not limited to a particular computing environment. Rather, embodiments are capable of being implemented in conjunction with any type of computing environment now known or later developed. For example, cloud computing is a model of service delivery for enabling convenient, on-demand network access to a shared pool of configurable computing resources (for example, networks, network bandwidth, servers, processing, memory, storage, applications, virtual machines, and services) that can be rapidly provisioned and released with minimal management effort or interaction with a provider of the service. The software/system may be offered based the following service models:

Software as a Service (SaaS): the capability provided to the consumer is to use the provider's applications running on a cloud infrastructure. The applications are accessible from various client devices through a thin client interface such as a web browser (for example, web-based e-mail). The consumer does not manage or control the underlying cloud infrastructure including network, servers, operating systems, storage, or even individual application capabilities.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (for example, host firewalls).

A cloud computing environment is service oriented with a focus on statelessness, low coupling, modularity, and semantic interoperability. At the heart of cloud computing is an infrastructure comprising a network of interconnected nodes. Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (for example, mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (for example, cloud bursting for load-balancing between clouds).

All patents, published patent applications and other references disclosed herein are hereby expressly incorporated in their entireties by reference.

While the invention has been described with respect to preferred embodiments, those skilled in the art will readily appreciate that various changes and/or modifications can be made to the invention without departing from the spirit or scope of the invention as defined by the appended claims.

Many of the methods are described in their most basic form, but processes can be added to or deleted from any of the methods and information can be added or subtracted from any of the above description without departing from the basic scope of the present embodiments. The applications of the disclosed invention discussed above are not limited to certain treatments or regions of the body but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A system, comprising:
 a chamber with an exterior portion, an interior portion, and air distribution channels from a filtered air source, wherein the channels deliver filtered air toward the interior portion;
 a robot arm coupled to the chamber;
 one or more position sensors on the robot arm;
 a camera coupled to the robot arm;
 an AI visual processor receiving camera images to classify and recognize human anatomical features using a neural network or machine learning, and
 a processor coupled to the AI visual processor and the one or more position sensors to control robot movement to reach a selected anatomical target.

2. The system of claim 1, wherein the AI visual processor detects symptoms of pandemic infections on a patient.

3. The system of claim 2, wherein the AI visual processor detects lung lesions.

4. The system of claim 1, comprising an ultra-wide band (UWB) scanner or an ultrasound scanner coupled to the AI visual processor.

5. The system of claim 1, comprising one or more active air masks for people in a confined space.

6. The system of claim 1, comprising personally coupled vital sign sensors including temperature, heart rate, oxygen level sensors.

7. The system of claim 1, comprising sensors from a smart wearable device or a smart watch device to predict a person's symptoms for infectious diseases.

8. The system of claim 1, comprising a phone-based contact tracing apps to detect exposure to infectious diseases.

9. The system of claim 1, comprising air distribution channels coupled to a seat, a cabin floor, or a cabin ceiling of a vehicle.

10. The system of claim 1, comprising a low latency transceiver wirelessly coupled to a remote processor to offload processing to a remote processor.

11. The system of claim 1, comprising an infrared camera coupled to the AI visual processor, wherein the AI visual processor detects symptoms associated with fever and abnormal respiratory patterns in real time.

12. The system of claim 1, wherein the AI visual processor detects COVID symptoms in a vehicle cabin.

13. The system of claim 1, wherein the robot arm, camera, and processors comprise a portion of a vehicle cabin.

14. The system of claim 1, wherein the AI visual processor detects COVID symptoms in lung images, temperature or breathing patterns.

15. A system, comprising:
- a camera coupled to a robot arm;
- an AI visual processor receiving camera images to classify and recognize human anatomical features;
- a processor to control robot movement to reach a selected anatomical target;
- a chamber with an exterior portion, an interior portion, and air distribution channels in between and coupled to a filtered air source, wherein the channels deliver filtered air toward the interior portion;
- a view panel coupled to a head housing; and
- a flexible connector coupled to the view panel and adapted to provide a sealed environment and control entry of a pathogen outside the exterior portion.

16. The system of claim 15, wherein a chamber housing is foldable or inflatable and stored in a storage chamber in a wall, a seat, or a passenger service unit (PSU).

17. A method for treatment, comprising:
- mounting a camera on a robot system coupled to a chamber with an exterior portion, an interior portion, and air distribution channels from a filtered air source, wherein the channels deliver filtered air toward the interior portion;
- using neural networking or machine learning to classify and recognize human anatomical features from the camera output, and
- controlling one or more robot movements to reach a selected anatomical target.

18. The method of claim 17, comprising detecting pandemic symptoms through lung images, temperature or breathing patterns.

19. The method of claim 17, comprising detecting pandemic symptoms through lung images and temperature.

20. The method of claim 17, comprising operating on a patient in a moving vehicle.

* * * * *